United States Patent
Demarest et al.

(10) Patent No.: US 10,562,982 B2
(45) Date of Patent: Feb. 18, 2020

(54) METHODS FOR PRODUCING FABS AND BI-SPECIFIC ANTIBODIES

(71) Applicants: Eli Lilly and Company, Indianapolis, IN (US); The University of North Carolina at Chapel Hill, Chapel Hill, NC (US)

(72) Inventors: Stephen J Demarest, San Diego, CA (US); Xiufeng Wu, San Diego, CA (US); Raheleh Toughiri, San Diego, CA (US); Brian Arthur Kuhlman, Chapel Hill, NC (US); Steven Morgan Lewis, Chapel Hill, NC (US)

(73) Assignees: Eli Lilly and Company, Indianapolis, IN (US); The University of North Carolina at Chapel Hill, Chapel Hill, NC (US)

( * ) Notice: Subject to any disclaimer, the term of this patent is extended or adjusted under 35 U.S.C. 154(b) by 15 days.

(21) Appl. No.: 16/298,113

(22) Filed: Mar. 11, 2019

(65) Prior Publication Data

US 2019/0211115 A1   Jul. 11, 2019

Related U.S. Application Data

(63) Continuation of application No. 16/029,196, filed on Jul. 6, 2018, which is a continuation of application No. 14/773,418, filed as application No. PCT/US2014/024688 on Mar. 12, 2014, now Pat. No. 10,047,167.

(60) Provisional application No. 61/791,598, filed on Mar. 15, 2013.

(51) Int. Cl.
    *C07K 16/46*     (2006.01)
    *C07K 16/32*     (2006.01)
    *C07K 16/00*     (2006.01)
    *C07K 16/28*     (2006.01)

(52) U.S. Cl.
    CPC ............ *C07K 16/468* (2013.01); *C07K 16/00* (2013.01); *C07K 16/2863* (2013.01); *C07K 16/32* (2013.01); *C07K 2317/31* (2013.01); *C07K 2317/41* (2013.01); *C07K 2317/515* (2013.01); *C07K 2317/522* (2013.01); *C07K 2317/524* (2013.01); *C07K 2317/526* (2013.01); *C07K 2317/55* (2013.01); *C07K 2317/567* (2013.01); *C07K 2317/64* (2013.01); *C07K 2317/92* (2013.01); *C07K 2317/94* (2013.01)

(58) Field of Classification Search
    None
    See application file for complete search history.

(56) References Cited

U.S. PATENT DOCUMENTS

| | | |
|---|---|---|
| 2009/0182127 A1 | 7/2009 | Kjaergaard et al. |
| 2010/0015133 A1 | 1/2010 | Igawa et al. |
| 2014/0154254 A1 | 6/2014 | Kannan et al. |
| 2014/0200331 A1 | 7/2014 | Corper et al. |
| 2016/0039947 A1 | 2/2016 | Demarest et al. |
| 2018/0009908 A1* | 1/2018 | Aldaz ............... C07K 16/00 |

FOREIGN PATENT DOCUMENTS

WO   2007109254 A3   9/2007

OTHER PUBLICATIONS

Jordan, J., et al., "Structural understanding of stabilization patterns in engineered bispecific Ig-like antibody molecules", Proteins: Structure, Function, and Bioinformatic, vol. 77, No. 4, Dec. 1, 2009, pp. 832-841, XP055002049, ISSN: 0887-3585, DOI: 10,1002/PROT. 22502.
Schaefer, W., et al., "Immunoglobulin domain crossover as a generic approach for the production of bispecific IgG antibodies", Proceedings of the National Academy of Sciences, vol. 108, No. 27. Jul. 5, 2011, pp. 11187-11192, X9055003817, ISSN: 0027-8424, DOI: 10.1073/pnas. 1019002108.
Lewis, S., et al., "Anchored Design of Protein -Protein Interfaces", PLOS ONE, vol. 6, No. 6, Jun. 17, 2011, p. e20872, XP055122659. ISSN: 1932-6203, DOI: 10.1371/ journal.pone. 0020872.
Gunasekaran, K et al., "Enhancing Antibody Fc Heterodimer Formation through Electrostatic Steering Effects: Applications to Bispecific Molecules and Monovalent IgG", Journal of Biological Chemistry, vol. 285, No. 25, Jun. 18, 2010, pp. 19637-19646, XP055001947, ISSN: 0021-9258, DOI: 10.1074/jbc.M110.117382.
Spasevska, I., "An outlook on bispecific antibodies: Methods of production and therapeutic benefits", Bio Sciences Master Reviews, Jan. 21, 2013, Xp055122817, Retrieved from the internet: URL:http://biologie.ens-lyon.fr/biologie/ressources/bibliographoes/pdf/m1-12-13-biosci-reviews-spasevska-i-2c-m.pdf?lang=en [retrieved on Jun. 11, 2014].
Lewis, S., et al., "Generation of bispecific IgG antibodies by structure-based design of an orthogonal Fab interface", Nature Biotechnology, vol. 32, No. 2, Feb. 1, 2014, pp. 191-198, XP055122831, ISSN: 1087-0156, DOI: 10.1038/nbt.2797PLOS ONE, vol. 6, No. 6, Jun. 17, 2011, p. e20872, XP055122659. ISSN: 1932-6203, DOI: 10.1371/ journal.pone. 0020872.
Document from WIPO Examination of related application: "International Search Report," Form PCT/ISA/210, Date of the actual completion of the International search: dated Jun. 11, 2014, Date of mailing of the International search report: dated Jul. 7, 2014.

(Continued)

*Primary Examiner* — Michael D Burkhart
(74) *Attorney, Agent, or Firm* — Xiaoguang Gao

(57) ABSTRACT

The present invention provides methods for producing Fabs and bi-specific antibodies comprising designed residues in the interfaces of the heavy chain-light chain variable ($V_H$/$V_L$) domain and the heavy chain-light chain constant ($C_{H1}$/$C_L$) domain, Fabs and bi-specific antibodies produced according to said processes and host cells encoding the same.

12 Claims, 3 Drawing Sheets

Specification includes a Sequence Listing.

(56) References Cited

OTHER PUBLICATIONS

Document from WIPO Examination of related application: "Written Opinion of the International Search Authority," Date of completion of this opinion as per Form PCT/ISA/210: Date of the actual completion of the International search: dated Jun. 11, 2014, Date of mailing of the International search report: dated Jul. 7, 2014.
Rudikoff, S. et al., "Single Amino Acid Substitution Altering Antigen-Binding Specificity" Proceedings of the National Academy of Sciences,National Academy of Sciences, US, vol. 79,Mar. 1982 (Mar. 1, 1982),pp. 1979-1983,XP007901436,ISSN: 0027-8424,DOI: 10.1073/PNAS.79.6 1979.
Zhenpingzhu,etal.,"Remodeling Domain Interfaces to Enhance Heterodimer Formation",Protein Science (1997),vol. 6,No. 4,Apr. 1, 1997 (Apr. 1, 1997),pp. 781-788,XP055345091,US,ISSN: 0961-8368, DOI: 10.1002/pro.5560060404.
Salfeld,Jochen G.,"Isotype Selection in Antibody Engineering",Nature Biotechnology, Nature Publishing Group,United States,vol. 25,No. 12,Dec. 1, 2007 (Dec. 1, 2007),oaaes 1369-1372,XP002668461,ISSN: 1546-1696,DOI: 10.1038/NBT1207-1369.
Kabat,et al.,"Sequences of Proteins of Immunological Interest" (1991),vol. I,5th ed., U.S. Department of Health and Human Services, Public Health Service National Institutes of Health, pp. xvi,103,310,647,653,663,671,680,689.
Tan, et al., "Contributions of a Highly Conserved VH/VL Hydrogen Bonding Interaction to scFv Folding Stability and Refolding Efficiency". Biophysical Journal, vol. 75, Sep. 1998, pp. 1473-1482.

\* cited by examiner

Figure 1. Schematic diagrams of IgG BsAb (A), Fab-Fab (B) and IgG-Fab(C) design formats. The "*" in the IgG BsAb diagram indicates a heterodimerized antibody CH3 domain

METHODS FOR PRODUCING FABS AND BI-SPECIFIC ANTIBODIES

Antibody therapies represent an ever increasing segment of the global pharmaceutical market. Approved antibody-based products include treatments for cancer, rheumatoid arthritis, infectious diseases, cardiovascular disease and autoimmune disorders. However, to improve patient outcomes, co-administration of two or more agents that perturb distinct therapeutic targets or biochemical pathways is often desired. In this context, antibody therapy has limitations.

Co-administration of two or more antibody therapies requires multiple injections or, alternatively, a single injection of a co-formulation of two different antibody compositions. While multiple injections permit flexibility in dose and timing of administration, the inconvenience and discomfort associated with multiple injections may reduce patient compliance. On the other hand, while a co-formulation of multiple antibody agents would permit fewer injections, the difficulty and/or expense associated with designing a suitable pharmaceutical formulation that provides the necessary stability and bioavailability, for each antibody ingredient, may be prohibitive. Furthermore, any treatment regime which entails administration of separate antibody agents will incur the added manufacturing and regulatory cost associated with the development of each individual agent.

The archetypical antibody is comprised of two identical antigen binding fragments (Fabs) which not only direct binding to a particular antigenic determinant, but also provide the interface for assembly between heavy chain (HC)-light chain (LC) pairs. Bispecific antibodies—single agents capable of binding to two distinct antigens—have been proposed as a means for addressing the limitations attendant with co-administration or co-formulation of separate antibody agents. Bispecific antibodies may integrate the binding activity of two separate MAb therapeutics, providing a cost and convenience benefit to the patient. Under certain circumstances, bispecific antibodies may elicit synergistic or novel activities beyond what an antibody-combination can achieve. One example of novel activity provided by bispecific antibodies would be the bridging of two different cell types through the binding of distinct cell surface receptors. Alternately, bispecific antibodies could cross-link two receptors on the surface of the same cell leading to novel agonistic/antagonistic mechanisms.

The ability to generate bispecific antibodies with fully IgG architecture has been a long-standing challenge in antibody engineering. One proposal for generating fully IgG bispecific antibodies entails co-expression of nucleic acids encoding two, distinct HC-LC pairs which, when expressed, assemble to form a single antibody comprising two distinct Fabs. However, challenges with this approach remain. Specifically, the expressed polypeptides of each desired Fab must assemble with good specificity to reduce generation of mis-matched byproducts, and the resulting heterotetramer must assemble with good stability. Procedures for directing assembly of particular HC-HC pairs by introducing modifications into regions of the HC-HC interface have been disclosed in the art. (See Klein et al., *mAbs;* 4(6); 1-11 (2012); Carter et al., *J. Immunol. Methods;* 248; 7-15 (2001); Gunasekaran, et al., *J. Biol. Chem.;* 285; 19637-19646 (2010); Zhu et al., *Protein Sci.;* 6: 781-788 (1997); and Igawa et al., *Protein Eng. Des. Sel.;* 23; 667-677 (2010)). However, there remains a need for alternative methods.

In accordance with the present invention, methods have been identified for achieving assembly of particular Fabs by co-expressing nucleic acids encoding particular HC-LC pairs which contain designed residues in the interface of the heavy chain-light chain variable ($V_H/V_L$) domains and the heavy chain-light chain constant ($C_{H1}/C_L$) domains. More particularly, the methods of the present invention achieve improved specificity and, or stability in assembly of particular Fabs. Even more particular, the methods of the present invention allow the binding specificities and binding activities of the variable regions of two distinct therapeutic antibodies to be combined in a single bi-specific antibody compound.

Thus, the present invention provides a method for producing a fragment, antigen binding (Fab) comprising: (1) co-expressing in a host cell: (a) a first nucleic acid encoding both a heavy chain variable domain and an IgG heavy chain constant CH1 domain, wherein said heavy chain variable domain comprises a lysine substituted at residue 39 (39K) and a glutamic acid substituted at the residue which is four amino acids upstream of the first residue of HFR3 according to Kabat, and said heavy chain CH1 domain comprises an alanine substituted at residue 172 (172A) and a glycine substituted at residue 174 (174G); and (b) a second nucleic acid encoding both a light chain variable domain and a light chain constant domain wherein said light chain variable domain is a kappa isotype and comprises an arginine substituted at residue 1 (1R) and an aspartic acid substituted at residue 38 (38D), and said light chain constant domain comprises a tyrosine substituted at residue 135 (135Y) and a tryptophan substituted at residue 176 (176W), wherein each of said heavy chain and light chain variable domains comprise three complementarity determining regions (CDRs) which direct binding to the same antigen; (2) cultivating said host cell under conditions such that said heavy chain variable and constant domains and said light chain variable and constant domains are produced; and (3) recovering from said host cell a Fab comprising said heavy chain variable and constant domains and said light chain variable and constant domains. More particular to this embodiment, the present invention provides a method comprising one or more of the following: said first nucleic acid encodes a heavy chain CH1 constant domain further comprising a methionine or isoleucine substituted at residue 190 (190M or 190I); said second nucleic acid encodes a light chain constant domain further comprising a leucine substituted at residue 133 (133L); and said second nucleic acid encodes a light chain constant domain further comprising a glutamine or aspartic acid substituted at residue 174 (174Q or 174D).

In a separate embodiment, the present invention provides a method for producing a fragment, antigen binding (Fab) comprising: (1) co-expressing in a host cell: (a) a first nucleic acid encoding both a heavy chain variable domain and an IgG heavy chain constant CH1 domain, wherein said heavy chain variable domain comprises a lysine substituted at residue 39 (39K) and a glutamic acid substituted at the residue which is four amino acids upstream of the first residue of HFR3 according to Kabat, and said heavy chain CH1 domain comprises an arginine substituted at residue 172 (172R) and a glycine substituted at residue 174 (174G); and (b) a second nucleic acid encoding both a light chain variable domain and a light chain constant domain wherein said light chain variable domain is a kappa isotype and comprises an arginine substituted at residue 1 (1R) and an aspartic acid substituted at residue 38 (38D), and said light chain constant domain comprises a tyrosine substituted at residue 135 (135Y) and a tryptophan substituted at residue 176 (176W), wherein each of said heavy chain and light chain variable domains comprise three complementarity determining regions (CDRs) which direct binding to the same antigen; (2) cultivating said host cell under conditions such that said heavy chain variable and constant domains and said light chain variable and constant domains are produced; and (3) recovering from said host cell a Fab comprising said heavy chain variable and constant domains and said light chain variable and constant domains. More particular to this embodiment, the present invention provides a method comprising one or more of the following: said first nucleic acid encodes a heavy chain CH1 constant domain further comprising a methionine or isoleucine substituted at residue 190 (190M or 190I); said second nucleic acid encodes a light chain constant domain further comprising a leucine substituted at residue 133 (133L); and said second nucleic acid encodes a light chain constant domain further comprising a glutamine or aspartic acid substituted at residue 174 (174Q or 174D).

In another embodiment, the present invention provides a method for producing a fragment, antigen binding (Fab) comprising: (1) co-expressing in a host cell: (a) a first nucleic acid encoding both a heavy chain variable domain and an IgG heavy chain constant CH1 domain, wherein said heavy chain variable domain comprises a lysine substituted at residue 39 (39K) and a glutamic acid substituted at the residue which is four amino acids upstream of the first residue of HFR3 according to Kabat, and said heavy chain CH1 domain comprises an alanine substituted at residue 172 (172A) and a glycine substituted at residue 174 (174G); and (b) a second nucleic acid encoding both a light chain variable domain and a light chain constant domain wherein said light chain variable domain is a kappa isotype and comprises an arginine substituted at residue 1 (1R) and an aspartic acid substituted at residue 38 (38D), and said light chain constant domain comprises a phenylalanine substituted at residue 135 (135F) and a tryptophan substituted at residue 176 (176W), wherein each of said heavy chain and light chain variable domains comprise three complementarity determining regions (CDRs) which direct binding to the same antigen; (2) cultivating said host cell under conditions such that said heavy chain variable and constant domains and said light chain variable and constant domains are produced; and (3) recovering from said host cell a Fab comprising said heavy chain variable and constant domains and said light chain variable and constant domains.

In another embodiment, the present invention provides a method for producing a fragment, antigen binding (Fab) comprising; (1) co-expressing in a host cell: (a) a first nucleic acid encoding both a heavy chain variable domain and an IgG heavy chain constant CH1 domain, wherein said heavy chain variable domain comprises a tyrosine substituted at residue 39 (39Y) and said heavy chain CH1 domain comprises a WT sequence; and (b) a second nucleic acid encoding both a light chain variable domain and a light chain constant domain wherein said light chain variable domain comprises an arginine substituted at residue 38 (38R) and said light chain constant domain comprises a WT sequence, wherein each of said heavy chain and light chain variable domains comprise three complementarity determining regions (CDRs) which direct binding to the same antigen; (2) cultivating said host cell under conditions such that said heavy chain variable and constant domains and said light chain variable and constant domains are produced; and (3) recovering from said host cell a Fab comprising said heavy chain variable and constant domains and said light chain variable and constant domains. More particular to this embodiment, the present invention provides a method comprising the following: said first nucleic acid encodes a heavy chain variable domain further comprising an arginine substituted at residue 105 (105R) and said second nucleic acid encodes a light chain variable domain further comprising an aspartic acid substituted at residue 42 (42D).

In a separate embodiment, the present invention provides a method for producing a fragment, antigen binding (Fab) comprising: (1) co-expressing in a host cell: (a) a first nucleic acid encoding both a heavy chain variable domain and an IgG heavy chain constant CH1 domain, wherein said heavy chain variable domain comprises a tyrosine substituted at residue 39 (39Y) and said heavy chain CH1 domain comprises an aspartic acid substituted at residue 228 (228D); and (b) a second nucleic acid encoding both a light chain variable domain and a light chain constant domain wherein said light chain variable domain comprises an arginine substituted at residue 38 (38R) and said light chain constant domain comprises a lysine substituted at residue 122 (122K), wherein each of said heavy chain and light chain variable domains comprise three complementarity determining regions (CDRs) which direct binding to the same antigen; (2) cultivating said host cell under conditions such that said heavy chain variable and constant domains and said light chain variable and constant domains are produced; and (3) recovering from said host cell a Fab comprising said heavy chain variable and constant domains and said light chain variable and constant domains. More particular to this embodiment, the present invention provides a method comprising the following: said first nucleic acid encodes a heavy chain variable domain further comprising an arginine substituted at residue 105 (105R) and said second nucleic acid encodes a light chain variable domain further comprising an aspartic acid substituted at residue 42 (42D).

The present invention also provides a method for producing a fragment, antigen binding (Fab) comprising: (1) co-expressing in a host cell: (a) a first nucleic acid encoding both a heavy chain variable domain and an IgG heavy chain constant CH1 domain, wherein said heavy chain variable domain comprises a lysine substituted at residue 39 (39K) and a glutamic acid substituted at the residue which is four amino acids upstream of the first residue of HFR3 according to Kabat, and said heavy chain CH1 domain comprises a WT sequence; and (b) a second nucleic acid encoding both a light chain variable domain and a light chain constant domain wherein said light chain variable domain is a kappa isotype and comprises an arginine substituted at residue 1 (1R) and an aspartic acid substituted at residue 38 (38D), and said light chain constant domain comprises a WT sequence, wherein each of said heavy chain and light chain variable domains comprise three complementarity determining regions (CDRs) which direct binding to the same antigen; (2) cultivating said host cell under conditions such that said heavy chain variable and constant domains and said light chain variable and constant domains are produced; and (3) recovering from said host cell a Fab comprising said heavy chain variable and constant domains and said light chain variable and constant domains.

More particularly, the present invention provides a method for producing a fragment, antigen binding (Fab) comprising: (1) co-expressing in a host cell: (a) a first nucleic acid encoding both a heavy chain variable domain and an IgG heavy chain constant CH1 domain, wherein said heavy chain variable domain comprises a lysine substituted at residue 39 (39K) and a glutamic acid substituted at the residue which is four amino acids upstream of the first residue of HFR3 according to Kabat, and said IgG heavy chain constant CH1 domain comprises an aspartic acid substituted at residue 228 (228D); and (b) a second nucleic acid encoding both a light chain variable domain and a light chain constant domain wherein said light chain variable domain is a kappa isotype and comprises an arginine substituted at residue 1 (1R) and an aspartic acid substituted at residue 38 (38D) and said light chain constant domain comprises a lysine substituted at residue 122 (122K), wherein each of said heavy chain and light chain variable domains comprise three complementarity determining regions (CDRs) which direct binding to the same antigen; (2) cultivating said host cell under conditions such that said heavy chain variable and constant domains and said light chain variable and constant domains are produced; and (3) recovering from said host cell a Fab comprising said heavy chain variable and constant domains and said light chain variable and constant domains.

The present invention also provides a method for producing a fragment, antigen binding (Fab) comprising: (1) co-expressing in a host cell: (a) a first nucleic acid encoding both a heavy chain variable domain and an IgG heavy chain constant CH1 domain, wherein said heavy chain variable domain comprises a tyrosine substituted at residue 39 (39Y) and said heavy chain CH1 domain comprises an alanine substituted at residue 172 (172A) and a glycine substituted at residue 174 (174G); and (b) a second nucleic acid encoding both a light chain variable domain and a light chain constant domain wherein said light chain variable domain comprises an arginine substituted at residue 38 (38R) and said light chain constant domain comprises a tyrosine substituted at residue 135 (135Y) and a tryptophan substituted at residue 176 (176W), wherein each of said heavy chain and light chain variable domains comprise three complementarity determining regions (CDRs) which direct binding to the same antigen; (2) cultivating said host cell under conditions such that said heavy chain variable and constant domains and said light chain variable and constant domains are produced; and (3) recovering from said host cell a Fab comprising said heavy chain variable and constant domains and said light chain variable and constant domains. More particular to this embodiment, the present invention provides a method comprising the following: said first nucleic acid encodes a heavy chain variable domain further comprising an arginine substituted at residue 105 (105R) and said second nucleic acid encodes a light chain variable domain further comprising an aspartic acid substituted at residue 42 (42D).

In a more particular embodiment, the present invention provides a method for producing a first and second fragment, antigen binding (Fab) comprising: (1) co-expressing in a host cell: (a) a first nucleic acid encoding both a first heavy chain variable domain and a first IgG heavy chain constant CH1 domain, wherein said first heavy chain variable domain comprises a lysine substituted at residue 39 (39K) and a glutamic acid substituted at the residue which is four amino acids upstream of the first residue of HFR3 according to Kabat, and said first IgG heavy chain constant CH1 domain comprises an alanine substituted at residue 172 (172A) and a glycine substituted at residue 174 (174G); (b) a second nucleic acid encoding both a first light chain variable domain and a first light chain constant domain, wherein said first light chain variable domain is a kappa isotype and comprises an arginine substituted at residue 1(1R) and an aspartic acid substituted at residue 38 (38D), and said first light chain constant domain comprises a tyrosine substituted at residue 135 (135Y) and a tryptophan substituted at residue 176 (176W); (c) a third nucleic acid encoding both a second heavy chain variable domain and a second IgG heavy chain constant CH1 domain, wherein said second heavy chain variable domain comprises a tyrosine substituted at residue 39 (39Y) and said second IgG heavy chain constant CH1 domain comprises a WT sequence; and (d) a fourth nucleic acid encoding both a second light chain variable domain and a second light chain constant domain, wherein said second light chain variable domain comprises an arginine substituted at residue 38 (38R) and said second light chain constant domain comprises a WT sequence, wherein each of said first heavy chain and light chain variable domains comprise three complementarity determining regions (CDRs) which direct binding to a first antigen and further wherein each of said second heavy chain and light chain variable domains comprise three complementarity determining regions (CDRs) which direct binding to a second antigen that differs from said first antigen; (2) cultivating said host cell under conditions such that said first and second heavy chain variable and IgG CH1 constant domains and said first and second light chain variable and constant domains are produced; and (3) recovering from said host cell a first and second Fab wherein said first Fab comprises said first heavy chain variable and constant domains and said first light chain variable and constant domains, and said second Fab comprises said second heavy chain variable and constant domains and said second light chain variable and constant domains. More particular to this embodiment, the present invention provides a method comprising one or more of the following: said first nucleic acid encodes a heavy chain CH1 constant domain further comprising a methionine or isoleucine substituted at residue 190 (190M or 190I); said second nucleic acid encodes a light chain constant domain further comprising an leucine substituted at residue 133 (133L); said second nucleic acid encodes a light chain constant domain further comprising a glutamine or aspartic acid substituted at residue 174 (174Q or 174D), and said third nucleic acid encodes a heavy chain variable domain further comprising an arginine substituted at residue 105 (105R) with said fourth nucleic acid encoding a light chain variable domain further comprising an aspartic acid substituted at residue 42 (42D).

In a further embodiment, the present invention provides a method for producing a first and second fragment, antigen binding (Fab) comprising: (1) co-expressing in a host cell: (a) a first nucleic acid encoding both a first heavy chain variable domain and a first IgG heavy chain constant CH1 domain, wherein said first heavy chain variable domain comprises a lysine substituted at residue 39 (39K) and a glutamic acid substituted at the residue which is four amino acids upstream of the first residue of HFR3 according to Kabat, and said first IgG heavy chain constant CH1 domain comprises an arginine substituted at residue 172 (172R) and a glycine substituted at residue 174 (174G); (b) a second nucleic acid encoding both a first light chain variable domain and a first light chain constant domain, wherein said first light chain variable domain is a kappa isotype and comprises an arginine substituted at residue 1 (1R) and, an aspartic acid substituted at residue 38 (38D), and said first light chain constant domain comprises a tyrosine substituted at residue 135 (135Y) and a tryptophan substituted at residue 176 (176W); (c) a third nucleic acid encoding both a second heavy chain variable domain and a second IgG heavy chain constant CH1 domain, wherein said second heavy chain variable domain comprises a tyrosine substituted at residue 39 (39Y) and said second IgG heavy chain constant CH1 domain comprises a WT sequence; and (d) a fourth nucleic acid encoding both a second light chain variable domain and a second light chain constant domain, wherein said second light chain variable domain comprises an arginine substituted at residue 38 (38R) and said second light chain constant domain comprises a WT sequence, wherein each of said first heavy chain and light chain variable domains comprise three complementarity determining regions (CDRs) which direct binding to a first antigen and further wherein each of said second heavy chain and light chain variable domains comprise three complementarity determining regions (CDRs) which direct binding to a second antigen that differs from said first antigen; (2) cultivating said host cell under conditions such that said first and second heavy chain variable and IgG CH1 constant domains and said first and second light chain variable and constant domains are produced; and (3) recovering from said host cell a first and second Fab wherein said first Fab comprises said first heavy chain variable and constant domains and said first light chain variable and constant domains, and said second Fab comprises said second heavy chain variable and constant domains and said second light chain variable and constant domains. More particular to this embodiment, the present invention provides a method comprising one or more of the following: said first nucleic acid encodes a heavy chain all constant domain further comprising a methionine or isoleucine substituted at residue 190 (190M or 190I); said second nucleic acid encodes a light chain constant domain further comprising a leucine substituted at residue 133 (133L); said second nucleic acid encodes a light chain constant domain further comprising a glutamine or aspartic acid substituted at residue 174 (174Q or 174D), and said third nucleic acid encodes a heavy chain variable domain further comprising an arginine substituted at residue 105 (105R) with said fourth nucleic acid encoding a light chain variable domain further comprising an aspartic acid substituted at residue 42 (42D).

In a separate embodiment, the present invention provides A method for producing a first and second fragment, antigen binding (Fab) comprising: (1) co-expressing in a host cell: (a) a first nucleic acid encoding both a first heavy chain variable domain and a first IgG heavy chain constant CH1 domain, wherein said first heavy chain variable domain comprises a lysine substituted at residue 39 (39K) and a glutamic acid substituted at the residue which is four amino acids upstream of the first residue of HFR3 according to Kabat, and said first IgG heavy chain constant CH1 domain comprises an alanine substituted at residue 172 (172A) and a glycine substituted at residue 174 (174G); (b) a second nucleic acid encoding both a first light chain variable domain and a first light chain constant domain, wherein said first light chain variable domain is a kappa isotype and comprises an arginine substituted at residue 1 (1R) and an aspartic acid substituted at residue 38 (38D), and said first light chain constant domain comprises a tyrosine substituted at residue 135 (135Y) and a tryptophan substituted at residue 176 (176W); (c) a third nucleic acid encoding both a second heavy chain variable domain and a second IgG heavy chain constant CH1 domain, wherein said second heavy chain variable domain comprises a tyrosine substituted at residue 39 (39Y) and said second IgG heavy chain constant CH1 domain comprises an aspartic acid substituted at residue 228 (228D); and (d) a fourth nucleic acid encoding both a second light chain variable domain and a second light chain constant domain, wherein said second light chain variable domain comprises an arginine substituted at residue 38 (38R) and said second light chain constant domain comprises a lysine substituted at residue 122 (122K), wherein each of said first heavy chain and light chain variable domains comprise three complementarity determining regions (CDRs) which direct binding to a first antigen and further wherein each of said second heavy chain and light chain variable domains comprise three complementarity determining regions (CDRs) which direct binding to a second antigen that differs from said first antigen; (2) cultivating said host cell under conditions such that said first and second heavy chain variable and IgG CH1 constant domains and said first and second light chain variable and constant domains are produced; and (3) recovering from said host cell a first and second Fab wherein said first Fab comprises said first heavy chain variable and constant domains and said first light chain variable and constant domains, and said second Fab comprises said second heavy chain variable and constant domains and said second light chain variable and constant domains. More particular to this embodiment, the present invention provides a method comprising one or more of the following: said first nucleic acid encodes a heavy chain CH1 constant domain further comprising a methionine or isoleucine substituted at residue 190 (190M or 190I); said second nucleic acid encodes a light chain constant domain further comprising a leucine substituted at residue 133 (133L); said second nucleic acid encodes a light chain constant domain further comprising a glutamine or aspartic acid substituted at residue 174 (174Q or 174D), and said third nucleic acid encodes a heavy chain variable domain further comprising an arginic substituted at residue 105 (105R) with said fourth nucleic acid encoding a light chain variable domain further comprising an aspartic acid substituted at residue 42 (42D).

In another embodiment, the present invention provides a method for producing a first and second fragment, antigen binding (Fab) comprising: (1) co-expressing in a host cell: (a) a first nucleic acid encoding both a first heavy chain variable domain and a first IgG heavy chain constant CH1 domain, wherein said first heavy chain variable domain comprises a lysine substituted at residue 39 (39K) and a glutamic acid substituted at the residue which is four amino acids upstream of the first residue of HFR3 according to Kabat, and said first IgG heavy chain constant CH1 domain comprises an arginine substituted at residue 172 (172R) and a glycine substituted at residue 174 (174G); (b) a second nucleic acid encoding both a first light chain variable domain and a first light chain constant domain, wherein said first light chain variable domain is a kappa isotype and comprises an arginine substituted at residue 1 (1R) and an aspartic acid substituted at residue 38 (38D), and said first light chain constant domain comprises a tyrosine substituted at residue 135 (135Y) and a tryptophan substituted at residue 176 (176W); (c) a third nucleic acid encoding both a second heavy chain variable domain and a second IgG heavy chain constant CH1 domain, wherein said second heavy chain variable domain comprises a tyrosine substituted al residue 39 (39Y) and said second IgG heavy chain constant CH1 domain comprises an aspartic acid substituted at residue 228 (228D); and (d) a fourth nucleic acid encoding both a second light chain variable domain and a second light chain constant domain, wherein said second light chain variable domain comprises an arginine substituted at residue 38 (38R) and said second light chain constant domain comprises a lysine substituted at residue 122 (122K), wherein each of said first heavy chain and light chain variable domains comprise three complementarity determining regions (CDRs) which direct binding to a first antigen and further wherein each of said second heavy chain and light chain variable domains comprise three complementarity determining regions (CDRs) which direct binding to a second antigen that differs from said first antigen; (2) cultivating said host cell under conditions such that said first and second heavy chain variable and IgG CH1 constant domains and said first and second light chain variable and constant domains are produced; and (3) recovering from said host cell a first and second Fab wherein said first Fab comprises said first heavy chain variable and constant domains and said first light chain variable and constant domains, and said second Fab comprises said second heavy chain variable and constant domains and said second light chain variable and constant domains. More particular to this embodiment, the present invention provides a method comprising one or more of the following: said first nucleic acid encodes a heavy chain CH1 constant domain further comprising a methionine or isoleucine substituted at residue 190 (190M or 190I); said second nucleic acid encodes a light chain constant domain further comprising a leucine substituted at residue 133 (133L); said second nucleic acid encodes a light chain constant domain further comprising a glutamine or aspartic acid substituted at residue 174 (174Q or 174D), and said third nucleic acid encodes a heavy chain variable domain further comprising an arginic substituted at residue 105 (105R) with said fourth nucleic acid encoding a light chain variable domain further comprising an aspartic acid substituted at residue 42 (42D).

In another particular embodiment, the present invention provides a method for producing a first and second fragment, antigen binding (Fab) comprising: (1) co-expressing in a host cell: (a) a first nucleic acid encoding both a first heavy chain variable domain and a first IgG heavy chain constant CH1 domain, wherein said first heavy chain variable domain comprises a lysine substituted at residue 39 (39K) and a glutamic acid substituted at the residue which is four amino acids upstream of the first residue of HFR3 according to Kabat, and said first IgG heavy chain constant CH1 domain comprises an alanine substituted at residue 172 (172A) and a glycine substituted at residue 174 (174G); (b) a second nucleic acid encoding both a first light chain variable domain and a first light chain constant domain, wherein said first light chain variable domain is a kappa isotype and comprises an arginine substituted at residue 1(1R) and an aspartic acid substituted at residue 38 (38D), and said first light chain constant domain comprises a phenylalanine substituted at residue 135 (135F) and a tryptophan substituted at residue 176 (176W); (c) a third nucleic acid encoding both a second heavy chain variable domain and a second IgG heavy chain constant CH1 domain, wherein said second heavy chain variable domain comprises a tyrosine substituted at residue 39 (39Y) and said second IgG heavy chain constant CH1 domain comprises a WT sequence; and (d) a fourth nucleic acid encoding both a second light chain variable domain and a second light chain constant domain, wherein said second light chain variable domain comprises an arginine substituted at residue 38 (38R) and said second light chain constant domain comprises a WT sequence, wherein each of said first heavy chain and light chain variable domains comprise three complementarity determining regions (CDRs) which direct binding to a first antigen and further wherein each of said second heavy chain and light chain variable domains comprise three complementarity determining regions (CDRs) which direct binding to a second antigen that differs from said first antigen; (2) cultivating said host cell under conditions such that said first and second heavy chain variable and IgG CH1 constant domains and said first and second light chain variable and constant domains are produced; and (3) recovering from said host cell a first and second Fab wherein said first Fab comprises said first heavy chain variable and constant domains and said first light chain variable and constant domains, and said second Fab comprises said second heavy chain variable and constant domains and said second light chain variable and constant domains.

The present invention also provides a method for producing a first and second fragment, antigen binding (Fab) comprising: (1) co-expressing in a host cell: (a) a first nucleic acid encoding both a first heavy chain variable domain and a first IgG heavy chain constant CH1 domain, wherein said first heavy chain variable domain comprises a tyrosine substituted at residue 39 (39Y), and said first IgG heavy chain constant all domain comprises an alanine substituted at residue 172 (172A) and a glycine substituted at residue 174 (174G); (b) a second nucleic acid encoding both a first light chain variable domain and a first light chain constant domain, wherein said first light chain variable domain comprises an arginine substituted at residue 38 (38R), and said first light chain constant domain comprises a tyrosine substituted at residue 135 (135Y) and a tryptophan substituted at residue 176 (176W); (c) a third nucleic acid encoding both a second heavy chain variable domain and a second IgG heavy chain constant CH1 domain, wherein said second heavy chain variable domain comprises a lysine substituted at residue 39 (39K) and a glutamic acid substituted at the residue which is four amino acids upstream of the first residue of HFR3 according to Kabat and said second IgG heavy chain constant CH1 domain comprises a WT sequence; and (d) a fourth nucleic acid encoding both a second light chain variable domain and a second light chain constant domain, wherein said light chain variable domain is a kappa isotype and comprises an arginine substituted at residue 1 (1R) and an aspartic acid substituted at residue 38 (38D) and said second light chain constant domain comprises a WT sequence, wherein each of said first heavy chain and light chain variable domains comprise three complementarity determining regions (CDRs) which direct binding to a first antigen and further wherein each of said second heavy chain and light chain variable domains comprise three complementarity determining regions (CDRs) which direct binding to a second antigen that differs from said first antigen; (2) cultivating said host cell under conditions such that said first and second heavy chain variable and IgG CH1 constant domains and said first and second light chain variable and constant domains are produced; and (3) recovering from said host cell a first and second Fab wherein said first Fab comprises said first heavy chain variable and constant domains and said first light chain variable and constant domains, and said second Fab comprises said second heavy chain variable and constant domains and said second light chain variable and constant domains. More particular to this embodiment, the present invention provides a method comprising the following: said first nucleic acid encodes a heavy chain variable domain further comprising an arginine substituted at residue 105 (105R) and said second nucleic acid encodes a light chain variable domain further comprising an aspartic acid substituted at residue 42 (42D).

In another embodiment, the present invention provides a method for producing a first and second fragment, antigen binding (Fab) comprising: (1) co-expressing in a host cell: (a) a first nucleic acid encoding both a first heavy chain variable domain and a first IgG heavy chain constant CH1 domain, wherein said first heavy chain variable domain comprises a tyrosine substituted at residue 39 (39Y), and said first IgG heavy chain constant CH1 domain comprises an alanine substituted at residue 172 (172A) and a glycine substituted at residue 174 (174G); (b) a second nucleic acid encoding both a first light chain variable domain and a first light chain constant domain, wherein said first light chain variable domain comprises an arginine substituted at residue 38 (38R), and said first light chain constant domain comprises a tyrosine substituted at residue 135 (135Y) and a tryptophan substituted at residue 176 (176W); (c) a third nucleic acid encoding both a second heavy chain variable domain and a second IgG heavy chain constant CH1 domain, wherein said second heavy chain variable domain comprises a lysine substituted at residue 39 (39K) and a glutamic acid substituted at the residue which is four amino acids upstream of the first residue of HFR3 according to Kabat and said second IgG heavy chain constant CH1 domain comprises an aspartic acid substituted at residue 228 (228D); and (d) a fourth nucleic acid encoding both a second light chain variable domain and a second light chain constant domain, wherein said light chain variable domain is a kappa isotype and comprises an arginine substituted at residue 1 (1R) and an aspartic acid substituted at residue 38 (38D) and said second light chain constant domain comprises a lysine substituted at residue 122 (122K), wherein each of said first heavy chain and light chain variable domains comprise three complementarity determining regions (CDRs) which direct binding to a first antigen and further wherein each of said second heavy chain and light chain variable domains comprise three complementarity determining regions (CDRs) which direct binding to a second antigen that differs from said first antigen; (2) cultivating said host cell under conditions such that said first and second heavy chain variable and IgG CH1 constant domains and said first and second light chain variable and constant domains are produced; and (3) recovering from said host cell a first and second Fab wherein said first Fab comprises said first heavy chain variable and constant domains and said first light chain variable and constant domains, and said second Fab comprises said second heavy chain variable and constant domains and said second light chain variable and constant domains. More particular to this embodiment, the present invention provides a method comprising the following; said first nucleic acid encodes a heavy chain variable domain further comprising an arginine substituted at residue 105 (105R) and said second nucleic acid encodes a light chain variable domain further comprising an aspartic acid substituted at residue 42 (42D).

The present invention also provides a method for producing a bispecific antibody comprising: (1) co-expressing in a host cell: (a) a first nucleic acid encoding a first IgG heavy chain, wherein said first heavy chain comprises a variable domain comprising a lysine substituted at residue 39 (39K) and a glutamic acid substituted at the residue which is four amino acids upstream of the first residue of HFR3 according to Kabat, and a CH1 constant domain comprising an alanine substituted at residue 172 (172A) and a glycine substituted at residue 174 (174G); (b) a second nucleic acid encoding a first light chain, wherein said first light chain comprises a kappa variable domain comprising an arginine substituted at residue 1(1R) and an aspartic acid substituted at residue 38 (38D), and a constant domain comprising a tyrosine substituted at residue 135 (135Y) and a tryptophan substituted at residue 176 (176W); (c) a third nucleic acid encoding a second IgG heavy chain, wherein said second heavy chain comprises a variable domain comprising a tyrosine substituted at residue 39 (39Y), and a CH1 constant domain comprising a WT sequence; and (d) a fourth nucleic acid encoding a second light chain, wherein said second light chain comprises a variable domain comprising an arginine substituted at residue 38 (38R) and a constant domain comprising a WT sequence, wherein each of said first heavy chain and light chain variable domains comprise three complementarity determining regions (CDRs) which direct binding to a first antigen and further wherein each of said second heavy chain and light chain variable domains comprise three complementarity determining regions (CDRs) which direct binding to a second antigen that differs from said first antigen; (2) cultivating said host cell under conditions such that said first and second IgG heavy chains and said first and second light chains are produced; and (3) recovering from said host cell a bispecific antibody comprising a first and second fragment, antigen binding (Fab) wherein said first Fab comprises said first IgG heavy chain and said first light chain and said second Fab comprises said second IgG heavy chain and said second light chain. More particular to this embodiment, the present invention provides a method comprising one or more of the following: said first nucleic acid encodes a heavy chain CH1 constant domain further comprising a methionine or isoleucine substituted at residue 190 (190M or 190I); said second nucleic acid encodes a light chain constant domain further comprising a leucine substituted at residue 133 (133L); said second nucleic acid encodes a light chain constant domain further comprising a glutamine or aspartic acid substituted at residue 174 (174Q or 174D), and said third nucleic acid encodes a heavy chain variable domain further comprising an arginine substituted at residue 105 (105R) with said fourth nucleic acid encoding a light chain variable domain further comprising an aspartic acid substituted at residue 42 (42D).

In a separate embodiment, the present invention provides a method for producing a bispecific antibody comprising: (1) co-expressing in a host cell: (a) a first nucleic acid encoding a first IgG heavy chain, wherein said first heavy chain comprises a variable domain comprising a lysine substituted at residue 39 (39K) and a glutamic acid substituted at the residue which is 4 amino acids upstream of the first residue of HFR3 according to Kabat, and a CH1 constant domain comprising an arginine substituted at residue 172 (172R) and a glycine substituted at residue 174 (174G); (b) a second nucleic acid encoding a first light chain, wherein said first light chain comprises a kappa variable domain comprising an arginine substituted at residue 1 (1R) and an aspartic acid substituted at residue 38 (38D), and a constant domain comprising a tyrosine substituted at residue 135 (135Y) and a tryptophan substituted at residue 176 (176W); (c) a third nucleic acid encoding a second IgG heavy chain, wherein said second heavy chain comprises a variable domain comprising a tyrosine substituted at residue 39 (39Y), and a CH1 constant domain comprising a WT sequence; and (d) a fourth nucleic acid encoding a second light chain, wherein said second light chain comprises a variable domain comprising an arginine substituted at residue 38 (38R) and a constant domain comprising a WT sequence, wherein each of said first heavy chain and light chain variable domains comprise three complementarity determining regions (CDRs) which direct binding to a first antigen and further wherein each of said second heavy chain and light chain variable domains comprise three complementarity determining regions (CDRs) which direct binding to a second antigen that differs from said first antigen; (2) cultivating said host cell under conditions such that said first and second IgG heavy chains and said first and second light chains are produced; and (3) recovering from said host cell a bispecific antibody comprising a first and second fragment, antigen binding (Fab) wherein said first Fab comprises said first IgG heavy chain and said first light chain and said second Fab comprises said second IgG heavy chain and said second light chain. More particular to this embodiment, the present invention provides a method comprising one or more of the following: said first nucleic acid encodes a heavy chain CH1 constant domain further comprising a methionine or isoleucine substituted at residue 190 (190M or 190I); said second nucleic acid encodes a light chain constant domain further comprising a leucine substituted at residue 133 (133L); said second nucleic acid encodes a light chain constant domain further comprising a glutamine or aspartic acid substituted at residue 174 (174Q or 174D), and said third nucleic acid encodes a heavy chain variable domain further comprising an arginine substituted at residue 105 (105R) with said fourth nucleic acid encoding a light chain variable domain further comprising an aspartic acid substituted at residue 42 (42D).

In yet another embodiment, the present invention provides a method for producing a bispecific antibody comprising: (1) co-expressing in a host cell: (a) a first nucleic acid encoding a first IgG heavy chain, wherein said first heavy chain comprises a variable domain comprising a lysine substituted at residue 39 (39K) and a glutamic acid substituted at the residue which is four amino acids upstream of the first residue of HFR3 according to Kabat, and a CH1 constant domain comprising an alanine substituted at residue 172 (172A) and a glycine substituted at residue 174 (174G); (b) a second nucleic acid encoding a first light chain, wherein said first light chain comprises a kappa variable domain comprising an arginine substituted at residue 1 (1R) and an aspartic acid substituted at residue 38 (38D), and a constant domain comprising a tyrosine substituted at residue 135 (135Y) and a tryptophan substituted at residue 176 (176W); (c) a third nucleic acid encoding a second IgG heavy chain, wherein said second heavy chain comprises a variable domain comprising a tyrosine substituted at residue 39 (39Y), and a CH1 constant domain comprising an aspartic acid substituted at residue 228 (228D); and (d) a fourth nucleic acid encoding a second light chain, wherein said second light chain comprises a variable domain comprising an arginine substituted at residue 38 (38R) and a constant domain comprising a lysine substituted at residue 122 (122K), wherein each of said first heavy chain and light chain variable domains comprise three complementarity determining regions (CDRs) which direct binding to a first antigen and further wherein each of said second heavy chain and light chain variable domains comprise three complementarity determining regions (CDRs) which direct binding to a second antigen that differs from said first antigen; (2) cultivating said host cell under conditions such that said first and second IgG heavy chains and said first and second light chains are produced; and (3) recovering from said host cell a bispecific antibody comprising a first and second fragment, antigen binding (Fab) wherein said first Fab comprises said first IgG heavy chain and said first light chain and said second Fab comprises said second IgG heavy chain and said second light chain. More particular to this embodiment, the present invention provides a method comprising one or more of the following: said first nucleic acid encodes a heavy chain CH1 constant domain further comprising a methionine or isoleucine substituted at residue 190 (190M or 190I); said second nucleic acid encodes a light chain constant domain further comprising a leucine substituted at residue 133 (133L); said second nucleic acid encodes a light chain constant domain further comprising a glutamine or aspartic acid substituted at residue 174 (174Q or 174D), and said third nucleic acid encodes a heavy chain variable domain further comprising an arginine substituted at residue 105 (105R) with said fourth nucleic acid encoding a light chain variable domain further comprising an aspartic acid substituted at residue 42 (42D).

In another embodiment, the present invention provides a method for producing a bispecific antibody comprising: (1) co-expressing in a host cell: (a) a first nucleic acid encoding a first IgG heavy chain, wherein said first heavy chain comprises a variable domain comprising a lysine substituted at residue 39 (39K) and a glutamic acid substituted at the residue which is four amino acids upstream of the first residue of HFR3 according to Kabat, and a CH1 constant domain comprising an arginine substituted at residue 172 (172R) and a glycine substituted at residue 174 (174G); (b) a second nucleic acid encoding a first light chain, wherein said first light chain comprises a kappa variable domain comprising an arginine substituted at residue 1 (1R) and an aspartic acid substituted at residue 38 (38D), and a constant domain comprising a tyrosine substituted at residue 135 (135Y) and a tryptophan substituted at residue 176 (176W); (c) a third nucleic acid encoding a second IgG heavy chain, wherein said second heavy chain comprises a variable domain comprising a tyrosine substituted at residue 39 (39Y), and a CH1 constant domain comprising an aspartic acid substituted at residue 228 (228D); and (d) a fourth nucleic acid encoding a second light chain, wherein said second light chain comprises a variable domain comprising an arginine substituted at residue 38 (38R) and a constant domain comprising a lysine substituted at residue 122 (122K), wherein each of said first heavy chain and light chain variable domains comprise three complementarity determining regions (CDRs) which direct binding to a first antigen and further wherein each of said second heavy chain and light chain variable domains comprise three complementarity determining regions (CDRs) which direct binding to a second antigen that differs from said first antigen; (2) cultivating said host cell under conditions such that said first and second IgG heavy chains and said first and second light chains are produced; and (3) recovering from said host cell a bispecific antibody comprising a first and second fragment, antigen binding (Fab) wherein said first Fab comprises said first IgG heavy chain and said first light chain and said second Fab comprises said second IgG heavy chain and said second light chain. More particular to this embodiment, the present invention provides a method comprising one or more of the following: said first nucleic acid encodes a heavy chain CH1 constant domain further comprising a methionine or isoleucine substituted at residue 190 (190M or 190I); said second nucleic acid encodes a light chain constant domain further comprising a leucine substituted at residue 133 (133L); said second nucleic acid encodes a light chain constant domain further comprising a glutamine or aspartic acid substituted at residue 174 (174Q or 174D), and said third nucleic acid encodes a heavy chain variable domain further comprising an arginine substituted at residue 105 (105R) with said fourth nucleic acid encoding a light chain variable domain further comprising an aspartic acid substituted at residue 42 (42D).

The present invention also provides a method for producing a bispecific antibody comprising: (1) co-expressing in a host cell: (a) a first nucleic acid encoding a first IgG heavy chain, wherein said first heavy chain comprises a variable domain comprising a tyrosine substituted at residue 39 (39Y), and a CH1 constant domain comprising an alanine substituted at residue 172 (172A) and a glycine substituted at residue 174 (174G); (b) a second nucleic acid encoding a first light chain, wherein said first light chain comprises a variable domain comprising an arginine substituted at residue 38 (38R), and a constant domain comprising a tyrosine substituted at residue 135 (135Y) and a tryptophan substituted at residue 176 (176W); (c) a third nucleic acid encoding a second IgG heavy chain, wherein said heavy chain comprises a variable domain comprising a lysine substituted at residue 39 (39K) and a glutamic acid substituted at the residue which is four amino acids upstream of the first residue of HFR3 according to Kabat and a constant domain comprising a WT sequence: and (d) a fourth nucleic acid encoding second light chain, wherein said second light chain comprises a kappa variable domain comprising an arginine substituted at residue 1 (1R) and an aspartic acid substituted at residue 38 (38D), and a constant domain comprising a WT sequence, wherein each of said first heavy chain and light chain variable domains comprise three complementarity determining regions (CDRs) which direct binding to a first antigen and further wherein each of said second heavy chain and light chain variable domains comprise three complementarity determining regions (CDRs) which direct binding to a second antigen that differs from said first antigen; (2) cultivating said host cell under conditions such that said first and second IgG heavy chains and said first and second light chains are produced; and (3) recovering from said host cell a bispecific antibody comprising a first and second fragment, antigen binding (Fab) wherein said first Fab comprises said first IgG heavy chain and said first light chain and said second Fab comprises said second IgG heavy chain and said second light chain. More particular to this embodiment, the present invention provides a method comprising the following: said first nucleic acid encodes a heavy chain variable domain further comprising an arginine substituted at residue 105 (105R) and said second nucleic acid encodes a light chain variable domain further comprising an aspartic acid substituted at residue 42 (42D).

The present invention also provides a method for producing a bispecific antibody comprising: (1) co-expressing in a host cell: (a) a first nucleic acid encoding a first IgG heavy chain, wherein said, first heavy chain comprises a variable domain comprising a tyrosine substituted at residue 39(39Y), and a CH1 constant domain comprising an alanine substituted at residue 172 (172A) and a glycine substituted at residue 174 (174G); (b) a second nucleic acid encoding a first light chain, wherein said first light chain comprises a variable domain comprising an arginine substituted at residue 38 (38R), and a constant domain comprising a tyrosine substituted at residue 135 (135Y) and a tryptophan substituted at residue 176 (I76W); (c) a third nucleic acid encoding a second IgG heavy chain, wherein said heavy chain comprises a variable domain comprising a lysine substituted at residue 39 (39K) and a glutamic acid substituted at the residue which is four amino acids upstream of the first residue of HFR3 according to Kabat and a constant domain comprising an aspartic acid substituted at residue 228 (228D); and (d) a fourth nucleic acid encoding second light chain, wherein said second light chain comprises a kappa variable domain comprising an arginine substituted at residue 1 (1R) and an aspartic acid substituted at residue 38 (38D), and a constant domain comprising a lysine substituted at residue 122 (122K), wherein each of said first heavy chain and light chain variable domains comprise three complementarity determining regions (CDRs) which direct binding to a first antigen and further wherein each of said second heavy chain and light chain variable domain's comprise three complementarity determining regions (CDRs) which direct binding to a second antigen that differs from said first antigen; (2) cultivating said host cell under conditions such that said first and second IgG heavy chains and said first and second light chains are produced; and (3) recovering from said host cell a bispecific antibody comprising a first and second fragment, antigen binding (Fab) wherein said first Fab comprises said first IgG heavy chain and said first light chain and said second Fab comprises said second IgG heavy chain and said second light chain. More particular to this embodiment, the present invention provides a method comprising the following: said first nucleic acid encodes a heavy chain variable domain further comprising an arginine substituted at residue 105 (105R) and said second nucleic acid encodes a light chain variable domain further comprising an aspartic acid substituted at residue 42 (42D).

As a further particular embodiment to the methods for producing a bispecific antibody, as provided herein, the present invention provides a method wherein one of said first and second IgG heavy chains further comprises a CH3 constant domain comprising a lysine substituted at residue 356 and a lysine substituted at residue 399, and the other of said first and second IgG heavy chains further comprises a CH3 constant domain comprising an aspartic acid substituted at residue 392 and an aspartic acid substituted at residue 409.

Even more particularly, the present invention provides a method for producing a bispecific antibody comprising: (1) co-expressing in a host cell: (a) a first nucleic acid encoding a first IgG heavy chain, wherein said first heavy chain comprises a variable domain comprising a lysine substituted at residue 39 (39K) and a glutamic acid substituted at the residue which is four amino acids upstream of the first residue of HFR3 according to Kabat, a CH1 constant domain comprising an alanine substituted at residue 172 (172A) and a glycine substituted at residue 174 (174G) and a CH3 constant domain comprising a lysine substituted at residue 356 (356K) and a lysine substituted at residue 399 (399K); (b) a second nucleic acid encoding a first light chain, wherein said first light chain comprises a kappa variable domain comprising an arginine substituted at residue 1 (1R) and an aspartic acid substituted at residue 38 (38D), and a constant domain comprising a tyrosine substituted at residue 135 (135Y) and a tryptophan substituted at residue 176 (176W); (c) a third nucleic acid encoding a second IgG heavy chain, wherein said second heavy chain comprises a variable domain comprising a tyrosine substituted at residue 39 (39Y), a CH1 constant domain comprising a WT sequence and a CH3 constant domain comprising an aspartic acid substituted at residue 392 (392D) and an aspartic acid substituted at residue 409 (409D); and (d) a fourth nucleic acid encoding a second light chain, wherein said second light chain comprises, a variable domain comprising an arginine substituted at residue 38 (38R) and a constant domain comprising a WT sequence, wherein each of said first heavy chain and light chain variable domains comprise three complementarity determining regions (CDRs) which direct binding to a first antigen and further wherein each of said second heavy chain and light chain variable domains comprise three complementarity determining regions (CDRs) which direct binding to a second antigen that differs from said first antigen; (2) cultivating said host cell under conditions such that said first and second IgG heavy chains and said first and second light chains are produced; and (3) recovering from said host cell a bispecific antibody comprising a first and second fragment, antigen binding (Fab) wherein said first Fab comprises said first IgG heavy chain and said first light chain and said second Fab comprises said second IgG heavy chain and said second light chain.

In other particular embodiments, the host cell for use in the methods of the present invention is a mammalian cell, more particularly a HEK293 or CHO cell, and the IgG heavy chain constant domain produced by the methods of the present invention is IgG1 or IgG4 isotype, and more particularly IgG1.

The present invention also provides Fabs, bi-specific antibodies and bi-specific antigen binding compounds, each produced according to the methods of the present invention, as well as host cells comprising nucleic acids encoding the same. In particular, the present invention provides any of the Fabs, bispecific antibodies, nucleic acids or host cells as exemplified in any of the Examples herein.

In another particular embodiment, the present invention provides a bispecific antibody comprising a first IgG heavy chain, wherein said first heavy chain comprises a variable domain comprising a lysine substituted at residue 39 (39K) and a glutamic acid substituted at the residue which is four amino acids upstream of the lust residue of HFR3 according to Kabat, a CH1 constant domain comprising an alanine substituted at residue 172 (172A) and a glycine substituted at residue 174 (174G) and a CH3 constant domain comprising a lysine substituted at residue 356 (356K) and a lysine substituted at residue 399 (399K); (b) a first light chain, wherein said first light chain comprises a kappa variable domain comprising an arginine substituted at residue 1 (1R) and an aspartic acid substituted at residue 38 (38D), and a constant domain comprising a tyrosine substituted at residue 135 (135Y) and a tryptophan substituted at residue 176 (176W); (c) a second IgG heavy chain, wherein said second heavy chain comprises a variable domain comprising a tyrosine substituted at residue 39 (39Y), a CH1 constant domain comprising a WT sequence and a CH3 constant domain comprising an aspartic acid substituted at residue 392 (392D) and an aspartic acid substituted at residue 409 (409D); and (d) a second light chain, wherein said second light chain comprises a variable domain comprising an arginine substituted at residue 38 (38R) and a constant domain comprising a WT sequence, wherein each of said first heavy chain and light chain variable domains comprise three complementarity determining regions (CDRs) which direct binding to a first antigen and further wherein each of said second heavy chain and light chain variable domains comprise three complementarity determining regions (CDRs) which direct binding to a second antigen that differs from said first antigen.

Figure 1:
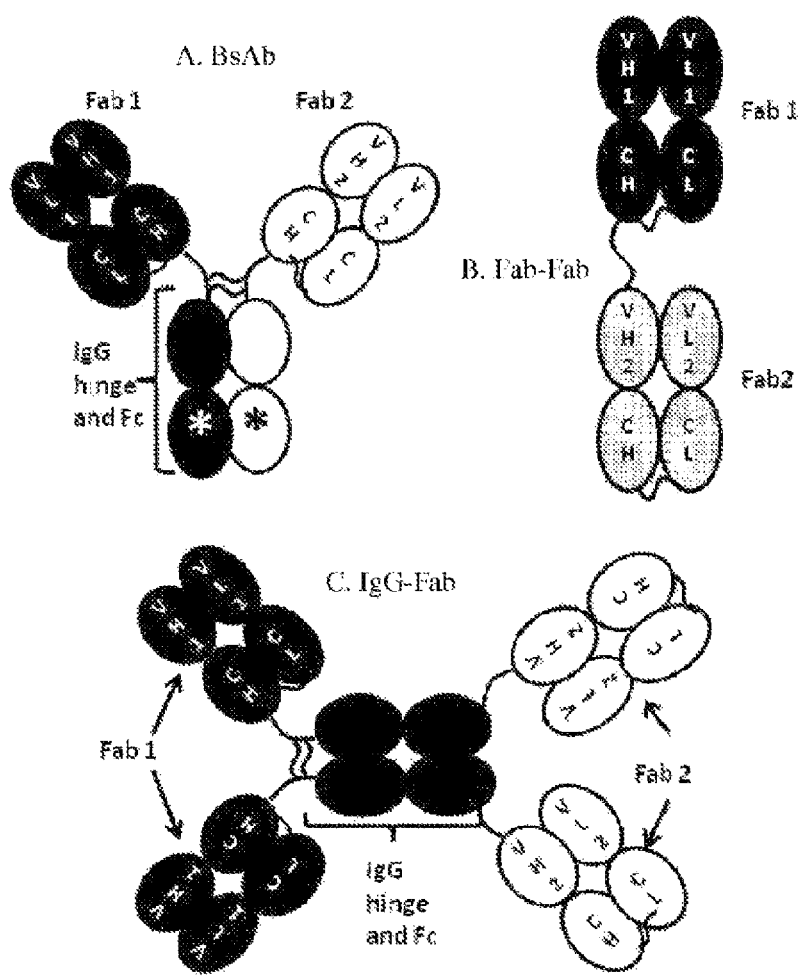
FIG. 1: Schematic diagrams of IgG (A), Fab-Fab (B) and IgG-Fab (C) design formats. The "*" in the IgG BsAb diagram indicates a heterodimerized antibody CH3 domain. The Fab-Fab format (B) could be prepared by expressing a polypeptide linker between the C-terminus of the HC of Fab 1 and the N-terminus of the HC or LC of Fab 2. Alternately, a polypeptide could connect the C-terminus of the LC of Fab 1 and the N-terminus of the LC or HC of Fab 2. Similarly, the additional Fab in the IgG-Fab (C) could be linked to the N-terminus of the HC or LC or the C-terminus of the LC.

The general structure of an "antibody" is very well-known. For a full length antibody of the IgG type, there are four amino acid chains (two "heavy" chains and two "light" chains) that are cross-linked via intra- and inter-chain disulfide bonds. When expressed in certain biological systems, e.g. mammalian cell lines, antibodies having unmodified human Fc sequences are glycosylated in the Fc region. Antibodies may be glycosylated at other positions as well. The subunit structures and three-dimensional configurations of antibodies are well known. Each heavy chain is comprised of an N-terminal heavy chain variable region ("$V_H$") and a heavy chain constant region ("$C_H$"). The heavy chain constant region is comprised of three domains ($C_H1$, $C_H2$, and $C_H3$) for IgG as well as a hinge region ("hinge") between the $C_{H1}$ and $C_{H2}$ domains. Each light chain is comprised of a light chain variable region ("$V_L$") and a light chain constant region ("$C_L$"). The $C_L$ and $V_L$ regions may be of the kappa ("κ") or lambda ("λ") isotypes. IgG antibodies can be further divided into subclasses, e.g., IgG1, IgG2, IgG3, IgG4, as appreciated by one of skill in the art.

The variable regions of each heavy chain-light chain pair associate to form binding sites. The heavy chain variable region ($V_H$) and the light chain variable region ($V_L$) can be subdivided into regions of hypervariability, termed complementarity determining regions ("CDRs"), interspersed with regions that are more conserved, termed framework regions ("FR"). Each $V_H$ and $V_L$ is composed of three CDRs and four FRs, arranged from amino-terminus to carboxy-terminus in the following order: FR1, CDR1, FR2, CDR2, FR3, CDR3, FR4. CDRs of the heavy chain may be referred to as "CDRH1, CDRH2, and CDRH3" and the 3 CDRs of the light chain may be referred to as "CDRL1, CDRL2 and CDRL3." The FRs of the heavy chain may be referred to as HFR1, HFR2, HFR3 and HFR4 whereas the FRs of the light chain may be referred to as LFR1, LFR2, LFR3 and LFR4. The CDRs contain most of the residues which form specific interactions with the antigen A wild type IgG antibody contains two identical fragments termed "fragment, antigen binding" (or Fab), each of which is composed of the $V_H$ and $C_H1$ domains of one heavy chain and the $V_L$ and $C_L$ domains of a light chain. Each Fab directs binding of the antibody to the same antigen. As used herein, the term "bi-specific antibody" or "IgG BsAb" refers to an IgG antibody comprising two distinct Fabs, each of which direct binding to a separate antigen, and composed of two distinct heavy chains and two distinct light chains. The $V_H$ and $C_H1$ domains of one heavy chain associate with the $V_L$ and $C_L$ domains of one light chain to form a "first" Fab, whereas the $V_H$ and $C_H1$ domains of the other heavy chain associate with the $V_L$ and $C_L$ domains of the other light chain to form a "second" Fab. More particularly, the term "bi-specific antibody", as used herein, refers to an IgG1, IgG2 or IgG4 class of bi-specific antibody. Even more particular, the term "bi-specific antibody" refers to an IgG1 or IgG4 class of bi-specific antibody, and most particularly an IgG1 class.

The methods exemplified herein can be used to co-express two distinct Fab moieties, for example Fabs with different Fv regions, with reduced mis-matching of respective HC/LC pairs. In addition to bi-specific antibodies and individual Fabs, the methods of the present invention can be employed in the preparation of other bi-specific antigen binding compounds. As used herein, the term "bi-specific antigen binding compound" refers to Fab-Fab and IgG-Fab molecules. FIG. 1, included herein, provides a schematic diagram of the structure of bi-specific, antibodies (IgG BsAb) as well as the Fab-Fab and IgG-Fab formats contemplated by the methods and compounds of the present invention.

The methods and compounds of the present invention comprise designed amino acid modifications at particular residues within the variable and constant domains of heavy chain and light chain polypeptides. As one of ordinary skill in the art will appreciate, various numbering conventions may be employed for designating particular amino acid residues within IgG variable region sequences. Commonly used numbering conventions include Kabat and EU index numbering (see, Kabat et al., *Sequences of Proteins of Immunological Interest*, 5th Ed, Public Health Service, National Institutes of Health, Bethesda, Md. (1991)). Other conventions that include corrections or alternate numbering systems for variable domains include Chothia (Chothia C, Lesk A M (1987), *J Mol Biol* 196: 901-917; Chothia, et al. (1989), *Nature* 342: 877-883), IMGT (Lefranc, et al. (2003), *Dev Comp Immunol* 27: 55-77), and AHo (Honegger A, Pluckthun A (2001) J Mol Biol 309: 657-670). These references provide amino acid sequence numbering schemes for immunoglobulin variable regions that define the location of variable region amino acid residues of antibody sequences. Unless otherwise expressly stated herein, all references to immunoglobulin heavy, chain variable region (i.e., $V_H$) amino acid residues (i.e. numbers) appearing in the Examples and Claims are based on the Kabat numbering system, as are all references to $V_L$ and $C_L$ residues. All references to immunoglobulin heavy chain constant region $C_H1$ and hinge appearing in the Examples and Claims are also based on the Kabat system, whereas all references to immunoglobulin heavy chain constant regions $C_H2$, and $C_H3$ are based on the EU Index numbering system. With knowledge of the residue number according to Kabat or EU Index numbering, one of ordinary skill can apply the teachings, of the art to identify amino acid sequence modifications within the present invention, according to any commonly used numbering convention. Note, while the Examples and Claims of the present invention employ Kabat or EU Index to identify particular amino acid residues, it is understood that the SEQ IDs appearing in the Sequence Listing accompanying the present application, as generated by Patent In Version 3.5, provide sequential numbering of amino acids within a given polypeptide and, thus, do not conform to the corresponding amino acid numbers as provided by Kabat or EU index.

However, as one of skill in the art will also appreciate, CDR sequence length may vary between individual IgG molecules and, further, the numbering of individual residues within a CDR may vary depending on the numbering convention applied. Thus, to reduce ambiguity in the designation of amino acid residues within CDRs, the disclosure of the present invention first employs Kabat to identify the N-terminal (first) amino acid of the HFR3. The amino acid residue to be modified is then designated as being four (4) amino acid residues upstream (i.e. in the N-terminal direction) from the first amino acid in the reference HFR3. For example, Design A of the present invention comprises the replacement of a WT amino acid in HCDR2 with a glutamic acid (E). This replacement is made at the residue located four amino acids upstream of the first amino acid of HFR3, according to Kabat. In the Kabat numbering system, amino acid residue X66 is the most N-terminal (first) amino acid residue of variable region heavy chain framework three (HFR3). One of ordinary skill can employ such a strategy to identify the first amino acid residue (most N-terminal) of heavy chain framework three (HFR3) from any human IgG1 or IgG4 variable region. Once this landmark is determined, one can then locate the amino acid four residues upstream (N-terminal) to this location and replace that amino acid residue (using standard insertion/deletion methods) with a glutamic acid (E) to achieve the "Design A" modification of the invention. Given any variable IgG1 or IgG4 immunoglobulin heavy chain amino acid query sequence of interest to use in the methods of the invention, one of ordinary skill in the art of antibody engineering would be able to locate the N-terminal HFR3 residue in said query sequence and then count four amino acid residues upstream therefrom to arrive at the location in HCDR2 that should be modified to glutamic acid (E).

As use herein, the phrase "a/an [amino acid name] substituted at residue . . . ", in reference to a heavy chain or light chain polypeptide, refers to substitution of the parental amino acid with the indicated amino acid. For example, a heavy chain comprising "a lysine substituted at residue 39" refers to a heavy chain wherein the parental amino acid sequence has been mutated to contain a lysine at residue number 39 in place of the parental amino acid. Such mutations may also be represented by denoting a particular amino acid residue number, preceded by the parental amino acid and followed by the replacement amino acid. For example, "Q39K" refers to a replacement of a glutamine at residue 39 with a lysine. Similarly, "39K" refers to replacement of a parental amino acid with a lysine.

An antibody, Fab or other antigen binding compound of the present invention may be derived from a single copy or clone (e.g. a monoclonal antibody (mAb)), including any eukaryotic, prokaryotic, or phage clone. Preferably, a compound of the present invention exists in a homogeneous or substantially homogeneous population. In an embodiment, the antibody, Fab or other antigen binding compound, or a nucleic acid encoding the same, is provided in "isolated" form. As used herein, the term "isolated" refers to a protein, peptide or nucleic acid which is free or substantially free from other macromolecular species found in a cellular environment.

A compound of the present invention can be produced using techniques well known in the art, e.g., recombinant technologies, phage display technologies, synthetic technologies or combinations of such technologies or other technologies readily known in the art. In particular, the methods and procedures of the Examples herein may be readily employed. An antibody, Fab or antigen binding compound of the present invention may be further engineered to comprise framework regions derived from fully human frameworks. A variety of different human framework sequences, may be used in carrying out embodiments of the present invention. Preferably, the framework regions of a compound of the present invention are of human origin or are substantially human (at least 95%, 97% or 99% of human origin.) The sequences of framework regions of human origin may be obtained from *The Immunnglobulin Factsbook*, by Marie-Paule Lefranc, Gerard Lefranc, Academic Press 2001, ISBN 012441351.

Expression vectors capable of directing expression of genes to which they are operably linked are well known in the art. Expression vectors can encode a signal peptide that facilitates secretion of the desired polypeptide product(s) from a host cell. The signal peptide can be an immunoglobulin signal peptide or a heterologous signal peptide. Desired polypeptides, for example the components of the bi-specific antibodies or Fabs prepared according to the methods of the present invention, may be expressed independently using different promoters to which they are operably linked in a single vector or, alternatively, the desired products may be expressed independently using different promoters to which they are operably linked in separate vectors. As used herein, a "host cell" refers to a cell that is stably or transiently transfected, transformed, transduced or infected with nucleotide sequences encoding a desired polypeptide product or products. Creation and isolation of host cell lines producing a bi-specific antibody, Fab or other antigen binding compound of the present invention can be accomplished using standard techniques known in the art.

Mammalian cells are preferred host cells for expression of the Fabs, bi-specific antibodies, or antigen binding compounds according to the present invention. Particular mammalian cells are HEK 293, NS0, DG-44, and CHO cells. Preferably, expressed polypeptides are secreted into the medium in which the host cells are cultured, from which the polypeptides can be recovered isolated. Medium, into which an expressed polypeptide has been secreted may be purified by conventional techniques. For example, the medium may be applied to and eluted from a Protein A or G column using conventional methods. Soluble aggregate and multimers may be effectively removed by common techniques, including size exclusion, hydrophobic interaction, ion exchange, or hydroxyapatite chromatography. Recovered products may be immediately frozen, for example at −70° C., or may be lyophilized.

The following Examples further illustrate the invention and provide typical procedures for carrying out various embodiments. However, it is understood that the Examples are set for the by way of illustration and not limitation, and that various modification may be made by one of ordinary skill in the art. In addition, Lewis et al., *Nature Biotech.*, 32(2); February 2014, provides additional illustration of embodiments of the present invention.

Example 1. Computational Design to Identify Modifications of $C_H1/C_L$ Interface Residues that Discriminate Between Designed and Native Immunoglobulin $C_H1/C_L$ Interfaces Residues for initial modification at the $C_H1/C_L$ interface are selected using a combination of computational and rational design strategies. Using a crystal structure of the IgG1/λ Fab (PDB ID 3TV3 (see, Lewis, S. M. and Kuhlman, B. A. (2011), *PLoS ONE* 6(6): e20872)), trimmed to heavy chain residues 112-228 and light chain residues 106A-211, the Rosetta software suite and related modeling applications are employed to evolve potential sequences for modification according to a desired fitness function (see, Kaufmann et al. (2010), *Biochemistry* 49; 2987-2998; Leaver-Fay et al. (2011), *Methods Enzymol.* 487; 545-574; Kuhlman et al. (2003), *Science* 302(5649); 1364-1368; and Leaver-Fay et al. (2011), *PLos ONE* 6(7): e20937). Briefly, Rosetta calculates a fitness score and binding energy based on a weighted sum of energy potentials treating phenomena such as van der Waals forces and hydrogen bonding forces. Overall, the summations of these different parameters are measured in units known as the Rosetta Energy Unit (REU). These values are interpreted as free energies, but are not directly translatable into typical units of energy.

Using a fitness function which favors the binding and stability of designed-$C_H1$/designed-$C_L$ complexes and disfavors binding affinity of undesired designed-$C_H1$/WT-$C_L$ and WT-$C_H1$/designed-$C_L$ complexes; initial sequence modifications resulting in binding orthogonality for designed $C_H1/C_L$ pairs are identified.

The identified mutations are subjected to computational re-docking of the $C_H1/C_L$ complex using RosettaDock via RosettaScripts (see, Chaudhury et al. (2011). *PLoS ONE* 6(8): e2247 and Fleishman et al. (2011), *PLoS ONE* 6(6): e20161). This allows determination of optimal binding positions for designed complexes and allows comparison with binding energies of the similarly docked WT complexes and the undesired designed-$C_H1$/WT-$C_L$ and WT-$C_H1$/designed-$C_L$ complexes. A deficit in the computational total score and binding energies for these undesired complexes predicts they will bind weakly to one another compared to the WT-$C_H1$/WT-$C_L$ and designed-$C_H1$/designed-$C_L$ complexes. Total energies are calculated using a Rosetta standard scorefunction, "Score12 prime." (see, Leaver-Fay et al. (2013), *Methods Enzymol.* 523; 109-143). Binding energies are calculated as the change in free energy (ΔG) separated score as reported by Rosetta's InterfaceAnalyzer tool (see, Lewis, S. M. and Kuhlman, B. A. (2011), *PLoS One* 6(6): e20872). Representative design constructs and their corresponding total score and binding energies are provided in Table 1.

TABLE 1

Rosetta multi-state computational design results.

| Construct ($C_H1/C_\lambda$) | Mutations[b] | HC mut/LC mut total score[a] | HC mut/LC mut binding energy | HC mut/LC wt total score | HC mut/LC wt binding energy | HC wt/LC mut total score | HC wt/LC mut binding energy |
|---|---|---|---|---|---|---|---|
| WT | None | −359 | −29 | — | — | — | — |
| 1.0 | H_F174T H_V190F L_L135F | −357 | −26 | −353 | −23 | −355 | −27 |
| 2.1 | H_F174G L_L135A L_S176W | −355 | −26 | −352 | −23 | −347 | −22 |
| 5.0 | H_D146K L_K129D | −359 | −29 | −355 | −28 | −359 | −29 |

TABLE 1-continued

Rosetta multi-state computational design results.

| Construct ($C_H1/C_\lambda$) | Mutations[b] | HC mut/LC mut total score[a] | HC mut/LC mut binding energy | HC mut/LC wt total score | HC mut/LC wt binding energy | HC wt/LC mut total score | HC wt/LC mut binding energy |
|---|---|---|---|---|---|---|---|
| 1.0 + 5.0 | H_D146K H_F174T H_V190F L_L135F L_K129D | −357 | −28 | −352 | −25 | −353 | −24 |

[a]Units for the fitness score are called Rosetta Energy Units (REUs).
[b]Mutations are designated by first identifying the heavy chain (H) or light chain (L), followed by the one letter abbreviation for the parental amino acid, the amino acid residue number and the one letter abbreviation for the replacement amino acid (For example, H_F174T indicates that residue 174 of the heavy chain is modified from a phenylalanine (F) to a threonine (T).

More than forty discrete initial designs, falling into about twenty different design paradigms (i.e., mutations with different amino acid substitution combinations and different residue positions), were identified after filtering of many more computationally-generated sequences. Select design paradigms were synthesized and further interrogated experimentally either in a full-length IgG1/λ construct or an IgG1/λ construct that lacks variable domains, each as described below (see Tables 2 and 3). Based on those experiments, three designs, Design 1.0, Design 2.1 and Design 5.0 and Design 1.0+5.0 demonstrated good biophysical properties and thermodynamic discrimination for designed-$C_H1$/designed-$C_L$ association over designed-$C_H1$/WT-$C_L$ or WT-$C_H1$/designed-$C_L$ association as demonstrated in thermal challenge assays (described below).

Synthesis of Test Articles.

To test the designs, a pertuzumab (see, Nahta et al. (2004), Cancer Res. 64; 2343-2346) human IgG1 with a human chimeric kappa $V_L$ and lambda $C_L$ ($C_\lambda$) is created. Briefly, the pertuzumab $V_H$ domain insert is generated using a PCR-based overlapping oligonucleotide synthesis procedure (Casimiro et al. (1997), Structure 5; 1407-1412) using the sequence from the published crystal structure (Franklin et al. (2004), Cancer Cell 5; 317-328). The insert contains appropriate AgeI and NheI restriction sites that enable it to be ligated directly into a linearized in-house pE vector (Lonza) containing an IgG1 constant domain sequence. The pertuzumab $V_L$ gene is also generated using overlapping oligonucleotide synthesis. A DNA sequence encoding the $V_L$ domain fused to $C_\lambda$ is constructed using PCR and an in-house plasmid template containing the $C_\lambda$ sequence. Both 5′ and 3′ flanking oligonucleotides and two internal primers are designed to anneal the C-terminus of the pertuzumab $V_L$ domain to the N-terminus of $C_\lambda$. The light chain insert is designed with HindIII and EcoRI restriction sites for direct ligation into a linearized in-house pE vector (Lonza) with a selectable GS marker system. Each pE mammalian expression vector is engineered to contain a common mouse antibody light chain signal sequence that is translated in-frame as part of the expressed protein and cleaved prior to secretion. All ligation constructs are transformed into E. coli strain TOP 10 competent cells (Life Technologies). Transformed bacterial colonies are picked, cultured, and the plasmids are prepped. Correct sequences are confirmed by DNA sequencing. The encoded sequences of the mature heavy chain and light chain proteins are given by SEQ ID NO:1 and SEQ ID NO:2, respectively.

To further interrogate the ability of $C_H1/C_L$ designs to provide a new and specific interface that discriminates from WT $C_H1/C_L$ interfaces, it is useful to remove the variable domains, which, if present, add complexity to the data interpretation. Therefore, human IgG1 and human, lambda constructs lacking variable genes ($V_H$ and $V_L$) are constructed. A recombinase-based subcloning strategy is used to remove the variable genes. Briefly, for the heavy chain plasmid, two double stranded oligonucleotides that encompass 15 base pairs 5′ of an XhoI site through the common mouse antibody light chain signal sequence followed immediately by a NheI site and 15 flanking base pairs (encoding the N-terminus of the IgG1 $C_H1$ domain for efficient recombination) are chemically synthesized. This double stranded oligonucleotide pair has the $V_H$ domain deleted. For the light chain plasmid, two double stranded oligonucleotides that encompass 15 base pairs 5′ of a BamHI site through the common mouse antibody light chain signal sequence followed immediately by an XmaI and 15 flanking base pairs (encoding the N-terminus of the lambda $C_L$ domain for efficient recombination) are chemically synthesized. This double stranded oligonucleotide pair has the $V_L$ domain deleted. The variable genes are digested out of the parental pertuzumab heavy chain and light chain plasmids using the XhoI/NheI and BamHI/XmaI enzymes, respectively. The corresponding oligonucleotide pairs are inserted into the linearized plasmids using the recombinase-based In-Fusion HD Cloning kit (Clontech) according to the manufacturer's protocol. The sequences of the heavy chain and light chain IgG1/λ constructs lacking variable domains are given by SEQ ID NO: 3 and SEQ ID NO: 4, respectively.

For generating small sets of mutations, the QuikChange II Site Directed Mutagenesis Kit (Agilent) may be used following the instructions provided by the manufacturer. For generating large sets of mutations (typically >3 mutations per chain), a gene synthesis strategy may be employed (G-blocks, IDT). The synthesized genes are designed to be compatible with the heavy chain and light chain construct lacking variable domains (described above). However, within the heavy chain construct, an Xho I site upstream of the common mouse light chain signal sequence is deleted using site directed mutagenesis and a new Xho I site is generated at the C-terminus (3′ end) of the coding region of the $C_H1$ domain. Synthesized genes are ligated to the heavy chain plasmid using the NheI and new XhoI restriction sites. Synthesized genes are added to the light chain plasmid using the BamHI and EcoRI restriction sites.

Protein Expression and Characterization.

Each plasmid is scaled-up by transformation into TOP10 E. coli, mixed with 100 mL luria broth in a 250 mL baffled flask, and shaken O/N at 220 rpm. Large scale plasmid purifications are performed using the BenchPro 2100 (Life Technologies) according to the manufacturer's instructions.

For protein production, plasmids harboring the heavy chain and light chain DNA sequences are transfected (1:2 plasmid ratio for the heavy chain and light chain plasmids, respectively) into ITEK293F cells using Freestyle transfection reagents and protocols provided by the manufacturer (Life Technologies). Transfected cells are grown at 37° C. in a 5% $CO_2$ incubator while shaking at 125 rpm for 5 days. Secreted protein is harvested by centrifugation at 10 K rpm for 5 min. Supernatants are passed through 2 μm filters (both large scale and small scale) for purification. Small scale (1 mL) purifications are performed by directly incubating 1 mL transfected supernatant with 100 μL resuspended, phosphate buffered saline (PBS) washed-Protein G magnetic beads (Millipore). Beads are washed 2-times with PBS and 1-time with 10-fold diluted PBS. Protein is eluted from the beads by adding 130 μL 0.01 M Acetate, pH 3.0. After harvesting, the eluants are immediately neutralized by adding 20 μL 0.1 M Tris, pH 9.0. The concentration of the purified proteins are determined by measuring the absorbance of the solutions at 280 nm using a NanoDrop UV-Vis spectrophotometer from ThermoScientific (Grimsley, G. R. and Pace, C. N. (2004), *Curr. Protoc. Protein Sci.*, Ch. 3 (3.1)).

Identities of representative transfected plasmids and the sequences they generate are provided in Table 2. Methods for characterization and the resulting data for each of these heavy chain/light chain designs are described below.

TABLE 2

Sequence composition of the $C_H1/C_L$ interface specificity designs based on Rosetta.

| Design | Mutations | Heavy Chain SEQ ID NO: | Light Chain SEQ ID NO: |
|---|---|---|---|
| WT pertuzumab IgG1/λ | None | 1 | 2 |
| WT IgG1/$C_λ$ lacking V-genes | None | 3 | 4 |
| Design 1.0[a] | HC_F174T, HC_V190F, LC_L135F | 5 | 6 |
| Design 2.1[b] | HC_F174G, LC_L135A, LC_S176W | 7 | 8 |
| Design 5.0[a] | HC_D146K, LC_K129D | 9 | 10 |
| Design 1.0 + 5.0[b] | HC_D146K, HC_F174T, HC_V190F, LC_K129D, LC_L135F | 11 | 12 |

[a] In the pertuzumab IgG1/λ format.
[b] In the IgG1/λ format lacking variable domains The proteins may be characterized using multiple methods, as described herein. For example, sodium dodecyl sulfate polyacrylamide gel electrophoresis (SDS-PAGE) analyses are used to evaluate expression and assembly of the HC and LC components. SDS-PAGE may be performed using NuPAGE® Novex 4-12% BisTris gels according to manufacturer protocols (Life Technologies). Approximately 15 μL of purified material from the magnetic bead purifications (see above) are loaded in each well. For reduced samples, 10% 0.5 M DTT in $H_2O$ is added. Protein bands on the gels are detected using a SimplyBlue™ Safe Stain (Life Technologies).

Enzyme-linked immunosorbent assays (ELISAs) for the detection of thermochallenged protein samples may also be performed to compare the stability of the designed samples against the wild-type control, proteins and the mis-matched designs. $T_{50}$ values, defined as the temperature at which 50% of ELISA signal that detects protein activity remains, after heating at elevated temperature for a specified period of time, can be determined for each sample to compare the stability of the designed HC/LC constructs relative to the stability of wild-type controls and mis-matched pairs. For the pertuzumab IgG1/λ proteins, 96-well U-bottom high protein binding 96-well plates (Greiner bio-one, cat #650061) are coated overnight at 4° C. with 100 μL/well of a polyclonal anti-human $C_λ$ antibody (Southern Biotech, cat #2070-01) at 2 μg/mL in a 0.05 M $NaHCO_3$ buffer, pH 8.3. The plates are then washed four times with PBS with 0.02% Tween80 (PBST) and blocked for 1 hr with casein (Thermo, cat #37528) at 37° C. The plates are washed again followed by the addition of isolated HEK293F culture supernatants containing the pertuzumab IgG1/λ protein designs (100 μL/well). Aliquots of each supernatant are pre-exposed to various temperatures for 1 hr using a PCR instrument with a 25° C. thermal gradient window. The thermal challenged pertuzumab IgG1/λ proteins (with or without mutations in the $C_H1/C_L$ domains) are incubated on the plate for 1 hr at 37° C. The plates are then washed and 200 ng/mL in-house biotinylated human HER-2-Fc (R&D systems, cat #1129-ER-020) is added at 100 μL/well (diluted in casein) for 1 hr at 37° C. The plates are washed again followed by the addition of streptavidin-HRP (Jackson Immunoresearch, cat #016-030-084) diluted 1:2000 in casein. The plates are then washed and SureBlue Reserve TMB 1-component substrate (KPL, cat #53-00-01) is added at 100 μL/well. The reaction is allowed to proceed for 5-15 minutes then quenched by the addition of 1% $H_3PO_4$. The absorbance at 450 nm is read using a SpectraMax 190 UV plate reader (Molecular Devices). A similar procedure is followed for the detection of thermochallenged IgG1/λ minus variable gene proteins using a polyclonal anti-human $C_H1$ antibody (2 μg/mL in casein; Meridian Life Sciences, cat #W90075C) to capture proteins from the supernatants and a HRP-labeled polyclonal anti-human $C_λ$ antibody (1:2000 dilution in casein; Southern Biotech, cat #2070-05) for detection (replacing the HER-2-Fc-biotin and streptavidin-HRP).

Characterization results for each of the designs depicted in Table 2 are provided in Table 3 below. Three designs, Design 2.1, Design 5.0, and Design 1.0+5.0 were found where the thermal stability of the designed HC/designed LC $C_H1/C_L$-containing IgG protein was superior both computationally and experimentally over at least one of the mismatched Designed HC/WT LC or WT HC/Designed LC pairs (Table 3). In some cases (including Designs 2.1 and 1.0+5.0), the designs were tested in the IgG1/$C_λ$ protein lacking variable domains. For both Design 1.0+5.0 and Design 2.1, a clear preference for the Designed HC/Designed LC pair could be seen by SDS-PAGE analysis as evident by a strong band at ~100 kDa resembling that of the wild-type HC/LC pairs. The Design 1.0+5.0 mismatched pairs (i.e., Designed HC/WT LC and WT HC/Designed LC) expressed too poorly to be seen on an SDS-PAGE gel. The Design 2.1 mismatched pairs demonstrated additional banding below the main band indicative of unassembled protein.

TABLE 3

Characterization of designed $C_H1/C_L$ antibody proteins.

| Construct | Mutation | Titer[a] (Construct vs. WT control) | Titer[a] ((HCmut/LCwt[b]) vs WT Control) | Titer[a] ((HCwt/LCmut[b]) vs WT Conrrol) | SDS-PAGE Assembly[c] | $T_5$ (° C.) | $T_{50}$ (° C.) HCmut/LCwt | $T_{50}$ (° C.) HCwt/LCmut |
|---|---|---|---|---|---|---|---|---|
| WT Pertuzumab IgG1/λ | None | 1.0 | n.d.[d] | n.d. | + | 66 | n.d. | n.d. |
| WT IgG1/C$_λ$ minus V-genes | None | 1.0 | n.d. | n.d. | + | 78 | n.d. | n.d. |
| Design 1.0[e] | HC_F174T HC_V190F LC_L135F | 1.0 | 3.1 | – | + | 67 | 67 | n.d. |
| Design 2.1[f] | HC_F174G LC_S176W LC_L135A | 1.1 | 0.2 | 0.5 | + | >75 | 69 | 74-75 |
| Design 5.0[e] | HC_D146K LC_K129D | 0.5 | 0.75 | 0.5 | + | 67 | 60 | 67 |
| Design 1.0 + 5.0[f] | HC_D146K HC_F174T HC_V190F LC_K129D LC_L135F | 0.6 | 0.0 | −0.02 | + | 73 | <45 | 53 |

[a]Titers are determined based on the protein G magnetic bead purified protein recoveries as described above. Titer values are given as a ratio of expression of the indicated designed contruct or mis-matched pair (i.e. HCmut/LCwt or HCwt/LCmut) relative to expression of the appropriate WT control.
[b]The mis-matched pairs were expressed separately by co-transfection of a designed HC or LC with a wild-type LC or HC, repectively.
[c]Assembly denoted by single band at 100 kDa by SDS-PAGE (+). Partial assembly denoted by multiple bands on SDS-PAGE including 100 kDa band (+/−). No band at 100 kDa on SDS-PAGE denoted by (−).
[d]n.d. = not determined.
[e]Determined in the pertuzumab IgG1 format.
[f]Determined in the IgG1/λ minus variable genes format.

The characterization results demonstrate that Design 1.0+5.0 maintains a high affinity and stable $C_H1/C_L$ interface with low capability for recognizing native immunoglobulin $C_H1/C_L$ domains. Additionally, Design 2.1 demonstrates high stability and specificity for itself while discriminating against binding to native (wt) immunoglobulin $C_H1/C_L$ domains.

Analytical size exclusion chromatography with in-line light static scattering (SEC/LS) is another characterization tool, used to confirm that the heterotetrameric HC/LC antibody complexes associate properly and continue to demonstrate monodisperse biophysical behavior. SEC/LS may be performed for each sample using 30-80 μL of purified eluant from the small scale-purification described above (concentrations ~0.1-0.4 mg/mL). For SEC/LS, the proteins are injected onto a Sepax Zenix SEC 200 analytical HPLC (7.8×300 mm) column equilibrated in 10 mM phosphate, 150 mM NaCl, 0.02% NaN$_3$; pH 6.8, using an Agilent 1100 HPLC system. Static light scattering data for material eluted from the SEC column are collected using a miniDAWN TREOS static light scattering detector coupled to an Optilab T-rEX in-line refractive index meter (Wyatt Technologies). UV data are analyzed using HPCHEM (Agilent). Protein molecular weights are determined by their static light scattering profiles using ASTRA V (Wyatt Technologies). SEC/LS analysis indicates that all of the proteins described in Table 3 were shown to be highly monodisperse with soluble aggregates <5% and indistinguishable from the wild-type IgG and IgG minus variable domain constructs.

Example 2. Optimization of Design 2.1

Design 2.1, as described in Example 1, is further optimized to improve specificity of assembly of the designed $C_H1/C_L$ interface versus a WT $C_H1/C_L$ interface. To aid in the design process, in-house crystal structures of Design 1.0+5.0 and Design 2.1 are first solved.

To generate protein for crystallography, isolated $C_H1/C_λ$ proteins (disulfide linked) are produced in E. Coli. The isolated $C_H1/C_λ$ proteins (no variable-genes or IgG-Fc) are subcloned into the pET-DUET plasmid from Novagen. The $C_H1$ insert (with a pelB signal sequence for secretion into the oxidative periplasmic environment) is synthesized (with a hexahistidine C-terminal tag) using overlapping PCR and subcloned into cassette 1 of the plasmid using the NheI and BamHI sites. The $C_λ$ insert is similarly synthesized and inserted between the NdeI and XhoI sites (no his tag). Designs 1.0+5.0 and Design 2.1 are generated from the WT plasmid using QuikChange II mutagenesis (Agilent). Each plasmid is transformed into CodonPlus BL21(DE3) chemically competent cells (Agilent) for expression. For each protein preparation, transformed and pre-cultured cells are used to inoculate 2×1.4 L luria broth supplemented with 100 μg/mL carbenicillin and 35 μg/mL chloramphenicol. The cultures are allowed to shake at 220 rpm at 37° C. until the OD$_{600}$ reached 1-1.5. At this stage, the culture temperature is reduced to 30° C. and 1 mM Isopropyl-1-thio-β-D-galactopyranoside is added. The cultures are allowed to grow for 3-4 hrs and harvested by centrifugation for 20 min at 4000 g. The proteins are resuspended in 50 mL of a periplasmic extraction buffer (500 mM sucrose, 100 mM Tris, pH 8, 1 mM EDTA, and 100 μg/mL hen-egg white lysozyme). The extracted proteins are diluted 10-fold into a 10 mM citrate, 10 mM NaCl buffer, pH 5.5 and passed over a 5 mL SP Sepharose FF HiTrap cation exchange column (GE Healthcare) at 5 mL/min using an AKTA Explorer (GE Healthecare). The proteins are eluted from the column using a gradient up to 0.7 M NaCl. The proteins are dialyzed into PBS and captured onto a Ni-Sepharose HiTRAP affinity column. The proteins are then eluted using a gradient up to 0.3 M imidazole. The proteins are then concentrated to ~3-10 mg/mL using VivaSpin6 centrifugal devices, dialyzed into 10 mM Tris, 100 mM NaCl, pH 8.0 and filtered.

For crystallography, the purified proteins are screened using the vapor diffusion crystallization method, whereby protein is first mixed with well solution and deposited in a small chamber with well solution, sealed and allowed to equilibrate with well solution, concentrating both protein and precipitating reagents in the protein drop. Such screens are conducted in a 96-well format (Intelli-plates, Art Robins Instrument) using the commercially available screens: PEGs, PEGs II, ComPAS, Classics, Classics II Suites (Qiagen). The initial setup utilizes a Phoenix robot (Art Robins Instrument), which deposits 0.3 μL of protein on 0.3 μL of well solution.

For the WT $C_H1/C_\lambda$ protein, initial screening is performed at 6 mg/ml protein. Protein crystals grew after 2 days in the following condition: 15% Ethanol/50% MPD/10 mM Sodium Acetate. These initial crystallization conditions are optimized in a set of vapor diffusion experiments where the concentration of the two components is varied, while the third is kept constant. The optimization experiments are conducted in 48-well format Intelli-plates (Art Robins Instrument). The optimization experiments result in thin needle-shaped crystals diffracting below 3 Å resolution.

Next, protein is re-screened at higher concentration of 9.2 mg/ml. Streak seeding using the needle-shaped crystals from the previous step is performed on, the following day. Streak seeding is a method promoting crystal nucleation by providing a ready-made nucleus (seed crystals) to assist nucleation and facilitate the growth of ordered crystals. This technique results in a new crystallization condition: 30% PEG4K. Optimizing of this condition is performed at 21° C. by varying the PEG4K concentration, the size of the drop containing the protein and reservoir solution mixture, and the ratio of the protein and reservoir content in the drop. Crystallization drops are seeded and crystals appeared on the next day, growing to the final size within 3 days. Crystals are transferred to a cryo-protection solution of the reservoir solution with PEG4K increased by 10% and supplemented by 20% PEG400 and flash frozen by immersion in liquid nitrogen before shipping to the Advanced Photon Source for data collection.

Design 1.0+5.0 is similarly screened and streak-seeded using the WT crystal seeds. Intergrown needle-shaped crystals appeared after 3 days at two conditions: 20% Isopropanol/20% PEG4K/100 mM tri-Sodium Citrate and 33% PEG6K/10 mM tri-Sodium Citrate. Both conditions are optimized, using the technique described above, resulting in single crystals for the optimization of the $2^{nd}$ condition. Final Design 1.0+5.0 single crystals are grown at 21° C. by mixing 1.2 μL of 3.9 mg/ml protein and 1.2 μL of reservoir solution, containing 40% PEG6K and 10 mM tri-Sodium Citrate dehydrate. Crystals are cryo-protected using reservoir solution increased by 10% PEG6K content and supplemented by 20% of Ethylene Glycol.

Design 2.1 crystallizes directly in conditions developed for Design 1.0+5.0. Single crystals are grown at 21° C. by mixing 1.5 μL of 5.1 mg/ml protein with 1.5 μL of reservoir, containing 39% PEG6K and 10 mM tri-Sodium Citrate. Crystals are cryoprotected using the same technique as for Design 1.0+5.0.

The conformations of the designed residues observed in the computational model structure and the experimental crystal structure of Design 1.0+5.0 were very similar (i.e., the designed residues adopted the same conformations in the model and the experimental in-house crystal of Design 1.0+5.0). However, the designed residues of Design 2.1 showed a substantially different orientation in the computational model than in an in-house crystal structure. Specifically, the light chain designed residue 176W and heavy chain native residue H172 of the in-house crystal structure did not adopt the conformations of the Rosetta computational model. The crystal also revealed a trans-cis isomerization between heavy chain residues G174 (mutated from F) and P175. This structural rearrangement was unanticipated by the model, but also not within the modeling degrees of freedom. Further modifications for Design 2.1 were generated following computational design methods essentially as described in Example 1, but using the in-house crystal structure of Design 2.1 as the starting point in place of the original 3TV3 crystal structure model.

Following molecular biology procedures essentially as described in Example 1, modifications to Design 2.1 are constructed in the IgG/Cλ construct lacking variable domains. Table 4 provides identities and corresponding mutations for representative further-optimized designs of Design 2.1.

TABLE 4

Optimization of Design 2.1.

| Design | $C_H1/C_L$ Mutations | HC SEQ ID NO: | LC SEQ ID NO: |
|---|---|---|---|
| Design 2.1.3.2 | HC_H172A, HC_F174G, LC_L135F, LC_S176W | 18 | 15 |
| Design 2.1.3.3 | HC_H172S, HC_F174G, LC_L135Y, LC_S176W | 19 | 20 |
| Design 2.1.3.3a | HC_H172A, HC_F174G, LC_L135Y, LC_S176W | 18 | 20 |

The optimized Design 2.1 proteins are expressed using the transient HEK293F system as described in Example 1. Each of the designs are tested for thermal stability by thermal challenge at temperatures ranging from 70-95° C. using the methodology as described in Example 1. The sustained presence of each design protein after heating is determined using the IgG1/λ minus variable gene ELISA also as described in Example 1. Results of the thermal challenge stability test for representative optimized designs of Design 2.1 as well as WT IgG1/$C_\lambda$ (no $V_H/V_L$) and Design 2.1 are provided below in Table 5.

TABLE 5

Optimization of Design 2.1

| Design | $C_H1/C_L$ Mutations | $T_{50}$ (° C.) |
|---|---|---|
| WT IgG1/$C_\lambda$ (no $V_H/V_L$) | None | 78.1 ± 0.5 |
| Design 2.1 | HC_F174G, LC_S176W, LC_L135A | >75 |
| Design 2.1.3.2 | HC_H172A, HC_F174G, LC_L135F, LC_S176W | 81.4 ± 0.5 |
| Design 2.1.3.3 | HC_H172S, HC_F174G, LC_L135Y, LC_S176W | 77.7 ± 0.5 |
| Design 2.1.3.3a | HC_H172A, HC_F174G, LC_L135Y, LC_S176W | 83 ± 2 |

The thermochallenge data in Table 5 indicates Design 2.1.3.2, Design 2.1.3.3 and Design 2.1.3.3a were the most stable constructs.

To further assess specificity of optimized designs of Design 2.1, a mass spectrometry (MS) method to directly measure the specificity versus the WT $C_H1/C_L$ domains is performed. Briefly, at the 2 mL transfection scale, a designed $C_L$ domain is co-transfected with a WT $C_L$ domain and either a designed heavy chain or a WT heavy chain. In this way the designed and WT $C_L$ proteins directly compete with one another during protein expression for binding to the heavy chain protein and secretion into the cell media. The assembled IgG/$C_L$ minus variable genes proteins are purified automatically using an Agilent 1100 series HPLC with autosampler and sample collector. The proteins are captured on a PG (protein G) HPLC column (Applied Biosystems, Cat #2-1002-00) at 2 mL/min, washed with phosphate buffered saline (PBS) and eluted with distilled deionized $H_2O$, 0.2% formic acid. The protein eluants are concentrated/dried on a Labconco CentriVap Speedvac for 3 hrs at 40° C. under vacuum. The proteins are resuspended in 100 μL distilled deionized water and neutralized with 20 mL 0.1 M Tris pH 8.0 (MediaTech, Inc., Cat #46-031-CM). The intermolecular disulfides (HC/LC and HC/HC) are reduced by the addition of 10 μL freshly solubilized 1 M dithiothreitol (DTT, Sigma, Cat #43815-1G). The samples are sequentially collected using an Agilent 1100 series HPLC with an autosampler and captured onto a reverse phase C4 analytical column for desalting using a water, 0.2% formic acid mobile phase. After separation of the protein from its buffer components, the proteins are bumped from the C4 column using a 10%/90% water/acetonitrile pulse (both with 0.2% formic acid) and injected into an Agilent 6210 time-of-flight liquid chromatography/masse spectrometry system molecular weight analyser. Theoretical mass-averaged molecular weights of the light chain and heavy chain components are determined using the GPMaw program (v. 8.20). The two separate light chains of the competition experiment can be easily discriminated from one another based on their different molecular weights. The relative counts of the ionized light chains hitting the detector are used to quantify the ratio of designed $C_L$ and WT $C_L$ protein that is bound to the heavy chain component and this data is shown in Table 6.

TABLE 6

Results of the competition LC specificity LC/MS assay.

| LC1 | LC2 | HC | % Assembly[a] (LC1/HC) | % Assembly[a] (LC2/HC) | Total Expression (μg/mL) |
|---|---|---|---|---|---|
| 2.1.3.2 Cλ | WT Cλ | WT HC | 11 | 89 | 73 |
| 2.1.3.2 Cλ | WT Cλ | 2.1.3.2 HC | 78 | 22 | 76 |
| 2.1.3.3a Cλ | WT Cλ | WT HC | 10 | 90 | 50 |
| 2.1.3.3a Cλ | WT Cλ | 2.1.3.3a HC | 99 | 1 | 80 |
| 2.1.3.3a Cλ | WT Cκ | WT HC | 8 ± 3 | 92 ± 3 | 63 ± 20 |
| 2.1.3.3a Cλ | WT Cκ | 2.1.3.3a HC | 100 ± 0.2 | 0.2 ± 0.2 | 75 ± 20 |

[a]"% Assembly" is calculated as described in the legend for Table 11, below

Results of the LC/MS competition experiments indicate significant specificity versus WT sequences is obtained using Designs 2.1.3.2 and 2.1.3.3a. Both Design 2.1.3.2$C_\lambda$ and Design 2.1.3.3a$C_\lambda$ proteins significantly out-competed WT $C_\lambda$ (and WT $C_\kappa$) for binding to their heavy chain protein counterpart containing the 2.1.3.2 or 2.1.3.3a heavy chain mutations. Conversely, Design 2.1.3.2 and Design 2.1.3.3a $C_\lambda$ proteins did not compete well with WT Cλ (and WT $C_\kappa$) for binding to the WT HC protein. Design 2.1.3.3a $C_\lambda$ provided slightly better specificity than Design 2.1.3.2$C_\lambda$ in the experiment.

Example 3. Designs to Generate Designed $V_H$ and $V_L$ Domains that Bind One Another Stronger than They Bind WT $V_L$ or $V_H$ Domains, Respectively To further optimize specific heavy chain-light chain assembly when co-expressing two Fabs, variable heavy chain/variable light chain ($V_H$/$V_L$) modifications are designed. $V_L$ position 1 and $V_H$ position 62 are first identified for modification. $V_L$ position 1 is modified to the positively charged residue arginine (R) and $V_H$ position 62 is modified to the negatively charged residue glutamic acid (E). This combination of charge modifications is denoted Design A. A second design modified $V_L$ position 38 and $V_H$ position 39 to generate a charge pair ($V_L$_Q38D and $V_H$_Q39K) at the site of the former hydrogen bonding interaction. This charge pair introduction is denoted Design B.

Design A, Design B, and a combination of Design A and B, denoted Design AB, are introduced into the plasmids for the pertuzumab light chain and heavy chain plasmids for mammalian expression. Plasmids containing Design 1.0+5.0 (with WT petuzumab $V_H$ and $V_L$) modifications are also constructed to generate heavy chains and light chains to potentially improve specificity of the variable domain designs over pairing with fully wild type heavy and light chains. The mutations are introduced using the using the QuikChange II mutagenesis kit (Agilent) according to the manufacturer's protocols constructs. The methods followed for plasmid production and purification are essentially as described in Example 1. The identities and corresponding sequences of Design A, Design B, and Design AB are provided in Table 7.

TABLE 7

SEQ ID NOs of Variable Domain and Constant Domain Designs in the pertuzumab HC and LC.

| Full-length HC/LC IgG Design | Mutations | HC SEQ ID NO: | LC SEQ ID NO: |
|---|---|---|---|
| Variable Domain Designs[a] | | | |
| Design A | HC_R62E, LC_D1R | 21 | 22 |
| Design B | HC_Q39K, LC_Q38D | 23 | 24 |
| Design AB | HC_R62E, HC_Q39K, LC_D1R, LC_Q38D | 25 | 26 |
| Constant Domain Designs[b] | | | |
| Design 1.0 + 5.0 | HC_D146K, HC_F174T, HC_V190F, LC_K129D, LC_L135F | 27 | 28 |

[a]The Variable Domain Designs contain the indicated mutations in the $V_H$ and $V_L$ domains and WT pertuzumab sequences in the $C_H$ and $C_L$ domains.
[b]The Constant Domain Designs contain the indicated mutations in the $C_H$ and $C_L$ domains and WT pertuzumab sequences in the $V_H$ and $V_L$ domains.

Each of the designed heavy chain and light chain plasmids are co-expressed transiently in HEK293F essentially as described in Example 1. To probe for specificity, the designed heavy chains and light chains are also expressed with a mismatched light chain or heavy chain as a control to probe for specificity. The mismatched heavy chain and light chain contain WT $V_H$ and $V_L$ domains and the Design 1.0+5.0 in the constant domains to add additional specificity (denoted in Table 8 below as HC(WT15) and LC(WT15), respectively). The expression supernatants are subjected to a thermal challenge by incubation for 1 hr at temperatures ranging from 45-75° C. and tested for binding hHER-2-Fc using an ELISA (methods described in Example 1). This ELISA format is sensitive to the stability of the variable domains. Additionally, all proteins are purified from their supernatants using the protein G magnetic bead protocol, essentially as described in Example 1, and formed fully assembled IgG molecules. In each of the cases (Design A and Design B), the apparent thermal stability of the matched heavy chain and light chain pairs is significantly higher than the mismatched pairs. The result indicate that the matched designed pairs are thermodynamically favored over the mismatched pairs and provides a thermodynamic basis for the specific, association of the Design A heavy chain and light chain for themselves and the Design B heavy chain and light chain for themselves over the association with the heavy chain and light chains containing WT variable domains. Combining the designs into a single construct, Design AB, further improved the thermodynamic specificity and resulted in reduced expression of the mismatched pairs. Results for the thermo-challenge testing are provided in Table 8.

TABLE 8

Summary of the thermochallenge data with Design A, Design B, and Design AB.

| Full Length HC/LC IgG Construct | HC/LC SEQ ID NO: | $T_{50}$ (° C.) |
|---|---|---|
| Matched pair Constructs | | |
| HC_Design A/LC_Design A | 21/22 | 63.6 ± 0.6 |
| HC_Design B/LC_Design B | 23/24 | 59.0 ± 1.0 |
| HC_Design AB/LC Design AB | 25/26 | 59.3 ± 0.5 |
| Mis-matched pair Constructs | | |
| HC (WT15)/LC Design A | 27/22 | 52.8 ± 0.6 |
| HC (WT15)/LC Design B | 27/24 | 46.7 ± 0.2 |
| HC (WT15)/LC Design AB | 27/26 | <45 |
| HC_Design A/LC (WT15) | 21/28 | 58.1 ± 0.2 |
| HC_Design B/LC (WT15) | 23/28 | 53.6 ± 0.4 |
| HC_Design AB/LC (WT15) | 25/28 | 57.9 ± 0.3 |

The results in Table 8 indicate that making any of the three compensatory charge pair modifications described above maintains the thermostability of heavy chain/light chain assembly within the design constructs while reducing the thermostability of the mis-matched designs. These variable domain designs can be added to the constant domain designs described in Examples 1 and 2 above to help improve specific heavy chain/light chain assembly.

Example 4. Multi-State Computational Designs to Create Additional $V_H/V_L$ Interface Modifications that Discriminate from the Native Immunoglobulin $V_H/V_L$ Interface Using PDB ID 3TCL (see, McLellan et al. (2011), *Nature* 480(7377); 336-343) and a multi-state design protocol essentially as described in Example 1, additional compensatory $V_H/V_L$ interface mutations that steer designed $V_H$ and $V_L$ domains from binding WT $V_H$ and $V_L$ domains are designed. Discrete designs are physically constructed within the pertuzumab IgG Fv region with different design paradigms (i.e., mutations with very different amino acid combinations and residue positions). The design constructs are mutated, expressed in HEK293F cells, and tested for expression level and thermal stability using similar protocols as described in Examples 1-3 above. Three discrete designs as depicted in Table 9 (denoted H.4, H.5, and H.6) are shown to express well and are about as stable as WT pertuzumab.

TABLE 9

Sequence ID numbers and thermal challenge data for Designs H.4, H.5, and H.6.

| Construct | Mutations | HC SEQ ID NO: | LC SEQ ID NO: | $T_{50}$ (° C.) |
|---|---|---|---|---|
| Pertuzumab | None | 1 | 2 | 61.8 ± 0.5 |
| H.4 | LC_Q38R, HC_Q39Y | 29 | 30 | 60.3 ± 0.5 |
| H.5 | LC_Q38R, HC_Q39F | 31 | 30 | 59.2 ± 0.5 |
| H.6 | LC_Q38R, HC_Q39W | 32 | 30 | 60.6 ± 0.5 |

Example 5. Combining the $C_H1/C_L$ and $V_H/V_L$ Interface Designs Results in Highly Specific HC/LC Pairing In this example, the variable domain Designs H.4, H.6 and AB are examined along with the constant domain Designs 2.1.3.2 and 2.1.3.3a. The specificity afforded by the $V_H/V_L$ and $C_H1/C_L$ designs in isolation and in combination with each other is measured using a similar LC/MS competition experiment as described in Example 3 (with the IgG/$C_L$ proteins lacking variable domains), but here full-length immunoglobulin heavy chains and light chains are used. In the experiment, two full-length light chains (with $V_L$ and $C_L$) are co-expressed and forced to compete for binding to a single heavy chain prior to secretion. Identities of the designs and the corresponding SEQ ID numbers for the constructs used in the specificity experiments are provided in Table 10. Again, the pertuzumab $V_H$ and $V_L$ sequences were used in every construct as a vector for the designs.

TABLE 10

Identity and Sequence identification for constructs used in Example 5.

| HC Name[a,b] | HC SEQ ID NO: | LC Name[a,b] | LC SEQ ID NO: |
|---|---|---|---|
| WT + WT HC | 1 | WT + WTλ LC | 2 |
| AB + WT HC | 25 | AB + WTλ LC | 26 |
| H.4 + WT HC | 29 | WT + WTκ LC | 33 |
| H.6 + WT HC | 32 | AB + WTκ LC | 34 |
| WT + 2133a HC | 35 | H.4 + WTλ LC | 30 |
| AB + 2133a HC | 37 | H.6 + WTλ LC | 30 |
| AB + 2132 HC | 37 | WT + 2133aλ LC | 36 |
| H.4 + 2133a HC | 39 | AB + 2133aλ LC | 38 |
| | | H.4 + 2133aλ LC | 40 |
| | | AB + 2132λ LC | 42 |
| | | H.4 + WTκ LC | 41 |

[a]Nomenclature is provided by having the first two characters of each protein specifying the variable domain design, while the subsequent numbering specifies the constant domain design (e.g., 'WT + WTκ LC' is a LC with WT pertuzumab $V_L$ and WT kappa $C_L$, while 'AB + 2133aλ LC' is a LC with Design AB in its $V_L$ and Design 2.1.3.3a in its lambda $C_L$. Similarly, 'AB + 2133a HC' is a HC with Design AB in its $V_H$ and Design 2.1.3.3a in its $C_{H1}$.)
[b]Some designs only have sequence differences in their HC or LC (e.g., AB + 2133a and AB + 2132 share identical HCs).
The LC/MS specificity data for the combinations tested is provided in Table 11.

TABLE 11

LC/MS analysis of the $V_H/V_L$ and $C_H1/C_L$ interface designs in isolation and in combination.

| LC1 | LC2 | HC | % Assembly[a] (LC1/HC) | % Assembly[a] (LC2/HC) | Expression (μg/mL) |
|---|---|---|---|---|---|
| WT + WTλ LC | WT + WTκ LC | WT + WT HC | 18 | 82 | 69 |
| AB + WTλ LC | WT + WTκ LC | WT + WT HC | 10 | 90 | 73 |
| AB + WTλ LC | WT + WTκ LC | AB + WT HC | 61 | 39 | 108 |
| AB + WTκ LC | WT + WTλ LC | WT + WT HC | 40 | 60 | 132 |
| AB + WTκ LC | WT + WTλ LC | AB + WT HC | 39 | 61 | 112 |
| H.4 + WTλ LC | WT + WTκ LC | WT + WT HC | 39 | 61 | 94 |
| H.4 + WTλ LC | WT + WTκ LC | H.4 + WT HC | 54 | 44 | 105 |
| H.6 + WTλ LC | WT + WTκ LC | WT + WT HC | 48 | 52 | 90 |
| H.6 + WTλ LC | WT + WTκ LC | H.6 + WT HC | 54 | 46 | 100 |
| H.4 + WTλ LC | AB + WTκ LC | AB + WT HC | 23 | 77 | 95 |
| H.4 + WTλ LC | AB + WTκ LC | H.4 + WT HC | 71 | 29 | 71 |
| H.6 + WTλ LC | AB + WTκ LC | AB + WT HC | 25 | 75 | 67 |
| H.6 + WTλ LC | AB + WTκ LC | H.6 + WT HC | 69 | 31 | 94 |
| WT + 2133aλ LC | WT + WTλ LC | WT + WT HC | 50 | 50 | 29 |
| WT + 2133aλ LC | WT + WTλ LC | WT + 2133a HC | 79 | 21 | 28 |
| WT + 2133aλ LC | WT + WTκ LC | WT + WT HC | 78 | 22 | 31 |
| WT + 2133aλ LC | WT + WTκ LC | WT + 2133a HC | 79 | 21 | 19 |
| AB + 2133aλ LC | WT + WTλ LC | WT + WT HC | 42 | 58 | 51 |
| AB + 2133aλ LC | WT + WTλ LC | AB + 2133a HC | 85 | 15 | 87 |
| H.4 + 2133aλ LC | WT + WTλ LC | WT + WT HC | 47 | 53 | 61 |
| H.4 + 2133aλ LC | WT + WTλ LC | H.4 + 2133a HC | 77 | 23 | 70 |
| AB + 2132λ LC | H.4 + WTκ LC | H.4 + WT HC | 11 | 89 | 66 |
| AB + 2132λ LC | H.4 + WTκ LC | AB + 2132 HC | 74 | 26 | 98 |
| AB + 2133aλ LC | H.4 + WTk LC | H.4 + WT HC | 15 | 85 | 74 |
| AB + 2133aλ LC | H.4 + WTk LC | AB + 2133a HC | 78 | 22 | 121 |
| AB + 2132λ LC | H.4 + WTλ LC | H.4 + WT HC | 9 | 91 | 94 |
| AB + 2132λ LC | H.4 + WTλ LC | AB + 2132 HC | 80 | 20 | 110 |
| AB + 2133aλ LC | H.4 + WTλ LC | H.4 + WT HC | 9 ± 1 | 91 ± 1 | 76 ± 3 |
| AB + 2133aλ LC | H.4 + WTλ LC | AB + 2133a HC | 87 ± 2 | 13 ± 3 | 70 ± 5 |

[a]The percent assembly is calculated based on the relative area under the deconvoluted mass spectrometry peaks (i.e., proportional to the number of counts hitting the detector) of each of the LCs co-purified bound to the HC prior to mass spectrometry analysis. Purified samples are reduced with DTT prior to analysis-as described in Example 2.

The data in Table 11 indicates that generating specificity at the $V_H/V_L$ interface by combining Design AB in one Fab and Design H.4 in the other Fab resulted in significant specificity (~70-80% specificity) without any constant domain designs. Pairing the most selectively specific $V_H/V_L$ domain designs (AB in one Fab and H.4 in the other) with the most selective constant domain designs (2.1.3.2 or 2.1.3.3a) resulted in improved specificity overall, indicating that while the variable domains may dominate, the constant domains contribute to specificity (Table 11). The best combination used a combination of Design AB (in $V_H/V_L$) and 2.1.3.3a (in $C_H1/C_L$) in Fab #1 and Design H.4 (in $V_H/V_L$) with a WT $C_H1/C_L$ in Fab #2. This combination repeatedly generated a highly specific set of HC/LC interactions with roughly 90% specificity in both directions (Table 11).

Example 6. Achieving Improved Specific HC/LC Fab Assembly within IgG Bispecific Antibodies (BsAbs)

Two sets of IgG bispecific antibodies (BsAbs) are constructed to test how combining the designs AB2133a and H.4WT may enable specific heavy chain/light chain assembly of specific Fabs. All subcloning and mutagenesis protocols followed are essentially as described in previous Examples. The first BsAb consists of a combination of pertuzumab (anti-HER-2) and matuzumab (anti-EGFR) (see, Bier et al. (1998), *Cancer Immunol. Immunother.* 46; 167-173) and the second consists of a combination of MetMAb (anti-cMET) (see, Jin et al. (2008), *Cancer Res.* 68; 4360-4368) and an anti-Axl antibody YW327.6S2 (see, WO2011/014457 and Ye et al. (2010), *Oncogene* 29; 5254-5264). All sequences for the native antibodies are publicly available. To simplify our ability to observe specific assembly using LC/MS, all HCs are deglycosylated by mutating asparagine 297 (the site of N-linked glycosylation in the antibody $C_H2$ domain) to glutamine. To promote heterodimerization in the IgG-Fc, aspartic acid 399 and glutamic acid 356 are both mutated to lysine in one of the heavy chains of the anti-HER-2/anti-EGFR pair and one of the heavy chains of the anti-MET/anti-Axl pair. The remaining heavy chain in each pair had lysine 409 and lysine 392 mutated to aspartic acid (see, Gunasekaran et al. (2010), *JBC* 285; 19637-19646). It should be noted that other designs to promote heavy chain heterodimerization may be substituted to achieve the same overall affect. Sequence ID numbers of the immunoglobulin chains used to generate the IgG BsAbs are provided in Table 12.

TABLE 12

Sequence ID numbers of the HCs and LCs constructed to demonstrate the specific assembly of IgG BsAbs using the design Fab $V_H/V_L$ and $C_H1/C_L$ interfaces.

| HC Name | SEQ ID NO: | LC Name | SEQ ID NO: |
|---|---|---|---|
| WT antibody sequences | | | |
| pG1 (pertuzumab) | 1 | pλ (pertuzumab $V_L$ and $C_λ$) | 2 |
| | | pκ (pertuzumab $V_L$ and $C_κ$) | 33 |
| mG1 (matuzumab) | 43 | mλ (matuzumab $V_L$ and $C_λ$) | 44 |
| | | mκ (matuzumab $V_L$ and $C_κ$) | 45 |
| METG1 (METMAb) | 46 | METλ (METMAb $V_L$ and $C_λ$) | 47 |
| | | METκ (METMAb $V_L$ and $C_κ$) | 48 |
| AxlG1 (anti-Axl) | 49 | Axlλ (anti-Axl $V_L$ and $C_λ$) | 50 |
| | | Axlκ (anti-Axl $V_L$ and $C_κ$) | 51 |
| Control IgG HCs and LCs with WT (native) $V_H/V_L$ and $C_H1/C_L$ interfaces[a] | | | |
| (−)pG1 | 52 | pλ (pertuzumab $V_L$ and $C_λ$) | 2 |
| (+)mG1 | 53 | mλ (matuzumab $V_L$ and $C_λ$) | 44 |
| (−)METG1 | 54 | mκ (matuzumab $V_L$ and $C_κ$) | 45 |
| (+)AxlG1 | 55 | METλ (METMAb $V_L$ and $C_λ$) | 47 |
| | | Axlλ (anti-Axl $V_L$ and $C_λ$) | 50 |
| | | Axlκ (anti-Axl $V_L$ and $C_κ$) | 51 |

TABLE 12-continued

Sequence ID numbers of the HCs and LCs constructed to demonstrate the specific assembly of IgG BsAbs using the design Fab $V_H/V_L$ and $C_H1/C_L$ interfaces.

| HC Name | SEQ ID NO: | LC Name | SEQ ID NO: |
|---|---|---|---|
| IgG HCs and LCs with design $V_H/V_L$ and $C_H1/C_L$ interfaces[a,b] | | | |
| AB + 2133a(−)[pG1] | 13 | AB + 2133a[pλ] | 38 |
| H.4 + WT(+)[mG1] | 57 | AB + 2133a[pκ] | 56 |
| AB + 2133a(−)[METG1] | 60 | H.4 + WT[mλ] | 58 |
| H.4 + WT(+)[AxlG1] | 17 | H.4 + WT[mκ] | 59 |
| | | AB + 2133a[METλ] | 61 |
| | | AB + 2133a[METκ] | 62 |
| | | H.4 + WT[Axlλ] | 16 |
| | | H.4 + WT[Axlk] | 14 |

[a]The HC designs with (−) contained the K409D and K392D mutations while the HC designs with the (+) contained the D399K and E356K mutations. Both the (+) and (−) - containing HCs also have the N297Q mutation to eliminate N-linked glycosylation.
[b]Nomenclature is essentially as described in Table 10 above. The first two characters of each protein specify the variable domain design, while the subsequent numbering specifies the constant domain design (e.g., a LC designated 'AB + 2133a[pλ]' contains Design AB in its $V_L$ and Design 2.1.3.3a in its lambda $C_L$. Similarly, an HC designated 'AB + 2133a(−)[pG1]' contains Design AB in its $V_H$ and Design 2.1.3.3a in its $C_{H1}$, and the K409D and K392D substitutions in the CH3 domain.) The notation appearing within the brackets refers to the variable and constant domain of the particular parental antibody HC or LC containing the indicated design (e.g., "[pG1]" refers to a heavy chain containing a pertuzumab variable domain and IgG1 constant domain, whereas "[mG1]" refers to a heavy chain with a matuzumab variable domain and IgG1 constant domain; similarly, "[pλ]" refers to a light chain with pertuzumab variable domain and λ constant domain, whereas "[METλ]" refers to a light chain with METMAb variable domain and λ constant domain)

To determine if the designed $V_H/V_L$ (AB and H.4) and $C_H1/C_L$ (2.1.3.3a and WT lamda or kappa) interfaces would enable specific IgG BsAb assembly over what occurs naturally with no FAb interface designs in place, transient transfections of particular designed Fab constructs followed by LC/MS analyses are performed. For each IgG BsAb, two heavy chains and two light chains are simultaneously transfected using separate plasmids into mammalian HEK293F cells using transfection protocols essentially as described in the previous Examples. The designed IgG BsAbs include the deglycosylation mutation and Fc heterodimerization mutations as described above. Further, a control set of IgG BsAbs with the deglycosylation and Fc heterodimerization mutations and light chains with both $C_κ$ or $C_λ$ domains, but without the designed $V_H/V_L$ and $C_H1/C_L$ modifications, are also created by transfection of appropriate heavy chains and light chains. In each Designed IgG BsAb pair, one heavy chain and light chain (shown viable in both the $C_λ$ and $C_κ$ isotype) contained Design H.4, while the other heavy chain and light chain (shown viable in both the $C_λ$ and $C_κ$ isotype) contained Design AB and Design 2.1.3.3a. The exact heavy chain and light chain composition of each IgG BsAb synthesized is provided in Table 13.

TABLE 13

The HC and LC elements of each IgG BsAb and the resulting percentage of correct and incorrect IgG BsAb assembly based on the LC/MS intensities of the fully heterotetrameric species.

Anti-HER-2/Anit-EGFR IgG BsAbs

| IgG BsAb[b] | HC1[c] | LC1[c] | HC2[c] | LC2[c] | % LC1LC2[a] (correct) | % LC1$_2$ (incorr.) | % LC2$_2$ (incorr.) |
|---|---|---|---|---|---|---|---|
| HEControl λλ[c] | (−)pG1 | pλ | (+)mG1 | mλ | 65 | 23 | 12 |
| HEControl λκ | (−)pG1 | pλ | (+)mG1 | mκ | 75 | 0 | 15 |
| HEDesign λλ | AB + 2133a (−)[pG1] | AB + 2133a [pλ] | H.4 + WT (+)[mG1] | H.4 + WT [mλ] | 90 | 8 | 2 |
| HEDesign λκ | AB + 2133a (−)[pG1] | AB + 2133a [pλ] | H.4 + WT (+)[mG1] | H.4 + WT [mκ] | 90 | 7 | 3 |
| HEDesign κλ | AB + 2133a (−)[pG1] | AB + 2133a [pκ] | H.4 + WT (+)[mG1] | H.4 + WT [mλ] | 82 | 18 | 0 |
| HEDesign κκ | AB + 2133a (−)[pG1] | AB + 2133a [pκ] | H.4 + WT (+)[mG1] | H.4 + WT [mλ] | 87 | 10 | 3 |

Anti-cMET/Anti-Axl IgG BsAbs

| IgG BsAb | HC1[c] | LC1[c] | HC2[c] | LC2[c] | % LC1LC[a] (correct) | % LC1$_2$[a] (incorr) | % LC2$_2$[a] (incorr) |
|---|---|---|---|---|---|---|---|
| MAControl λλ | (−)METG1 | METλ | (+)AxlG1 | Axlλ | 70 | 27 | 3 |
| MAControl λκ | (−)METG1 | METλ | (+)AxlG1 | Axlκ | 61 | 38 | 1 |
| MADesign λλ | AB + 2133a (−)[METG1] | AB + 2133a [METλ] | H.4 + WT (+)[AxlG1] | H.4 + WT [Axlλ] | 95 | 5 | 0 |
| MADesign λκ | AB + 2133a (−)[METG1] | AB + 2133a [METλ] | H.4 + WT (+)[AxlG1] | H.4 + WT [Axlκ] | 100 | 0 | 0 |
| MADesign κλ | AB + 2133a (−)[METG1] | AB + 2133a [METκ] | H.4 + WT (+)[AxlG1] | H.4 + WT [Axlλ] | 97 | 2 | 1 |

TABLE 13-continued

The HC and LC elements of each IgG BsAb and the resulting
percentage of correct and incorrect IgG BsAb assembly based
on the LC/MS intensities of the fully heterotetrameric species.

| MADesign κκ | AB + 2133a (−)[METG1] | AB + 2133a [METκ] | H.4 + WT (+)[AxlG1] | H.4 + WT [Axlλ] | 90 | 7 | 3 |

<sup>a</sup>The LC/MS method is sensitive for heterotetrameric IgGs containing mismatched HC pairs (HC1HC1 or HC2HC2), but none were detected. The percent values represent the relative counts detected for covalently linked (non-reduced) heterotetramers HC1HC2LC1LC2 (correctly formed) compared to incorrect HC1HC2LC1LC1 (incorr.) and incorrect HC1HC2LC2LC2 (incorr.).
<sup>b</sup>Each BsAb is designated λλ, λκ, κλ, or κκ based on the $C_L$ compositions (lambda or kappa) of its LCs.
<sup>c</sup>Nomenclature for each heavy chain or light chain construct is essentially as described above in Tables 10 and 12

The data in Table 13 demonstrates that incorporating the $V_H/V_L$ and $C_H1/C_L$ designs into the IgG BsAbs significantly improved the correct assembly of the desired heterotetrameric species (i.e., HC1/LC1+HC2/LC2). Without the Fab designs, the average correct assembly was about 70% and 65% for the anti-HER-2/anti-EGFR and anti-cMET/anti-Axl IgG BsAbs, respectively. With the Fab designs incorporated, the average correct assembly was about 87% and 96% for the anti-HER-2/anti-EGFR and anti-cMET/anti-Axl IgG BsAbs, respectively.

Next, the IgG BsAbs may be tested for their oligomeric nature using analytical size exclusion chromatography (SEC). First, the IgG BsAbs are purified at the 1 mL scale from HEK293F supernatants using the protein G magnetic bead procedure, essentially as described in Example 1. For SEC analysis, between 10-50 μg of each protein was applied to a Yarra G3000 (7.8×300 mm) analytical SEC column (Phenomenex) with all other assay parameters similar to the protocol as described in Example 1. SEC of the pertuzumab (anti-HER-2) and matuzumab (anti-EGFR) control IgGs demonstrated slightly different SEC retention times for the two proteins due to differences in their variable domains. Further, the anti-HER-2/anti-EGFR IgG BsAbs tested demonstrate primarily monomeric behavior with SEC retention times between what was observed for non-bispecific pertuzumab and matuzumab controls, which might be expected if the proteins contain one pertuzumab Fab and one matuzumab Fab. Similar to pertuzumab and matuzumab, the METMAb and anti-Axl control IgGs demonstrate slightly different retention times by SEC. The anti-cMet/anti-Axl IgG BsAbs also demonstrate primarily monomeric behavior with retention times approximating the average of the control antibodies, non-bispecific antibodies. In addition, the two control IgG anti-cMet/anti-Axl BsAbs that did not have the Fab specificity designs incorporated, and which demonstrated significant populations of mismatched light chain pairings, also showed multiple monomeric species by SEC. The four anti-cMet/anti-Axl BsAbs containing the Fab specificity designs did not demonstrate this behavior.

Example 7 Functional Activity of Designed IgG BSAbs

The dual-binding behavior of the synthesized BsAbs may be assessed using both sandwich ELISA and surface plasmon resonance assays as follows.

Two sandwich ELISAs are developed, one for detecting anti-HER-2/anti-EGFR BsAb activity and one for detecting anti-cMET/anti-Axl BsAb activity. For both ELISAs, clear 96-well round bottom high binding Immulon microtiter plates (Greiner bio-one; cat #650061) are coated overnight at 2-8° C. with 50 μL/well 1 μg/mL hHER-2-Fc or 1 μg/mL hHGFR(cMet)-Fc (both from R&D systems) in a 50 mM $Na_2CO_3$ pH 8 buffer. The plates are washed 4 times with PBST and blocked with 100 μL/well casein buffer (Pierce) for 1 hr at 37° C. The plates are then washed 4 times with PBST and the parental IgG controls or BsAb IgG test articles are added at 50 μL/well and 5 μg/mL and serially diluted 1:3 down the plate. The test articles are incubated on the plate for 1 hr at 37° C. The plates are then washed 4 times with PBST and 50 μL/well 0.2 μg/mL hEGFR-Fc-biotin or hAxl-Fc-biotin (both from R&D systems) is added for 1 hr at 37° C. The plates are then washed 4 times with PBST followed by the addition of a 50 μL/well streptavidin-HRP (Jackson Labs) diluted 1:2000 in PBST. The streptavidin-HRP is incubated in each well for 1 hr at 37° C. The plates are then washed 4 times with PBST and 100 μL/well 1-component TMB substrate is added (KPL laboratories). After approximately 10 minutes, 100 mL/well 1% $H_3PO_4$ (in $H_2O$) is added to each plate to quench the reaction. Absorbance (450 nm) of every well in the plates is read using a SpectraMax UV plate reader (Molecular Devices). Biotin-labeling of the hEGFR-Fc and hAxl-Fc proteins is performed using EZ-Link Sulfo-NHS-LC-Biotin (Thermo Scientific) according to the manufacturer's protocol.

Both sandwich ELISAs were capable of demonstrating the dual-binding behavior of the BsAbs. For both the anti-HER-2/anti-EGFR and the anti-cMet/anti-Axl IgG BsAbs, the monoclonal IgG controls (pG1, mG1, METG1, or AxlG1) demonstrated no ability to generate signal in the sandwich ELISAs. The control IgG BsAbs with no Fab redesigns (HEControlλλ, HEControlλκ, MAControlλλ, MAControlλκ) generated sigmoidal binding curves in the assay. All the IgG BsAbs with the Fab redesigns also demonstrated sigmoidal binding curves. Average $EC_{50}$ values for the control and designed IgG BsAbs were as follows: HEControl $EC_{50}$=470±90 ng,/mL; HEDesign $EC_{50}$=280±20 ng/mL; MAControl $EC_{50}$=260±80; and MADesign $EC_{50}$=220±20.

Surface plasmon resonance experiments may also be performed to evaluate the dual-binding behavior of the BsAbs using, for example, on a Biacore3000 using HBS-EP as the running buffer (GE Healthcare). Briefly, hHER-2-Fc-biotin and hAxl-Fc-biotin (both at 20 μg/mL) are immobilized onto SA sensorchip surfaces by injection of 20 over 2 minutes at 10 μL/min. Next, 20 μL of each control IgG, control IgG BsAb, or designed IgG BsAb, diluted to 30 nM in HBS-EP buffer, is injected over these sensorchip surfaces at 5 μL/min followed by a secondary 20 μL injection of 20 nM hEGFR-Fc or hHGFR(cMet)-Fc. The hHER-2-Fc and hAxl-Fc sensorchip surfaces are regenerated by raising the flow rate to 50 μL/min and injecting two 5 μL injections of a 0.1 M glycine solution at pH 2.5 and pH 2.0, respectively.

Figure 2:
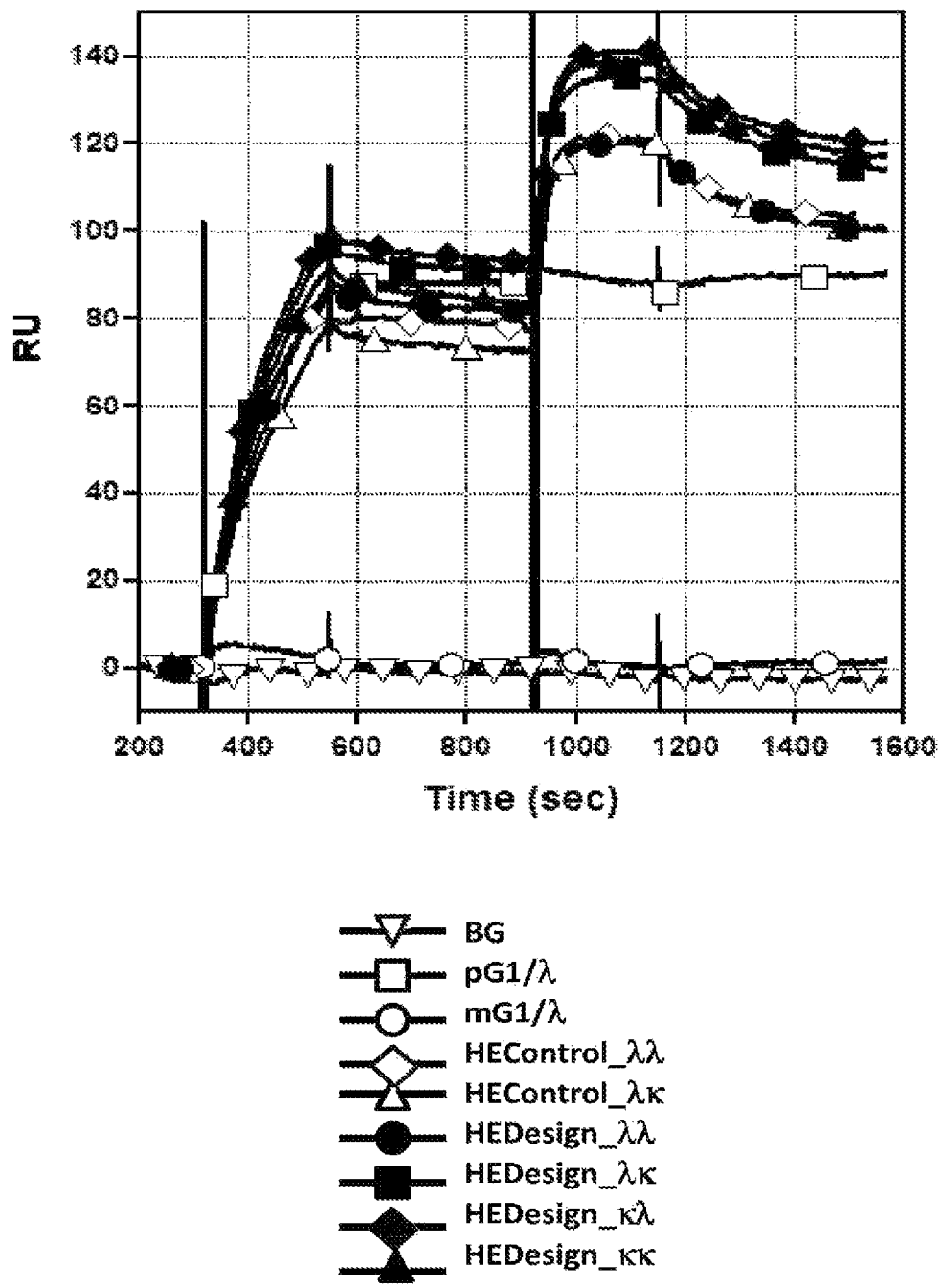
FIGS. 2 and 3: Surface Plasmon resonance (Biacore) traces demonstrating the dual-binding behavior of the anti-HER-2/anti-EGFR (FIG. 2) and anti-cMET/anti-Axl (FIG. 3) IgG BsAbs: Bispecific binding of the Fab Redesigned BsAbs (HE Designs (FIG. 2) and MA Designs (FIG. 3)) is evident by increases in signal during both injection cycles (300-540 sec and 940-1180 sec). The monospecific MAbs pertuzumab IgG1 (pG1) and matuzumab IgG1 (mG1) (FIG. 2) and METMAb IgG1 (METG1) and Anti-Axl IgG1 (AxlG1) (FIG. 3) do not demonstrate this activity. The control molecules without Fab redesigns (i.e., HE Control and MA Control), but harboring $C_H3$ heterodimerization mutations also demonstrate bispecific binding activity.
Figure 3:
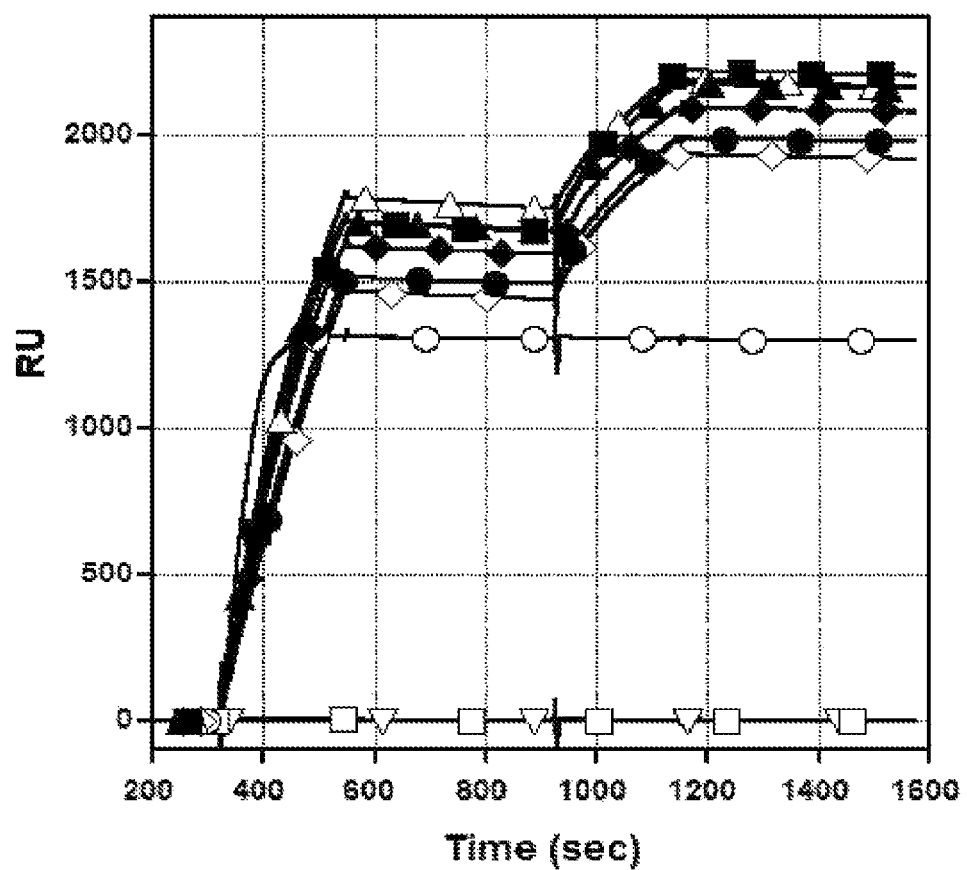
Figure 3:
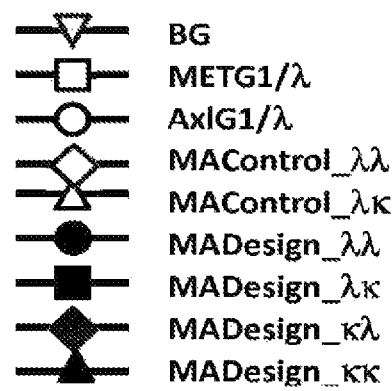

None of the monoclonal IgGs (pG1, mG1, METG1, or AxlG1) demonstrated dual binding activity in the assay (FIGS. 2 and 3). Both the control IgG BsAbs and the BsAbs containing Fab designs demonstrated strong dual-binding activity in the assay.

Example 8—Optimization of Constant Domain Design 2133a Using CH1/Ckappa

In certain contexts, constant domain ($C_H/C_L$) design denoted 2133a was determined to provide less correct HC/LC pairing specificity when used in $C_H1/C_\kappa$ compared to its use in $C_H1/C_\lambda$ (See, for example the EGFR×HER2 bispecific antibody assembly in Table 13). It was also found that the 2133a constant domain design destabilized when used in $C_H1/C_\kappa$ compared to WT $C_H1/C_\kappa$ (see Table 15, below).

To assess stability of the 2133a design IgG1/$C_\kappa$ proteins lacking variable domains [WT=SEQ ID NO: 3 (HC) and 63 (LC); Design 2133a=SEQ ID NO: 18 (HC) and 64 (LC)] are generated using molecular biology, expression, and purification methods as generally described in previous examples. The stability of the two purified proteins (WT and 2133a IgGs lacking variable domains or Fvs) are characterized using differential scanning calorimetry (DSC) as follows. The midpoints of the thermal unfolding transitions (denoted '$T_m$') of the $C_H1/C_\kappa$ domains provide a measure of their relative stability. The $T_m$ of the 2133a-containing $C_H1/C_\kappa$ domain was 67.7° C. while that of WT $C_H1/C_\kappa$ was 70.8° C. DSC is performed using an automated capillary DSC (capDSC, GE Healthcare). Protein solutions and reference (buffer) solutions are sampled automatically from a 96-well plate using, the robotic attachment. Before each protein scan, at least one buffer/buffer scan is performed, to define the baseline for subtraction. All 96-well plates containing protein are stored within the instrument at 6° C. Samples are run at 1.0 mg/ml protein concentration in PBS. Scans are performed from 10 to 95° C. at 90° C./hr using the low feedback mode. Scans are analyzed using the origin software supplied by the manufacturer. Subsequent to the subtraction of reference baseline scans; nonzero protein scan baselines are corrected using a third-order polynomial. Based on the analyses, the IgG1/$C_\kappa$ protein harboring the 2133a design was less stable than the WT protein (see Table 15, below).

Utilizing an in-house crystal structure of $C_H1/C_\lambda$ with the 2133a design, we identified $C_H1\_A172$ (design 2133a already contains an H172A substitution) and $C_H1\_V190$ as residue positions to randomize. The 2133a IgG1/$C_\kappa$ constructs lacking variable domains (SEQ ID NO: 18 and 64) are used to create the libraries for screening and analysis. The libraries are generated using the QuikChange II Site-Directed Mutagenesis Kit (Agilent) using protocols provided by the manufacturer. The constructs are expressed via transient transfection in HEK293F cells as generally described in Example 1. Titers of the proteins are assessed using the HPLC Protein G quantitation and collection method as generally described in Example 2. The proteins are assessed for their stability properties using a thermal challenge assay similar to that described in Example 1. Unique to this assay, the plates are coated with a sheep anti-human Fd (CH1) polyclonal antibody (Meridian Life Sciences, cat #W90075C) at 1 µg/ml, and 100 µL/well in a 0.05 M NaHCO₃ buffer, pH 8.3 for 1 hr at 37° C. or overnight at 4° C. Thermally resistant IgG1/$C_\kappa$ protein is detected by adding a detection antibody (HRP-labeled goat anti-human kappa, Southern Biotechnology, cat #2060-5) at a 1:10,000 dilution in PBS-T into every well at 100 µL/well and incubating for 1 hr at 37° C. Other assay parameters are generally as described previously.

From the library, three HC mutants, A172R, V190M, and V190I, are identified that stabilized the 2133a-containing $C_H1/C_\kappa$ domains in the thermal challenge assay. Combinations comprising $C_H1\_A172R\_V190M$ or $C_H1\_A172R\_V190I$ were also generated. Table 14 provides a listing of Sequence ID numbers for these 2133a $C_H1$ mutant proteins.

Larger scale (≥100 mL) transfections of the single and double mutant modifications of design 2133a $C_H1/C_\kappa$ constructs are generated in HEK293F cells. The transfected cells are cultured as generally described in Example 1 for small scale cultures. Supernatants with protein are clarified using 0.2 µm filters. The $C_H1/C_\kappa$ (−Fv) proteins are purified using standard protein A affinity chromatography methods. The proteins are buffer exchanged into PBS and analyzed by DSC as described above for the WT and 2133a $C_H1/C_\kappa$ (−Fv) proteins. The results of the DSC analyses showed that the single and double mutant combinations were stabilizing to the 2133a $C_H1/C_\kappa$ domains (Table 15).

TABLE 14

Sequence ID numbers of the HC and LC designs improving the stability or specificity of the 2133a design in CH1/Cκ.

| Modified 2133a HC for Improved Stability | Sequence ID number |
|---|---|
| HC (−$V_H$) 2133a_A172R | SEQ ID 65 |
| HC (−$V_H$) 2133a_V190M | SEQ ID 66 |
| HC (−$V_H$) 2133a_V190I | SEQ ID 67 |
| HC (−$V_H$) 2133a_A172R_V190M | SEQ ID 68 |
| HC (−$V_H$) 2133a_A172R_V190I | SEQ ID 69 |
| Cκ_2133a_V133L | SEQ ID 70 |
| Cκ_2133a_S174Q | SEQ ID 71 |
| Cκ_2133a_S174D | SEQ ID 72 |
| Cκ_2133a_V133L_S174Q | SEQ ID 73 |
| Cκ_2133a_V133L_S174D | SEQ ID 74 |
| (−)PG1_AB2133a[a] | SEQ ID 13 |
| (−)PG1_AB2133a_MR[b] | SEQ ID 75 |
| (−)PG1_AB2133a_IR[b] | SEQ ID 76 |
| (−)MetG1_AB2133a | SEQ ID 60 |
| (−)MetG1_AB2133a_MR[b] | SEQ ID 77 |
| (−)MetG1_AB2133a_IR[b] | SEQ ID 78 |
| Pκ_AB2133a | SEQ ID 56 |
| Pκ_AB2133a_LD[b] | SEQ ID 79 |
| Pκ_AB2133a_LQ[b] | SEQ ID 80 |
| Metκ_AB2133a | SEQ ID 62 |
| Metκ_AB2133a_LD[b] | SEQ ID 81 |
| Metκ_AB2133a LQ[b] | SEQ ID 82 |
| (+)MG1_H4[a] | SEQ ID 57 |
| (+)TG1_H4[a] | SEQ ID 83 |
| Mκ_H4 | SEQ ID 59 |
| Tκ_H4 | SEQ ID 87 |

[a]The HC designs with (−) contained the K409D and K392D mutations while the HC designs with the (+) contained the D399K and E356K mutations. Both the (+) and (−) − containing HCs also have the N297Q mutation to eliminate N-linked glycosylation.
[b]'MR' refers to $C_H1$ mutations A172R and V190M. 'IR' refers to $C_H1$ mutations A172R and V190I. 'LD' refers to Cκ mutations V133L and S174D. 'LQ' refers to Cκ mutations V133L and S174Q.

TABLE 15

Expression and differential scanning calorimetry (DSC) results for mutants of the 2133a-containing IgG1/Cκ protein lacking variable domains.

| Protein | Expression Level (µg/mL) | DSC $T_m$ (° C.)[a] |
|---|---|---|
| HC (−$V_H$) WT/Cκ_WT | 15 | 70.8 ± 0.1 |
| HC (−$V_H$) 2133a/Cκ_2133a | 19 | 67.7 ± 0.2 |
| HC (−$V_H$) 2133a_A172R/Cκ_2133a | 16 | 70.0 |
| HC (−$V_H$) 2133a_V190M/Cκ_2133a | 21 | 69.1 |
| HC (−$V_H$) 2133a_V190I/Cκ_2133a | 14 | 68.6 |
| HC (−$V_H$) 2133a_A172R_V190M/Cκ_2133a | 43 | 70.1 |
| HC (−$V_H$) 2133a_A172R_V190I/Cκ_2133a | 43 | 69.2 |

[a]The DSC Tm refers to the midpoint of the cooperative unfolding transition of the $C_H1$/Cκ heterodimer in each of these constructs.

Using the LC competition assay as generally described in Example 2, the specificity afforded by the 2133a design mutations in $C_H1/C_\kappa$ instead of $C_H1/C_\lambda$ is assessed. As shown in Table 16 below, the WT $C_\kappa$ protein (SEQ ID 63) shows little tendency to associate with the 2133a HC (SEQ ID 18) protein with or without the stabilizing mutations depicted in Table 15. However, it was observed that the 2133a-containing $C_\kappa$ domain (SEQ ID 64) could associate with a WT HC (SEQ ID 3) more strongly than a WT $C_\kappa$ domain (SEQ ID 63, see Table 16, below).

Using in-house 2133a/2133a and WT/WT $C_H1/C_\lambda$ crystal structures, 2133a $C_\kappa$ residue positions V133 and S174 were identified as positions where potential new interactions with 2133a-containing $C_H1$ domains could be generated, that might be incompatible with WT $C_H1$. Screening for 2133a $C_\kappa$ mutations that maintained binding to the 2133a design HC, while decreasing binding with WT HC, three mutations ($C_\kappa$_V133L, $C_\kappa$_S174Q, and $C_\kappa$_S174D) were found to provide beneficial specificity in the LC $C_\kappa$ competition assay (Table 16) (Sequence ID numbers of these constructs are provided in Table 14, above). Each of these mutations maintained the dominance of design 2133a $C_\kappa$ binding to 2133a $C_H1$ over WT $C_\kappa$, while decreasing the proportion of design 2133a $C_\kappa$ binding to WT $C_H1$ compared to WT $C_\kappa$. Further, the V133L mutation could be combined with either S174Q or S174D to provide further improvements in specificity (Table 16).

2133a Cκ mutants V133L and S174D (denoted 'LD') and V133L and S174Q (denoted 'LQ'). The mutants were added to both a Pertuzumab (anti-HER2) and MetMAb (anti-cMet) IgG1/kappa HC/LC pair containing the 2133a designs. To promote heavy chain heterodimerization, the Pertuzumab and MetMAb HCs contained the K409D and K392D mutations, denoted '(−)', while the complementary Matuzumab and Trastuzumab HCs contained the D399K and E356K mutations, denoted '(+)' (see, Gunasckaran et al., (2010), *JBC* 285; 19637-19646). Both the (+) and (−)-containing HCs also have the N297Q mutation to eliminate N-linked glycosylation. The Pertuzumab HC/LC pairs were co-expressed with an H4WT-containing Matuzumab IgG1/kappa HC/LC pair to form a HER2×EGFR IgG bispecific antibody. The MetMAb HC/LC pairs were co-expressed with an H4WT-containing Trastuzumab IgG1/kappa HC/LC pair to form a cMet×HER2 IgG bispecific antibody. The Sequence ID numbers for all sequences used in the study are provided in Table 14, above. All LCs in this study were fully kappa (i.e., VκCκ).

The ability to co-express each of the antibody pairs consisting of 2 HCs and 2 LCs (four chains total) and have them assemble into correctly formed IgG BsAbs was determined by MS as generally described in Example 6, above. Results of the co-expression studies are provided in Table

TABLE 16

Competition of Ckappa proteins binding to a single IgG1 HC (no variable domains) with variants of the 2.1.3.3a design

| LC1 | LC2 | HC | % Assembly[a] (LC1/HC) | % Assembly[a] (LC2/HC) |
|---|---|---|---|---|
| Cκ_2133a | Cκ_WT | HC (−$V_H$) WT | 86.6 ± 9.9 | 13.4 ± 9.9 |
| Cκ_2133a | Cκ_WT | HC (−$V_H$) 2133a | 98.8 ± 1.2 | 1.2 ± 1.2 |
| Cκ_2133a_V133L | Cκ_WT | HC (−$V_H$) WT | 70 | 30 |
| Cκ_2133a_S174Q | Cκ_WT | HC (−$V_H$) WT | 59 | 41 |
| Cκ_2133a_S174D | Cκ_WT | HC (−$V_H$) WT | 62 | 38 |
| Cκ_2133a_V133L_S174Q | Cκ_WT | HC (−$V_H$) WT | 0 | 100 |
| Cκ_2133a_V133L_S174Q | Cκ_WT | HC (−$V_H$) 2133a | 100 | 0 |
| Cκ_2133a_V133L_S174Q | Cκ_WT | HC (−$V_H$) 2133a A172R_V190M | 100 | 0 |
| Cκ_2133a_V133L_S174Q | Cκ_WT | HC (−$V_H$) 2133a A172R_V190I | 97.8 | 2.2 |
| Cκ_2133a_V133L_S174D | Cκ_WT | HC (−$V_H$) WT | 28.5 | 71.5 |
| Cκ_2133a_V133L_S174D | Cκ_WT | HC (−$V_H$) 2133a | 100 | 0 |
| Cκ_2133a_V133L_S174D | Cκ_WT | HC (−$V_H$) 2133a_A172R_V190M | 100 | 0 |
| Cκ_2133a_V133L_S174D | Cκ_WT | HC (−$V_H$) 2133a_A172R_V190I | 100 | 0 |

[a]As described in previous examples, the % assembly was derived using the ratio of counts for each LC detected by the mass spectrometer after purifying the expressed IgG(−Fv) proteins using the anti-Fc, releasing the Cκ domains using DTT.

The 2133a $C_H1$ and Cκ mutants were then added to two separate full-length HCs and LCs (including variable domains) to assess their ability to impact specific bispecific antibody assembly. The 2133a mutants A172R and V190M (denoted 'MR') and A172R and V190I (denoted 'IR') were each combined for the testing as were the compatible design 17, below. All data points are the average of between 3 and 9 individual measurements and the error represents the standard deviation. Differences between the correct assembly in the absence and presence of the 'MR', 'IR', 'LD', and/or 'LQ' designs were tested for their significance using a standard or paired t-test.

TABLE 17

Specific Assembly of IgG BsAbs Using 2133a Variant CH1/Ckappa Designs.

| HC1[a,b] | LC1[a] | HC2[a,b] | LC2[a] | % Correct IgG BsAb w/Std.Dev. | P-value (One-tailed t-test) |
|---|---|---|---|---|---|
| (−)PG1_AB2133a | Pκ_AB2133a | (+)MG1_H4 | Mκ_H4 | 71.8 ± 4.5 (n = 9) | |

TABLE 17-continued

Specific Assembly of IgG BsAbs Using 2133a Variant CH1/Ckappa Designs.

| | | | | | |
|---|---|---|---|---|---|
| (−)PG1_AB2133a_MR | Pκ_AB2133a | (+)MG1_H4 | Mκ_H4 | 62.2 ± 3.3 (n = 5) | N/A |
| (−)PG1_AB2133a_IR | Pκ_AB2133a | (+)MG1_H4 | Mκ_H4 | 56.6 ± 2.4 (n = 5) | N/A |
| (−)PG1_AB2133a | Pκ_AB2133a_LD | (+)MG1_H4 | Mκ_H4 | 76.3 ± 7.1 (n = 9) | P = 0.063 |
| (−)PG1_AB2133a | Pκ_AB2133a_LQ | (+)MG1_H4 | Mκ_H4 | 82.9 ± 13.1 (n = 8) | P = 0.015 |
| (−)PG1_AB2133a_MR | Pκ_AB2133a_LD | (+)MG1_H4 | Mκ_H4 | 94.9 ± 1.7 (n = 5) | P < 0.001 |
| (−)PG1_AB2133a_MR | Pκ_AB2133a_LQ | (+)MG1_H4 | Mκ_H4 | 77.3 ± 1.7 (n = 5) | P = 0.01 |
| (−)PG1_AB2133a_IR | Pκ_AB2133a_LD | (+)MG1_H4 | Mκ_H4 | 76.2 ± 9.6 (n = 4) | P = 0.14 |
| (−)PG1_AB2133a_IR | Pκ_AB2133a_LQ | (+)MG1_H4 | Mκ_H4 | 91.2 ± 3.05 (n = 3) | P < 0.001 |

| HC1[a,b] | LC1[a] | HC2[a,b] | LC2[a] | % Correct IgG BsAb w/Std.Dev. | P-value (One-tailed paired t-test) |
|---|---|---|---|---|---|
| (−)MetG1_AB2133a | Metκ_AB2133a | (+)TG1_H4 | Tκ_H4 | 51.8 ± 2.8 (n = 3) | |
| (−)MetG1_AB2133a_MR | Metκ_AB2133a | (+)TG1_H4 | Tκ_H4 | 44.9 ± 11.6 (n = 3) | N/A |
| (−)MetG1_AB2133a_IR | Metκ_AB2133a | (+)TG1_H4 | Tκ_H4 | 34.8 ± 8.4 (n = 3) | N/A |
| (−)MetG1_AB2133a | Metκ_AB2133a_LD | (+)TG1_H4 | Tκ_H4 | 73.7 ± 1.6 (n = 3) | P = 0.006 |
| (−)MetG1_AB2133a | Metκ_AB2133a_LQ | (+)TG1_H4 | Tκ_H4 | 65.5 ± 2.1 (n = 3) | P < 0.001 |
| (−)MetG1_AB2133a_MR | Metκ_AB2133a_LD | (+)TG1_H4 | Tκ_H4 | 61.0 ± 3.1 (n = 3) | P = 0.015 |
| (−)MetG1_AB2133a_MR | Metκ_AB2133a_LQ | (+)TG1_H4 | Tκ_H4 | 50.1 ± 1. (n = 3) | Not significant |
| (−)MetG1_AB2133a_IR | Metκ_AB2133a LD | (+)TG1_H4 | Tκ_H4 | 56.2 ± 1.6 (n = 3) | P = 0.035 |
| (−)MetG1_AB2133a_IR | Metκ_AB2133a LQ | (+)TG1_H4 | Tκ_H4 | 50.7 ± 2.0 (n = 3) | Not significant |

[a]All Pertuzumab and MetMAb molecules have the AB2133a HC/LC design with or without the further HC or LC mutations. All Matuzumab and Trastuzumab molecules have the H4 design mutations in their variable domains. All LCs are fully Kappa (i.e., VκCκ).
[b]The HC designs with (−) contained the K409D and K392D mutations while the HC designs with the (+) contained the D399K and E356K mutations. Both the (+) and (−) - containing HCs also have the N297Q mutation to eliminate N-linked glycosylation.

Both the 'LD' and 'LQ' paired mutations provided significant improvements in correct LC pairing within the IgG bispecific antibodies over utilization of unmodified AB2133a kappa LCs. Adding 'LD' and 'LQ' mutant combinations to the AB2133a $C_κ$ provided an average 13% and 12%, respectively, benefit in correct LC assembly over what was obtained in their absence. While the HC 'MR' and 'IR' mutations are stabilizing to the 2133a $C_H1/C_κ$ (interaction, their impact on specificity was less clear. Adding the HC 'MR' and 'IR' mutations in isolation decreased the correct IgG bispecific antibody assembly in all cases. In most cases, adding the HC 'MR' or 'IR' mutants to either LC 'LQ' or 'LD' mutations led to either no increase or a decrease in correct assembly; however, the addition of 'IR' to 'LQ' within the Anti-HER2×Anti-EGFR IgG bispecific antibody led to an approximate 10% increase in correct assembly over what was observed with 'LQ' alone. Thus, while the 'MR' and 'IR' mutations improve the stability of design 2133a $C_H1/C_κ$-containing bispecific antibodies, it appears to be case specific whether the 'MR' and 'IR' mutations improve specificity.

Example 9—Additional Specificity Designs to Improve LC Specificity when Expressing IgG Bispecific Antibodies To further improve the specificity of IgG bispecific antibody assembly, additional designs within the variable domains that drive improved HC/LC pairing specificity were pursued. A charge/polar pair of amino acids at HC_Q105/LC_K42 was identified for manipulation. LC_K42 was mutated to D and HC_Q105 was mutated to R within the pertuzumab IgG1/kappa H4WT design. After analyzing expression and LC competition data (as general described in previous Examples), LC_K42D and HC_Q105R, when added to H4 variable domain designs, provided slight improvement in H4(+K42D) pertuzumab LC pairing with its cognate HC H4(+Q105R) design when co-expressed with an AB2133a pertuzumab LC (~20% improvement). Co-expressing the H4(+K42D) pertuzumab LC with the design AB2133a pertuzumab LC and HC also did not markedly decrease the observed assembly level of the design AB2133a pertuzumab HC and LC pair. This additional design mutation (HC_Q105R/LC_K42D) is denoted as 'DR' in the Tables 18 and 19 below.

Inspection of a Fab crystal structure (pdb id: 3HC4) reveals a lysine at HC residue 228 and an aspartic acid at LC residue 122 near the distal end of the antibody Fab located near to the HC/LC disulfide bond. To provide charge-based steering that may favor proper HC/LC pairing, these charged residues were modified (HC_K228D/LC_D122K) in Pertuzumab H4WT IgG1/kappa. (To ensure the HC/LC disulfide bond was not disrupted by the charge swap, the HC residue 230 was mutated to glycine and HC residue 127 was mutated to cysteine.) This charge swap and cysteine modification is denoted 'CS'.

To determine whether the 'CS' and 'DR' designs might improve correct HC/LC assembly when expressing IgG bispecific antibodies, these designs were tested in isolation and in combination in antibodies containing the H4WT IgG1/kappa design. The Pertuzumab IgG1/kappa molecules containing AB2133a designs were paired with other IgG1/kappa antibodies containing the H4WT designs (with and without the 'DR' and/or 'CS' mutations) including BHA10 (Jordan, J L, et al. (2009) *Proteins* 77:832-41), Matuzumab, and Trastuzumab (i.e., Herceptin). Additionally, Pertuzumab with H4WT IgG1/kappa (with and without the 'DR' and/or 'CS' mutations) was tested for bispecific IgG assembly with Trastuzumab-containing the AB2133a designs in IgG1/kappa. The Pertuzumab and Trastuzumab HCs containing the AB2133a Fab designs contained the K409D and K392D mutations, denoted '(−)', while the complementary H4WT designs (with and without the 'DR' and/or 'CS' mutations) contained the D399K and E356K mutations, denoted '(+)' (see, Gunasekaran et al, (2010), *JBC* 285; 19637-19646). Both the (+) and (−)-containing HCs also had the N297Q mutation to eliminate N-linked glycosylation. To generate IgG bispecific antibodies, the HC and LC from Pertuzumab are co-transfected with the HC and LC of a second antibody in 2 mL HEK293F cells. The resulting material is secreted from the cells, purified as described in Example 2 and characterized by MS. The Sequence ID numbers of all the HCs and LCs used in the experiment are provided in Table 18.

TABLE 18

Sequence ID numbers of the HC and LC designs improving the specificity of HC/LC assembly.

| Sequence names for constructs used to demonstrate additional improvements in the specificity of Fab Designs | SEQ ID NO: |
|---|---|
| (−)PG1 AB2133a | SEQ ID 13 |
| (+)PG1 H4WT | SEQ ID 91 |
| (+)PG1 H4WT + CS | SEQ ID 92 |
| (+)PG1 H4WT + DR | SEQ ID 93 |
| (+)PG1 H4WT + CS + DR | SEQ ID 94 |
| Pκ AB2133a | SEQ ID 56 |
| Pκ H4WT | SEQ ID 41 |
| Pκ H4WT + CS | SEQ ID 95 |
| Pκ H4WT + DR | SEQ ID 96 |
| Pκ H4WT + CS + DR | SEQ ID 97 |
| (+)BHA10G1 H4WT | SEQ ID 104 |
| (+)BHA10G1 H4WT + CS | SEQ ID 105 |
| (+)BHA10G1 H4WT + DR | SEQ ID 106 |
| (+)BHA10G1 H4WT + CS + DR | SEQ ID 107 |
| (+)MG1 H4WT | SEQ ID 57 |
| (+)MG1 H4WT + CS | SEQ ID 98 |
| (+)MG1 H4WT + DR | SEQ ID 99 |
| (+)MG1 H4WT + CS + DR | SEQ ID 100 |
| (+)TG1 H4WT | SEQ ID 83 |
| (+)TG1 H4WT + CS | SEQ ID 84 |
| (+)TG1 H4WT + DR | SEQ ID 85 |
| (+)TG1 H4WT + CS + DR | SEQ ID 86 |
| (−)TG1 AB2133a | SEQ ID 108 |
| BHA10κ H4WT | SEQ ID 109 |
| BHA10κ H4WT + CS | SEQ ID 110 |
| BHA10κ H4WT + DR | SEQ ID 111 |
| BHA10κ H4WT + CS + DR | SEQ ID 112 |
| Mκ H4WT | SEQ ID 59 |
| Mκ H4WT + CS | SEQ ID 101 |
| Mκ H4WT + DR | SEQ ID 102 |
| Mκ H4WT + CS + DR | SEQ ID 103 |
| Tκ H4WT | SEQ ID 87 |
| Tκ H4WT + CS | SEQ ID 88 |
| Tκ H4WT + DR | SEQ ID 89 |
| Tκ H4WT + CS + DR | SEQ ID 90 |
| Tκ AB2133a | SEQ ID 113 |

The results of the MS measurements of percentage of correctly formed HC/LC pairs are provided in Table 19. All data points are the average of between 3-5 individual measurements and the error represents the standard deviation. Differences between the correct assembly in the absence and presence of the 'DR', 'CS', or 'CS+DR' designs were tested for their significance using a paired t-test.

TABLE 19

Specific assembly of IgG bispecific antibodies utilizing fully kappa LCs (i.e., VκCκ) with and without (i) VH_Q105R/VL_K42D (DR), (ii) CH1_S127C_K228D_C230G/CL_D122K (CS), or the combination of (i) and (ii).

| HC1[a] | LC1[b] | HC2[a] | LC2[b] | % Correct IgG BsAb w/Std.Dev. | P-value (One-tailed paired t-test) |
|---|---|---|---|---|---|
| Anti-HER2(pertuzumab)XAnti-LTbR(BHA10) IgG Coexpression ||||||
| (−)PG1 AB2133a | Pκ AB2133a | (+)BHA10G1 H4WT | BHA10κ H4WT | 78.8 ± 6.6 (n = 3) | |
| (−)PG1 AB2133a | Pκ AB2133a | (+)BHA10G1 H4WT + CS | BHA10κ H4WT + CS | 87.2 ± 3.0 (n = 3) | P = 0.03 |
| (−)PG1 AB2133a | Pκ AB2133a | (+)BHA10G1 H4WT + DR | BHA10κ H4WT + DR | 84.7 ± 3.6 (n = 3) | P = 0.07 |
| (−)PG1 AB2133a | Pκ AB2133a | (+)BHA10G1 H4WT + CS + DR | BHA10κ H4WT + CS + DR | 87.4 ± 4.2 (n = 3) | P = 0.03 |

TABLE 19-continued

Specific assembly of IgG bispecific antibodies utilizing fully kappa LCs (i.e., VκCκ) with and without (i) VH_Q105R/VL_K42D (DR), (ii) CH1_S127C_K228D_C230G/CL_D122K (CS), or the combination of (i) and (ii).

| HC1[a] | LC1[b] | HC2[a] | LC2[b] | % Correct IgG BsAb w/Std.Dev. | P-value (One-tailed paired t-test) |
|---|---|---|---|---|---|
| \multicolumn{6}{c}{Anti-HER2(pertuzumab) X Anti-EGFR(matuzumab) IgG Compression} | | | | | |
| (−)PG1 AB2133a | Pκ AB2133a | (+)MG1 H4WT | Mκ H4WT | 75.1 ± 6.1 (n = 3) | |
| (−)PG1 AB2133a | Pκ AB2133a | (+)MG1 H4WT + CS | Mκ H4WT + CS | 68.4 ± 4.0 (n = 3) | Failed |
| (−)PG1 AB2133a | Pκ AB2133a | (+)MG1 H4WT + DR | Mκ H4WT + DR | 88.9 ± 6.0 (n = 3) | P = 0.06 |
| (−)PG1 AB2133a | Pκ AB2133a | (+)MG1 H4WT + CS + DR | Mκ H4WT + CS + DR | 84.4 ± 4.1 (n = 3) | P = 0.02 |
| \multicolumn{6}{c}{Anti-HER2(pertuzumab) X Anti-HER2(trastuzumab) IgG Coexpression} | | | | | |
| (−)PG1 AB2133a | Pκ AB2133a | (+)TG1 H4WT | Tκ H4WT | 69.7 ± 5.3 (n = 5) | |
| (−)PG1 AB2133a | Pκ AB2133a | (+)TG1 H4WT + CS | Tκ H4WT + CS | 71.7 ± 6.7 (n = 5) | P = 0.30 |
| (−)PG1 AB2133a | Pκ AB2133a | (+)TG1 H4WT + DR | Tκ H4WT + DR | 70.2 ± 3.8 (n = 5) | P = 0.28 |
| (−)PG1 AB2133a | Pκ AB2133a | (+)TG1 H4WT + CS + DR | Tκ H4WT + CS + DR | 79.6 ± 4.2 (n = 5) | P < 0.0001 |
| \multicolumn{6}{c}{Anti-HER2(pertuzumab) X Anti-HER2(trastuzumab) IgG Coexpression with H4WT and AB2133a swapped} | | | | | |
| (+)PG1 H4WT | Pκ H4WT | (−)TG1 AB2133a | Tκ AB2133a | 35.4 ± 10.1 (n = 5) | |
| (+)PG1 H4WT + CS | Pκ H4WT + CS | (−)TG1 AB2133a | Tκ AB2133a | 41.7 ± 16.8 (n = 5) | P = 0.07 |
| (+)PG1 H4WT + DR | Pκ H4WT + DR | (−)TG1 AB2133a | Tκ AB2133a | 52.0 ± 9.0 (n = 5) | P = 0.003 |
| (+)PG1 H4WT + CS + DR | Pκ H4WT + CS + DR | (−)TG1 AB2133a | Tκ AB2133a | 47.6 ± 15.1 (n = 5) | P = 0.01 |

[a]The HC designs with (−) contained the K409D and K392D mutations while the HC designs with the (+) contained the D399K and E356K mutations. Both the (+) and (−) - containing HCs also have the N297Q mutation to eliminate N-linked glycosylation. [b]All light chains in Table 19 were fully kappa (i.e., VκCκ).

As with the data in Example 8, it was clear from the data in Table 19 that the AB2133a designs did not provide the same degree of specificity when using fully kappa LCs (VκCκ).

The data in Table 19 demonstrate trends showing that both the 'DR' and 'CS' designs, when added to the H4WT-containing Fab, generally improve the specificity of correct HC/LC pairing within IgG bispecific antibodies expressed in a single cell. In a few cases, the individual 'CS' or 'DR' were found to significantly improve (i.e., P≤0.05) the correct assembly. However, when the two designs were combined ('CS+DR'), the improvements in correct HC/LC pairing specificity were statistically significant for all groups. Improvements in specificity were observed when the designs were placed on the H4WT-side of the IgG BsAb.

Overall the designs described in Example 8 and Example 9 can be utilized to improve the HC/LC pairing stability and specificity within IgG bispecific antibodies. This was particularly evident when both LCs of the IgG bispecific antibody were fully kappa; a scenario where the AB2133a designs provide less specificity than when the AB2133a designs are used within a VκCλ LC.

Sequences:
(mutations denoted by underlined, bold-face type)
SEQ ID NO. 1:
PERTUZUMAB HC (pG1)
EVQLVESGGGLVQPGGSLRLSCAASGFTFTDYTMDWVRQAPGKGLEWVA

DVNPNSGGSIYNQRFKGRFILSVDRSKNTLYLQMNSLRAEDTAVYYCAR

NLGPSFYFDYWGQGTLVTVSSASTKGPSVFPLAPSSKSTSGGTAALGCL

VKDYFPEPVTVSWNSGALTSGVHTFPAVLQSSGLYSLSSVVTVPSSSLG

TQTYICNVNHKPSNTKVDKKVEPKSCDKTHTCPPCPAPELLGGPSVFLF

PPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKG

QPREPQVYTLPPSRDELTKNQVSLTCLVKGFYPSDIAVEWESNGQPENN

YKTTPPVLDSDGSFFLYSKLTVDKSRWQQGNVFSCSVMHEALHNHYTQK

SLSLSPG

SEQ ID NO. 2:
PERTUZUMAB LC (pλ, KAPPA V_L/LAMBDA C_L)
DIQMTQSPSSLSASVGDRVTITCKASQDVSIGVAWYQQKPGKAPKLLIY

SASYRYTGVPSRFSGSGSGTDFTLTISSLQPEDFATYYCQQYYTYPYTF

GQGTKVEIKGQPKAAPSVTLFPPSSEELQANKATLVCLISDFYPGAVTV

AWKADSSPVKAGVETTTPSKQSNNKYAASSYLSLTPEQWKSHRSYSCQV

THEGSTVEKTVAPTEC

SEQ ID NO. 3:
HUMAN HC (MINUS VARIABLE DOMAINS) WILD-TYPE CONSTRUCT
ASTKGPSVFPLAPSSKSTSGGTAALGCLVKDYFPEPVTVSWNSGALTSG

```
VHTFPAVLQSSGLYSLSSVVTVPSSSLGTQTYICNVNHKPSNTKVDKKV

EPKSCDKTHTCPPCPAPELLGGPSVFLFPPKPKDTLMISRTPEVTCVVV

DVSHEDPEVKFNWYVDGVEVHNAKTKPREEQYNSTYRVVSVLTVLHQDW

LNGKEYKCKVSNKALPAPIEKTISKAKGQPREPQVYTLPPSRDELTKNQ

VSLTCLVKGFYPSDIAVEWESNGQPENNYKTTPPVLDSDGSFPLYSKLT

VDKSRWQQGNVFSCSVMHEALHNHYTQKSLSLSPG

SEQ ID NO: 4:
LAMBDA C_L DOMAIN
GQPKAAPSVTLFPPSSEELQANKATLVCLISDFYPGAVTVAWKADSSPV

KAGVETTTPSKQSNNKYAASSYLSLTPEQWKSHRSYSCQVTHEGSTVEK

TVAPTEC

SEQ ID NO. 5:
HC DESIGN 1.0
EVQLVESGGGLVQPGGSLRLSCAASGFTFTDYTMDWVRQAPGKGLEWVA

DVNPNSGGSIYNQRFKGRFILSVDRSKNTLYLQMNSLRAEDTAVYYCAR

NLGPSFYFDYWGQGTLVTVSSASTKGPSVFPLAPSSKSTSGGTAALGCL

VKDYFPEPVTVSWNSGALTSGVHTTPAVLQSSGLYSLSSFVTVPSSSLG

TQTYICNVNHKPSNTKVDKKVEPKSCDKTHTCPPCPAPELLGGPSVFLF

PPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKG

QPREPQVYTLPPSRDELTKNQVSLTCLVKGFYPSDIAVEWESNGQPENN

YKTTPPVLDSDGSFFLYSKLTVDKSRWQQGNVFSCSVMHEALHNHYTQK

SLSLSPG

SEQ ID NO. 6:
LC CHAIN DESIGN 1.0
DIQMTQSPSSLSASVGDRVTITCKASQDVSIGVAWYQQKPGKAPKLLIY

SASYRYTGVPSRFSGSGSGTDFTLTISSLQPEDFATYYCQQYYTYPYTF

GQGTKVEIKGQPKAAPSVTLFPPSSEELQANKATLVCFISDFYPGAVTV

AWKADSSPVKAGVETTTPSKQSNNKYAASSYLSLTPEQWKSHRSYSCQV

THEGSTVEKTVAPTEC

SEQ ID NO. 7:
HC minus V_H DESIGN 2.1, 2.1.2.1, 2.1.2.2
ASTKGPSVFPLAPSSKSTSGGTAALGCLVKDYFPEPVTVSWNSGALTSG

VHTGPAVLQSSGLYSLSSVVTVPSSSLGTQTYICNVNHKPSNTKVDKKV

EPKSCDKTHTCPPCPAPELLGGPSVFLFPPKPKDTLMISRTPEVTCVVV

DVSHEDPEVKFNWYVDGVEVHNAKTKPREEQYNSTYRVVSVLTVLHQDW

LNGKEYKCKVSNKALPAPIEKTISKAKGQPREPQVYTLPPSRDELTKNQ

VSLTCLVKGFYPSDIAVEWESNGQPENNYKTTPPVLDSDGSFPLYSKLT

VDKSRWQQGNVFSCSVMHEALHNHYTQKSLSLSPG

SEQ ID NO. 8:
C_L DESIGN 2.1, 2.1.1.1, AND 2.1.1.2
GQPKAAPSVTLFPPSSEELQANKATLVCAISDFYPGAVTVAWKADSSPV

KAGVETTTPSKQSNNKYAAWSYLSLTPEQWKSHRSYSCQVTHEGSTVEK

TVAPTEC

SEQ ID NO. 9:
HC DESIGN 5.0
EVQLVESGGGLVQPGGSLRLSCAASGFTFTDYTMDWVRQAPGKGLEWVA

DVNPNSGGSIYNQRFKGRFILSVDRSKNTLYLQMNSLRAEDTAVYYCAR

NLGPSFYFDYWGQGTLVTVSSASTKGPSVFPLAPSSKSTSGGTAALGCL

VKKYFPEPVTVSWNSGALTSGVHTFPAVLQSSGLYSLSSVVTVPSSSLG

TQTYICNVNHKPSNTKVDKKVEPKSCDKTHTCPPCPAPELLGGPSVFLF

PPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKG

QPREPQVYTLPPSRDELTKNQVSLTCLVKGFYPSDIAVEWESNGQPENN

YKTTPPVLDSDGSFFLYSKLTVDKSRWQQGNVFSCSVMHEALHNHYTQK

SLSLSPG

SEQ ID NO. 10:
LC DESIGN 5.0
DIQMTQSPSSLSASVGDRVTITCKASQDVSIGVAWYQQKPGKAPKLLIY

SASYRYTGVPSRFSGSGSGTDFTLTISSLQPEDFATYYCQQYYTYPYTF

GQGTKVEIKGQPKAAPSVTLFPPSSEELQANDATLVCLISDFYPGAVTV

AWKADSSPVKAGVETTTPSKQSNNKYAASSYLSLTPEQWKSHRSYSCQV

THEGSTVEKTVAPTEC

SEQ ID NO. 11:
HC minus V_H DESIGN 1.0 + 5.0
ASTKGPSVFPLAPSSKSTSGGTAALGCLVKKYFPEPVTVSWNSGALTSG

VHTTPAVLQSSGLYSLSSFVTVPSSSLGTQTYICNVNHKPSNTKVDKKV

EPKSCDKTHTCPPCPAPELLGGPSVFLFPPKPKDTLMISRTPEVTCVVV

DVSHEDPEVKFNWYVDGVEVHNAKTKPREEQYNSTYRVVSVLTVLHQDW

LNGKEYKCKVSNKALPAPIEKTISKAKGQPREPQVYTLPPSRDELTKNQ

VSLTCLVKGFYPSDIAVEWESNGQPENNYKTTPPVLDSDGSFPLYSKLT

VDKSRWQQGNVFSCSVMHEALHNHYTQKSLSLSPG

SEQ ID NO. 12:
C_L DESIGN 1.0 + 5.0
GQPKAAPSVTLFPPSSEELQANDATLVCFISDFYPGAVTVAWKADSSPV

KAGVETTTPSKQSNNKYAASSYLSLTPEQWKSHRSYSCQVTHEGSTVEK

TVAPTEC

SEQ ID NO. 13:
AB2133a(-)pG1 (Design AB2.1.3.3a in (-)pG1 HC)
EVQLVESGGGLVQPGGSLRLSCAASGFTFTDYTMDWVRKAPGKGLEWVA

DVNPNSGGSIYNQEFKGRFILSVDRSKNTLYLQMNSLRAEDTAVYYCAR

NLGPSFYFDYWGQGTLVTVSSASTKGPSVFPLAPSSKSTSGGTAALGCL

VKDYFPEPVTVSWNSGALTSGVATG**PAVLQSSGLYSLSSVVTVPSSSLG

TQTYICNVNHKPSNTKVDKKVEPKSCDKTHTCPPCPAPELLGGPSVFLF

PPKPKDTLMISRTPEVTCVVVDVSHEDPEVKFNWYVDGVEVHNAKTKPR

EEQYQSTYRVVSVLTVLHQDWLNGKEYKCKVSNKALPAPIEKTISKAKG

QPREPQVYTLPPSRDELTKNQVSLTCLVKGFYPSDIAVEWESNGQPENN

YDTTPPVLDSDGSFFLYSDLTVDKSRWQQGNVFSCSVMHEALHNHYTQK

SLSLSPG

SEQ ID NO. 14:
H.4WTAx1κ (anti-Ax1 LC with H.4 V_L and
wild-type C_κ)
DIQMTQSPSSLSASVGDRVTITCKASQDVSIGVAWYQRKPGKAPKLLIY
```

SASYRYTGVPSRFSGSGSGTDFTLTISSLQPEDFATYYCQQYYTYPYTF

GQGTKVEIKGQPKAAPSVTLFPPSSEELQANKATLVCLISDFYPGAVTV

AWKADSSPVKAGVETTTPSKQSNNKYAASSYLSLTPEQWKSHRSYSCQV

THEGSTVEKTVAPTEC

SEQ ID NO. 15:
C_L DESIGN 2.1.3.2
GQPKAAPSVTLFPPSSEELQANKATLVCFISDFYPGAVTVAWKADSSPV

KAGVETTTPSKQSNNKYAAWSYLSLTPEQWKSHRSYSCQVTHEGSTVEK

TVAPTEC

SEQ ID NO. 16:
H.4WTAx1λ (anti-Ax1 LC with H.4 V_L and
wild-type C_λ)
DIQMTQSPSSLSASVGDRVTITCKASQDVSIGVAWYQRKPGKAPKLLIY

SASYRYTGVPSRFSGSGSGTDFTLTISSLQPEDFATYYCQQYYTYPYTF

GQGTKVEIKGQPKAAPSVTLFPPSSEELQANKATLVCLISDFYPGAVTV

AWKADSSPVKAGVETTTPSKQSNNKYAASSYLSLTPEQWKSHRSYSCQV

THEGSTVEKTVAPTEC

SEQ ID NO. 17:
H.4WT(+)Ax1G1 (Design H.4 in (+)Ax1G1 HC)
EVQLVESGGGLVQPGGSLRLSCAASGFSLSGSWIHWVRYAPGKGLEWVG

WINPYRGYAYYADSVKGRFTISADTSKNTAYLQMNSLRAEDTAVYYCAR

EYSGWGGSSVGYAMDYWGQGTLVTVSSASTKGPSVFPLAPSSKSTSGGT

AALGCLVKDYFPEPVTVSWNSGALTSGVHTFPAVLQSSGLYSLSSVVTV

PSSSLGTQTYICNVNHKPSNTKVDKKVEPKSCDKTHTCPPCPAPELLGG

PSVFLFPPKPKDTLMISRTPEVTCVVVDVSHEDPEVKFNWYVDGVEVHN

AKTKPREEQYQSTYRVVSVLTVLHQDWLNGKEYKCKVSNKALPAPIEKT

ISKAKGQPREPQVYTLPPSRKELTKNQVSLTCLVKGFYPSDIAVEWESN

GQPENNYKTTPPVLKSDGSFFLYSKLTVDKSRWQQGNVFSCSVMHEALH

NHYTQKSLSLSPG

SEQ ID NO. 18:
HC minus V_H DESIGN 2.1.3.2 AND 2.1.3.3A
ASTKGPSVFPLAPSSKSTSGGTAALGCLVKDYFPEPVTVSWNSGALTSG

VATGPAVLQSSGLYSLSSVVTVPSSSLGTQTYICNVNHKPSNTKVDKKV

EPKSCDKTHTCPPCPAPELLGGPSVFLFPPKPKDTLMISRTPEVTCVVV

DVSHEDPEVKFNWYVDGVEVHNAKTKPREEQYNSTYRVVSVLTVLHQDW

LNGKEYKCKVSNKALPAPIEKTISKAKGQPREPQVYTLPPSRDELTKNQ

VSLTCLVKGFYPSDIAVEWESNGQPENNYKTTPPVLDSDGSFFLYSKLT

VDKSRWQQGNVFSCSVMHEALHNHYTQKSLSLSPG

SEQ ID NO. 19:
HC minus V_H DESIGN 2.1.3.3
ASTKGPSVFPLAPSSKSTSGGTAALGCLVKDYFPEPVTVSWNSGALTSG

VSTGPAVLQSSGLYSLSSVVTVPSSSLGTQTYICNVNHKPSNTKVDKKV

EPKSCDKTHTCPPCPAPELLGGPSVFLFPPKPKDTLMISRTPEVTCVVV

DVSHEDPEVKFNWYVDGVEVHNAKTKPREEQYNSTYRVVSVLTVLHQDW

LNGKEYKCKVSNKALPAPIEKTISKAKGQPREPQVYTLPPSRDELTKNQ

VSLTCLVKGFYPSDIAVEWESNGQPENNYKTTPPVLDSDGSFFLYSKLT

VDKSRWQQGNVFSCSVMHEALHNHYTQKSLSLSPG

SEQ ID NO. 20:
C_L DESIGN 2.1.3.3 AND 2.1.3.3A
GQPKAAPSVTLFPPSSEELQANKATLVCYISDFYPGAVTVAWKADSSPV

KAGVETTTPSKQNNKYAAWSYLSLTPEQWKSHRSYSCQVTHEGSTVEKT

VAPTEC

SEQ ID NO. 21:
HC DESIGN A
EVQLVESGGGLVQPGGSLRLSCAASGFTFTDYTMDWVRQAPGKGLEWVA

DVNPNSGGSIYNQEFKGRFTLSVDRSKNTLYLQMNSLRAEDTAVYYCAR

NLGPSFYFDYWGQGTLVTVSSASTKGPSVFPLAPSSKSTSGGTAALGCL

VKDYFPEPVTVSWNSGALTSGVHTFPAVLQSSGLYSLSSVVTVPSSSLG

TQTYICNVNHKPSNTKVDKKVEPKSCDKTHTCPPCPAPELLGGPSVFLF

PPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKG

QPREPQVYTLPPSRDELTKNQVSLTCLVKGFYPSDIAVEWESNGQPENN

YKTTPPVLDSDGSFFLYSKLTVDKSRWQQGNVFSCSVMHEALHNHYTQK

SLSLSPG

SEQ ID NO. 22:
LC DESIGN A
RIQMTQSPSSLSASVGDRVTITCKASQDVSIGVAWYQQKPGKAPKLLIY

SASYRYTGVPSRFSGSGSGTDFTLTISSLQPEDFATYYCQQYYIYPYTF

GQGTKVEIKGQPKAAPSVTLFPPSSEELQANKATLVCLISDFYPGAVTV

AWKADSSPVKAGVETTTPSKQSNNKYAASSYLSLTPEQWKSHRSYSCQV

THEGSTVEKTVAPTEC

SEQ ID NO. 23:
HC DESIGN B
EVQLVESGGGLVQPGGSLRLSCAASGFTFTDYTMDWVRKAPGKGLEWVA

DVNPNSGGSIYNQRFKGRFTLSVDRSKNTLYLQMNSLRAEDTAVYYCAR

NLGPSFYFDYWGQGTLVTVSSASTKGPSVFPLAPSSKSTSGGTAALGCL

VKDYFPEPVTVSWNSGALTSGVHTFPAVLQSSGLYSLSSVVTVPSSSLG

TQTYICNVNHKPSNTKVDKKVEPKSCDKTHTCPPCPAPELLGGPSVFLF

PPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKG

QPREPQVYTLPPSRDELTKNQVSLTCLVKGFYPSDIAVEWESNGQPENN

YKTTPPVLDSDGSFFLYSKLTVDKSRWQQGNVFSCSVMHEALHNHYTQK

SLSLSPG

SEQ ID NO. 24:
LC DESIGN B
DIQMTQSPSSLSASVGDRVTITCKASQDVSIGVAWYQDKPGKAPKLLIY

SASYRYTGVPSRFSGSGSGTDFTLTISSLQPEDFATYYCQQYYIYPYTF

GQGTKVEIKGQPKAAPSVTLFPPSSEELQANKATLVCLISDFYPGAVTV

AWKADSSPVKAGVETTTPSKQSNNKYAASSYLSLTPEQWKSHRSYSCQV

THEGSTVEKTVAPTEC

```
SEQ ID NO. 25:
HC DESIGN AB
EVQLVESGGGLVQPGGSLRLSCAASGFTFTDYTMDWVRKAPGKGLEWVA
DVNPNSGGSIYNQEFKGRFTLSVDRSKNTLYLQMNSLRAEDTAVYYCAR
NLGPSFYFDYWGQGTLVTVSSASTKGPSVFPLAPSSKSTSGGTAALGCL
VKDYFPEPVTVSWNSGALTSGVHTFPAVLQSSGLYSLSSVVTVPSSSLG
TQTYICNVNHKPSNTKVDKKVEPKSCDKTHTCPPCPAPELLGGPSVFLF
PPKPKDTLMISRTPEVTCVVVDVSHEDPEVKFNWYVDGVEVHNAKTKPR
EEQYNSTYRVVSVLTVLHQDWLNGKEYKCKVSNKALPAPIEKTISKAKG
QPREPQVYTLPPSRDELTKNQVSLTCLVKGFYPSDIAVEWESNGQPENN
YKTTPPVLDSDGSFFLYSKLTVDKSRWQQGNVFSCSVMHEALHNHYTQK
SLSLSPG

SEQ ID NO. 26:
LC DESIGN AB
RIQMTQSPSSLSASVGDRVTITCKASQDVSIGVAWYQDKPGKAPKLLIY
SASYRYTGVPSRFSGSGSGTDFTLTISSLQPEDFATYYCQQYYIYPYTF
GQGTKVEIKGQPKAAPSVTLFPPSSEELQANKATLVCLISDFYPGAVTV
AWKADSSPVKAGVETTTPSKQSNNKYAASSYLSLTPEQWKSHRSYSCQV
THEGSTVEKTVAPTEC

SEQ ID NO. 27:
HC DESIGN 1.0 + 5.0
EVQLVESGGGLVQPGGSLRLSCAASGFTFTDYTMDWVRQAPGKGLEWVA
DVNPNSGGSIYNQRFKGRFTLSVDRSKNTLYLQMNSLRAEDTAVYYCAR
NLGPSFYFDYWGQGTLVTVSSASTKGPSVFPLAPSSKSTSGGTAALGCL
VKKYFPEPVTVSWNSGALTSGVHTTPAVLQSSGLYSLSSFVTVPSSSLG
TQTYICNVNHKPSNTKVDKKVEPKSCDKTHTCPPCPAPELLGGPSVFLF
PPKPKDTLMISRTPEVTCVVVDVSHEDPEVKFNWYVDGVEVHNAKTKPR
EEQYNSTYRVVSVLTVLHQDWLNGKEYKCKVSNKALPAPIEKTISKAKG
QPREPQVYTLPPSRDELTKNQVSLTCLVKGFYPSDIAVEWESNGQPENN
YKTTPPVLDSDGSFFLYSKLTVDKSRWQQGNVFSCSVMHEALHNHYTQK
SLSLSPG

SEQ ID NO. 28:
LC DESIGN 1.0 + 5.0
DIQMTQSPSSLSASVGDRVTITCKASQDVSIGVAWYQQKPGKAPKLLIY
SASYRYTGVPSRFSGSGSGTDFTLTISSLQPEDFATYYCQQYYIYPYTF
GQGTKVEIKGQPKAAPSVTLFPPSSEELQANDATLVCFISDFYPGAVTV
AWKADSSPVKAGVETTTPSKQSNNKYAASSYLSLTPEQWKSHRSYSCQV
THEGSTVEKTVAPTEC

SEQ ID NO. 29:
HC DESIGN H.4
EVQLVESGGGLVQPGGSLRLSCAASGFTFTDYTMDWVRYAPGKGLEWVA
DVNPNSGGSIYNQRFKGRFTLSVDRSKNTLYLQMNSLRAEDTAVYYCAR
NLGPSFYFDYWGQGTLVTVSSASTKGPSVFPLAPSSKSTSGGTAALGCL
VKDYFPEPVTVSWNSGALTSGVHTFPAVLQSSGLYSLSSVVTVPSSSLG
TQTYICNVNHKPSNTKVDKKVEPKSCDKTHTCPPCPAPELLGGPSVFLF
PPKPKDTLMISRTPEVTCVVVDVSHEDPEVKFNWYVDGVEVHNAKTKPR
EEQYNSTYRVVSVLTVLHQDWLNGKEYKCKVSNKALPAPIEKTISKAKG
QPREPQVYTLPPSRDELTKNQVSLTCLVKGFYPSDIAVEWESNGQPENN
YKTTPPVLDSDGSFFLYSKLTVDKSRWQQGNVFSCSVMHEALHNHYTQK
SLSLSPG

SEQ ID NO. 30:
LC DESIGN H.4, H.5, H.6 LAMBDA
DIQMTQSPSSLSASVGDRVTITCKASQDVSIGVAWYQRKPGKAPKLLIY
SASYRYTGVPSRFSGSGSGTDFTLTISSLQPEDFATYYCQQYYIYPYTF
GQGTKVEIKGQPKAAPSVTLFPPSSEELQANKATLVCLISDFYPGAVTV
AWKADSSPVKAGVETTTPSKQSNNKYAASSYLSLTPEQWKSHRSYSCQV
THEGSTVEKTVAPTEC

SEQ ID NO. 31:
HC DESIGN H.5
EVQLVESGGGLVQPGGSLRLSCAASGFTFTDYTMDWVRFAPGKGLEWVA
DVNPNSGGSIYNQRFKGRFTLSVDRSKNTLYLQMNSLRAEDTAVYYCAR
NLGPSFYFDYWGQGTLVTVSSASTKGPSVFPLAPSSKSTSGGTAALGCL
VKDYFPEPVTVSWNSGALTSGVHTFPAVLQSSGLYSLSSVVTVPSSSLG
TQTYICNVNHKPSNTKVDKKVEPKSCDKTHTCPPCPAPELLGGPSVFLF
PPKPKDTLMISRTPEVTCVVVDVSHEDPEVKFNWYVDGVEVHNAKTKPR
EEQYNSTYRVVSVLTVLHQDWLNGKEYKCKVSNKALPAPIEKTISKAKG
QPREPQVYTLPPSRDELTKNQVSLTCLVKGFYPSDIAVEWESNGQPENN
YKTTPPVLDSDGSFFLYSKLTVDKSRWQQGNVFSCSVMHEALHNHYTQK
SLSLSPG

SEQ ID NO. 32:
HC DESIGN H.6
EVQLVESGGGLVQPGGSLRLSCAASGFTFTDYTMDWVRWAPGKGLEWVA
DVNPNSGGSIYNQRFKGRFTLSVDRSKNTLYLQMNSLRAEDTAVYYCAR
NLGPSFYFDYWGQGTLVTVSSASTKGPSVFPLAPSSKSTSGGTAALGCL
VKDYFPEPVTVSWNSGALTSGVHTFPAVLQSSGLYSLSSVVTVPSSSLG
TQTYICNVNHKPSNTKVDKKVEPKSCDKTHTCPPCPAPELLGGPSVFLF
PPKPKDTLMISRTPEVTCVVVDVSHEDPEVKFNWYVDGVEVHNAKTKPR
EEQYNSTYRVVSVLTVLHQDWLNGKEYKCKVSNKALPAPIEKTISKAKG
QPREPQVYTLPPSRDELTKNQVSLTCLVKGFYPSDIAVEWESNGQPENN
YKTTPPVLDSDGSFFLYSKLTVDKSRWQQGNVFSCSVMHEALHNHYTQK
SLSLSPG

SEQ ID NO. 33:
LC PERTUZUMAB KAPPA (pκ, KAPPA $V_L$/KAPPA $C_L$)
DIQMTQSPSSLSASVGDRVTITCKASQDVSIGVAWYQQKPGKAPKLLIY
SASYRYTGVPSRFSGSGSGTDFTLTISSLQPEDFATYYCQQYYIYPYTF
GQGTKVEIKRTVAAPSVFIFPPSDEQLKSGTASVVCLLNNFYPREAKVQ
WKVDNALQSGNSQESVTEQDSKDSTYSLSSTLTLSKADYEKHKVYACEV
THQGLSSPVTKSFNRGEC

SEQ ID NO. 34:
LC DESIGN AB KAPPA
RIQMTQSPSSLSASVGDRVTITCKASQDVSIGVAWYQDKPGKAPKLLIY
```

SASYRYTGVPSRFSGSGSGTDFTLTISSLQPEDFATYYCQQYYIYPYTF

GQGTKVEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC

SEQ ID NO. 35:
HC DESIGN 2.1.3.3A
EVQLVESGGGLVQPGGSLRLSCAASGFTFTDYTMDWVRQAPGKGLEWVA

DVNPNSGGSIYNQRFKGRFTLSVDRSKNTLYLQMNSLRAEDTAVYYCAR

NLGPSFYFDYWGQGTLVTVSSASTKGPSVFPLAPSSKSTSGGTAALGCL

VKDYFPEPVTVSWNSGALTSGVATG**PAVLQSSGLYSLSSVVTVPSSSLG

TQTYICNVNHKPSNTKVDKKVEPKSCDKTHTCPPCPAPELLGGPSVFLF

PPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKG

QPREPQVYTLPPSRDELTKNQVSLTCLVKGFYPSDIAVEWESNGQPENN

YKTTPPVLDSDGSFFLYSKLTVDKSRWQQGNVFSCSVMHEALHNHYTQK

SLSLSPG

SEQ ID NO. 36:
LC DESIGN 2.1.3.3a
DIQMTQSPSSLSASVGDRVTITCKASQDVSIGVAWYQQKPGKAPKLLIY

SASYRYTGVPSRFSGSGSGTDFTLTISSLQPEDFATYYCQQYYIYPYTF

GQGTKVEIKGQPKAAPSVTLFPPSSEELQANKATLVCYISDFYPGAVTV

AWKADSSPVKAGVETTTPSKQSNNKYAAWSYLSLTPEQWKSHRSYSCQV

THEGSTVEKTVAPTEC

SEQ ID NO. 37:
HC DESIGNS AB2.1.3.3a and AB2.1.3.2
EVQLVESGGGLVQPGGSLRLSCAASGFTFTDYTMDWVRKAPGKGLEWVA

DVNPNSGGSIYNQEFKGRFTLSVDRSKNTLYLQMNSLRAEDTAVYYCAR

NLGPSFYFDYWGQGTLVTVSSASTKGPSVFPLAPSSKSTSGGTAALGCL

VKDYFPEPVTVSWNSGALTSGVATG**PAVLQSSGLYSLSSVVTVPSSSLG

TQTYICNVNHKPSNTKVDKKVEPKSCDKTHTCPPCPAPELLGGPSVFLF

PPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKG

QPREPQVYTLPPSRDELTKNQVSLTCLVKGFYPSDIAVEWESNGQPENN

YKTTPPVLDSDGSFFLYSKLTVDKSRWQQGNVFSCSVMHEALHNHYTQK

SLSLSPG

SEQ ID NO. 38:
LC DESIGN AB2.1.3.3a (AB2133apλ)
RIQMTQSPSSLSASVGDRVTITCKASQDVSIGVAWYQDKPGKAPKLLIY

SASYRYTGVPSRFSGSGSGTDFTLTISSLQPEDFATYYCQQYYIYPYTF

GQGTKVEIKGQPKAAPSVTLFPPSSEELQANKATLVCYISDFYPGAVTV

AWKADSSPVKAGVETTTPSKQSNNKYAAWSYLSLTPEQWKSHRSYSCQV

THEGSTVEKTVAPTEC

SEQ ID NO. 39:
HC DESIGN H.42.1.3.3a
EVQLVESGGGLVQPGGSLRLSCAASGFTFTDYTMDWVRYAPGKGLEWVA

DVNPNSGGSIYNQRFKGRFTLSVDRSKNTLYLQMNSLRAEDTAVYYCAR

NLGPSFYFDYWGQGTLVTVSSASTKGPSVFPLAPSSKSTSGGTAALGCL

VKDYFPEPVTVSWNSGALTSGVATG**PAVLQSSGLYSLSSVVTVPSSSLG

TQTYICNVNHKPSNTKVDKKVEPKSCDKTHTCPPCPAPELLGGPSVFLF

PPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKG

QPREPQVYTLPPSRDELTKNQVSLTCLVKGFYPSDIAVEWESNGQPENN

YKTTPPVLDSDGSFFLYSKLTVDKSRWQQGNVFSCSVMHEALHNHYTQK

SLSLSPG

SEQ ID NO. 40:
LC DESIGN H.42.1.3.3a
DIQMTQSPSSLSASVGDRVTITCKASQDVSIGVAWYQRKPGKAPKLLIY

SASYRYTGVPSRFSGSGSGTDFTLTISSLQPEDFATYYCQQYYIYPYTF

GQGTKVEIKGQPKAAPSVTLFPPSSEELQANKATLVCYISDFYPGAVTV

AWKADSSPVKAGVETTTPSKQSNNKYAAWSYLSLTPEQWKSHRSYSCQV

THEGSTVEKTVAPTEC

SEQ ID NO. 41:
HC DESIGN H.4 KAPPA
DIQMTQSPSSLSASVGDRVTITCKASQDVSIGVAWYQRKPGKAPKLLIY

SASYRYTGVPSRFSGSGSGTDFTLTISSLQPEDFATYYCQQYYIYPYTF

GQGTKVEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSENRGEC

SEQ ID NO. 42:
LC DESIGN AB2.1.3.2
RIQMTQSPSSLSASVGDRVTITCKASQDVSIGVAWYQDKPGKAPKLLIY

SASYRYTGVPSRFSGSGSGTDFTLTISSLQPEDFATYYCQQYYIYPYTF

GQGTKVEIKGQPKAAPSVTLFPPSSEELQANKATLVCFISDFYPGAVTV

AWKADSSPVKAGVETTTPSKQSNNKYAAWSYLSLTPEQWKSHRSYSCQV

THEGSTVEKTVAPTEC

SEQ ID NO. 43:
Matuzumab HC (mG1)
QVQLVQSGAEVKKPGASVKVSCKASGYTFTSHWMHWVRQAPGQGLEWIG

EFNPSNGRTNYNEKFKSKATMTVDTSTNTAYMELSSLRSEDTAVYYCAS

RDYDYDGRYFDYWGQGTLVTVSSASTKGPSVFPLAPSSKSTSGGTAALG

CLVKDYFPEPVTVSWNSGALTSGVHTFPAVLQSSGLYSLSSVVTVPSSS

LGTQTYICNVNHKPSNTKVDKKVEPKSCDKTHTCPPCPAPELLGGPSVF

LFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKA

KGQPREPQVYTLPPSRDELTKNQVSLTCLVKGFYPSDIAVEWESNGQPE

NNYKTTPPVLDSDGSFFLYSKLTVDKSRWQQGNVFSCSVMHEALHNHYT

QKSLSLSPG

SEQ ID NO. 44:
Matuzumab LC (mλ, V$_L$ and lambda C$_L$ [C$_λ$])
DIQMTQSPSSLSASVGDRVTITCSASSSVTYMYWYQQKPGKAPKLLIYD

TSNLASGVPSRFSGSGSGTDYTFTISSLQPEDIATYYCQQWSSHIFTFG

QGTKVEIKGQPKAAPSVTLFPPSSEELQANKATLVCLISDFYPGAVTVA

WKADSSPVKAGVETTTPSKQSNNKYAASSYLSLTPEQWKSHRSYSCQVT

HEGSTVEKTVAPTEC

SEQ ID NO. 45:
Matuzumab LC (mκ, V$_L$ and kappa C$_L$ [C$_κ$])
DIQMTQSPSSLSASVGDRVTITCSASSSVTYMYWYQQKPGKAPKLLIYD

TSNLASGYPSRFSGSGSGTDYTFTISSLQPEDIATYYCQQWSSHIFTFG

QGTKVEIKRTVAAPSVFIFPPSDEQLKSGTASVVCLLNNFYPREAKVQW

KVDNALQSGNSQESVTEQDSKDSTYSLSSTLTLSKADYEKHKVYACEVT

HQGLSSPVTKSFNRGEC

SEQ ID NO. 46:
METMAb HC (METG1)
EVQLVESGGGLVQPGGSLRLSCAASGYTFTSYWLHWVRKAPGKGLEWVG

MIDPSNSDTRFNPNFKDRFTISADTSKNTAYLQMNSLRAEDTAVYYCAT

YRSYVTPLDYWGQGTLVTVSSASTKGPSVFPLAPSSKSTSGGTAALGCL

VKDYFPEPVTVSWNSGALTSGVHTFPAVLQSSGLYSLSSVVTVPSSSLG

TQTYICNVNHKPSNTKVDKKVEPKSCDKTHTCPPCPAPELLGGPSVFLF

PPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKG

QPREPQVYTLPPSRDELTKNQVSLTCLVKGFYPSDIAVEWESNGQPENN

YKTTPPVLDSDGSFFLYSKLTVDKSRWQQGNVFSCSVMHEALHNHYTQK

SLSLSPG

SEQ ID NO. 47:
METMAb LC (METλ, kappa V$_L$ and lambda C$_L$ [C$_λ$])
DIQMTQSPSSLSASVGDRVTITCKSSQSLLYTSSQKNYLAWYQQKPGKA

PKLLIYWASTRESGVPSRFSGSGSGTDFTLTISSLQPEDFATYYCQQYY

AYPWTFGQGTKVEIKGQPKAAPSVTLFPPSSEELQANKATLVCLISDFY

PGAVTVAWKADSSPVKAGVETTTPSKQSNNKYAASSYLSLTPEQWKSHR

SYSCQVTHEGSTVEKTVAPTEC

SEQ ID NO. 48:
METMAb LC (METκ, kappa V$_L$ and kappa C$_L$ [C$_κ$])
DIQMTQSPSSLSASVGDRVTITCKSSQSLLYTSSQKNYLAWYQQKPGKA

PKILIYWASTRESGVPSRFSGSGSGTDFTLTISSLQPEDFATYYCQQYY

AYPWTFGQGTKVEIKRTVAAPSVFIFPPSDEQLKSGTASVVCLLNNFYP

REAKVQWKVDNALQSGNSQESVTEQDSKDSTYSLSSTLTLSKADYEKHK

VYACEVTHQGLSSPVTKSFNRGEC

SEQ ID NO. 49:
anti-Ax1 HC (Ax1G1)
EVQLVESGGGLVQPGGSLRLSCAASGFSLSGSWIHWVRQAPGKGLEWVG

WINPYRGYAYYADSVKGRFTISADTSKNTAYLQMNSLRAEDTAVYYCAR

EYSGWGGSSVGYAMDYWGQGTLVTVSSASTKGPSVFPLAPSSKSTSGGT

AALGCLVKDYFPEPVTVSWNSGALTSGVHTFPAVLQSSGLYSLSSVVTV

PSSSLGTQTYICNVNHKPSNTKVDKKVEPKSCDKTHTCPPCPAPELLGG

PSVFLFPPKPKDTLMISRTPEVTCVVVDVSHEDPEVKFNWYVDGVEVHN

AKTKPREEQYNSTYRVVSVLTVLHQDWLNGKEYKCKVSNKALPAPIEKT

ISKAKGQPREPQVYTLPPSRDELTKNQVSLTCLVKGFYPSDIAVEWESN

GQPENNYKTTPPVLDSDGSFFLYSKLTVDKSRWQQGNVFSCSVMHEALH

NHYTQKSLSLSPG

SEQ ID NO. 50:
anti-Ax1 LC (Ax1λ, kappa V$_L$ and lambda C$_L$ [C$_λ$])
DIQMTQSPSSLSASVGDRVTITCRASQDVSTAVAWYQQKPGKAPKLLIY

SASFLYSGVPSRFSGSGSGTDFTLTISSLQPEDFATYYCQQSYTTPPTF

GQGTKVEIKGQPKAAPSVTLFPPSSEELQANKATLVCLISDFYPGAVTV

AWKADSSPVKAGVETTTPSKQSNNKYAASSYLSLTPEQWKSHRSYSCQV

THEGSTVEKTVAPTEC

SEQ ID NO. 51:
anti-Ax1 LC (Ax1κ, kappa V$_L$ and kappa C$_L$ [C$_κ$])
DIQMTQSPSSLSASVGDRVTITCRASQDVSTAVAWYQQKPGKAPKLLIY

SASFLYSGVPSRFSGSGSGTDFTLTISSLQPEDFATYYCQQSYTTPPTF

GQGTKVEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC

SEQ ID NO. 52:
(-)pG1 (Pertuzumab IgG1 HC with CH3_K409D, K392D)
EVQLVESGGGLVQPGGSLRLSCAASGFTFTDYTMDWVRQAPGKGLEWVA

DVNPNSGGSIYNQRFKGRFTLSVDRSKNTLYLQMNSLRAEDTAVYYCAR

NLGPSFYFDYWGQGTLVTVSSASTKGPSVFPLAPSSKSTSGGTAALGCL

VKDYFPEPVTVSWNSGALTSGVHTFPAVLQSSGLYSLSSVVTVPSSSLG

TQTYICNVNHKPSNTKVDKKVEPKSCDKTHTCPPCPAPELLGGPSVFLF

PPKPKDTLMISRTPEVTCVVVDVSHEDPEVKFNWYVDGVEVHNAKTKPR

EEQYQSTYRVVSVLTVLHQDWLNGKEYKCKVSNKALPAPIEKTISKAKG

QPREPQVYTLPPSRDELTKNQVSLTCLVKGFYPSDIAVEWESNGQPENN

YDTTPPVLDSDGSFFLYSDLTVDKSRWQQGNVFSCSVMHEALHNHYTQK

SLSLSPG

SEQ ID NO. 53:
(+)mG1 (Matuzumab IgG1 HC with C$_H$3_D399K, E356K)
QVQLVQSGAEVKKPGASVKVSCKASGYTFTSHWMHWVRQAPGQGLEWIG

EFNPSNGRTNYNEKFKSKATMTVDTSTNTAYMELSSLRSEDTAVYYCAS

RDYDYDGRYFDYWGQGTLVTVSSASTKGPSVFPLAPSSKSTSGGTAALG

CLVKDYFPEPVTVSWNSGALTSGVHTFPAVLQSSGLYSLSSVVTVPSSS

LGTQTYICNVNHKPSNTKVDKKVEPKSCDKTHTCPPCPAPELLGGPSVF

LFPPKPKDTLMISRTPEVTCVVVDVSHEDPEVKFNWYVDGVEVHNAKTK

PREEQYQSTYRVVSVLTVLHQDWLNGKEYKCKVSNKALPAPIEKTISKA

KGQPREPQVYTLPPSRKELTKNQVSLTCLVKGFYPSDIAVEWESNGQPE

NNYKTTPPVLKSDGSFFLYSKLTVDKSRWQQGNVFSCSVMHEALHNHYT

QKSLSLSPG

SEQ ID NO. 54:
(-)METG1 (METMAb IgG1 HC with CH3_K409D, K392D)
EVQLVESGGGLVQPGGSLRLSCAASGYTFTSYWLHWVRQAPGKGLEWVG

MIDPSNSDTRFNPNFKDRFTISADTSKNTAYLQMNSLRAEDTAVYYCAT

YRSYVTPLDYWGQGTLVTVSSASTKGPSVFPLAPSSKSTSGGTAALGCL

```
VKDYFPEPVTVSWNSGALTSGVHTFPAVLQSSGLYSLSSVVTVPSSSLG

TQTYICNVNHKPSNTKVDKKVEPKSCDKTHTCPPCPAPELLGGPSVFLF

PPKPKDTLMISRTPEVTCVVVDVSHEDPEVKFNWYVDGVEVHNAKTKPR

EEQYQSTYRVVSVLTVLHQDWLNGKEYKCKVSNKALPAPIEKTISKAKG

QPREPQVYTLPPSRDELTKNQVSLTCLVKGFYPSDIAVEWESNGQPENN

YDTTPPVLDSDGSFFLYSDLTVDKSRWQQGNVFSCSVMHEALHNHYTQK

SLSLSPG

SEQ ID NO. 55:
(+)Ax1G1 (anti-Ax1 IgG1 HC with C_H3_D399K, E356K)
EVQLVESGGGLVQPGGSLRLSCAASGFSLSGSWIHWVRQAPGKGLEWVG

WINPYRGYAYYADSVKGRFTISADTSKNTAYLQMNSLRAEDTAVYYCAR

EYSGWGGSSVGYAMDYWGQGTLVTVSSASTKGPSVFPLAPSSKSTSGGT

AALGCLVKDYFPEPVTVSWNSGALTSGVHTFPAVLQSSGLYSLSSVVTV

PSSSLGTQTYICNVNHKPSNTKVDKKVEPKSCDKTHTCPPCPAPELLGG

PSVFLFPPKPKDTLMISRTPEVTCVVVDVSHEDPEVKFNWYVDGVEVHN

AKTKPREEQYQSTYRVVSVLTVLHQDWLNGKEYKCKVSNKALPAPIEKT

ISKAKGQPREPQVYTLPPSRKELTKNQVSLTCLVKGFYPSDIAVEWESN

GQPENNYKTTPPVLKSDGSFFLYSKLTVDKSRWQQGNVFSCSVMHEALH

NHYTQKSLSLSPG

SEQ ID NO. 56:
AB2133apκ (Pertuzumab LC with AB in V_L and
2.1.3.3a in C_κ)
RIQMTQSPSSLSASVGDRVTITCKASQDVSIGVAWYQDKPGKAPKLLIY

SASYRYTGVPSRFSGSGSGTDFTLTISSLQPEDFATYYCQQYYIYPYTF

GQGTKVEIKRTVAAPSVFIFPPSDEQLKSGTASVVCYLNNFYPREAKVQ

WKVDNALQSGNSQESVTEQDSKDSTYSLWSTLTLSKADYEKHKVYACEV

THQGLSSPVTKSFNRGEC

SEQ ID NO. 57:
H.4WT(+)mG1 (Design H.4 in (+)mG1 HC)
QVQLVQSGAEVKKPGASVKVSCKASGYTFTSHWMHWVRYAPGQGLEWIG

EFNPSNGRTNYNEKFKSKATMTVDTSTNTAYMELSSLRSEDTAVYYCAS

RDYDYDGRYFDYWGQGTLVTVSSASTKGPSVFPLAPSSKSTSGGTAALG

CLVKDYFPEPVTVSWNSGALTSGVHTFPAVLQSSGLYSLSSVVTVPSSS

LGTQTYICNVNHKPSNTKVDKKVEPKSCDKTHTCPPCPAPELLGGPSVF

LFPPKPKDTLMISRTPEVTCVVVDVSHEDPEVKFNWYVDGVEVHNAKTK

PREEQYQSTYRVVSVLTVLHQDWLNGKEYKCKVSNKALPAPIEKTISKA

KGQPREPQVYTLPPSRKELTKNQVSLTCLVKGFYPSDIAVEWESNGQPE

NNYKTTPPVLKSDGSFFLYSKLTVDKSRWQQGNVFSCSVMHEALHNHYT

QKSLSLSPG

SEQ ID NO. 58:
H.4WTmλ (Matuzumab LC with H.4 V_L and
wild-type C_λ)
DIQMTQSPSSLSASVGDRVTITCSASSSVTYMYWYQRKPGKAPKLLIYD

TSNLASGVPSRFSGSGSGTDYFTISSLQPEDIATYYCQQWSSHIFTFGQ

GTKVEIKGQPKAAPSVTLFPPSSEELQANKATLVCLISDFYPGAVTVAW

KADSSPVKAGVETTTPSKQSNNKYAASSYLSLTPEQWKSHRSYSCQVTH

EGSTVEKTVAPTEC

SEQ ID NO. 59:
H.4WTmκ (Matuzumab LC with H.4 V_L and
wild-type C_κ)
DIQMTQSPSSLSASVGDRVTITCSASSSVTYMYWYQRKPGKAPKLLIYD

TSNLASGVPSRFSGSGSGTDYTFTISSLQPEDIATYYCQQWSSHIFTFG

QGTKVEIKRTVAAPSVFIFPPSDEQLKSGTASVVCLLNNFYPREAKVQW

KVDNALQSGNSQESVTEQDSKDSTYSLSSTLTLSKADYEKHKVYACEVT

HQGLSSPVTKSFNRGEC

SEQ ID NO. 60:
AB2133a(-)METG1 (Design AB2.1.3.3a in
(-)METG1 HC)
EVQLVESGGGLVQPGGSLRLSCAASGYTFTSYWLHWVRKAPGKGLEWVG

MIDPSNSDTRFNPEFKDRFTISADTSKNTAYLQMNSLRAEDTAVYYCAT

YRSYVTPLDYWGQGTLVTVSSASTKGPSVFPLAPSSKSTSGGTAALGCL

VKDYFPEPVTVSWNSGALTSGVATGPAVLQSSGLYSLSSVVTVPSSSLG

TQTYICNVNHKPSNTKVDKKVEPKSCDKTHTCPPCPAPELLGGPSVFLF

PPKPKDTLMISRTPEVTCVVVDVSHEDPEVKFNWYVDGVEVHNAKTKPR

EEQYQSTYRVVSVLTVLHQDWLNGKEYKCKVSNKALPAPIEKTISKAKG

QPREPQVYTLPPSRDELTKNQVSLTCLVKGFYPSDIAVEWESNGQPENN

YDTTPPVLDSDGSFFLYSDLTVDKSRWQQGNVFSCSVMHEALHNHYTQK

SLSLSPG

SEQ ID NO. 61:
AB2133aMETλ (METMAB LC with AB in V_L and
2.1.3.3a C_λ)
RIQMTQSPSSLSASVGDRVTITCKSSQSLLYTSSQKNYLAWYQDKPGKA

PKLLIYWASTRESGVPSRFSGSGSGTDFTLTISSLQPEDFATYYCQQYY

AYPWTFGQGTKVEIKGQPKAAPSVTLFPPSSEELQANKATLVCYISDFY

PGAVTVAWKADSSPVKAGVETTTPSKQSNNKYAAWSYLSLTPEQWKSHR

SYSCQVTHEGSTVEKTVAPTEC

SEQ ID NO. 62:
AB2133aMETκ (METMAB LC with AB in V_L and
2.1.3.3a Cκ)
RIQMTQSPSSLSASVGDRVTITCKSSQSLLYTSSQKNYLAWYQDKPGKA

PKLLIYWASTRESGVPSRFSGSGSGTDFTLTISSLQPEDFATYYCQQYY

AYPWTFGQGTKVEIKRTVAAPSVFIFPPSDEQLKSGTASVVCYLNNFYP

REAKVQWKVDNALQSGNSQESVTEQDSKDSTYSLWSTLTLSKADYEKHK

VYACEVTHQGLSSPVTKSFNRGEC

SEQ ID NO. 63:
Wild-Type Cκ
RTVAAPSVFIFPPSDEQLKSGTASVVCLLNNFYPREAKVQWKVDNALQS

GNSQESVTEQDSKDSTYSLSSTLTLSKADYEKHKVYACEVTHQGLSSPV

TKSFNRGEC

SEQ ID NO. 64:
2133a Cκ
RTVAAPSVFIFPPSDEQLKSGTASVVCYLNNFYPREAKVQWKVDNALQS
```

```
SEQ ID NO. 65:
HC minus V_H DESIGN 2133a + A172R
ASTKGPSVFPLAPSSKSTSGGTAALGCLVKDYFPEPVTVSWNSGALTSG
VRTGPAVLQSSGLYSLSSVVTVPSSSLGTQTYICNVNHKPSNTKVDKKV
EPKSCDKTHTCPPCPAPELLGGPSVFLFPPKPKDTLMISRTPEVTCVVV
DVSHEDPEVKFNWYVDGVEVHNAKTKPREEQYNSTYRVVSVLTVLHQDW
LNGKEYKCKVSNKALPAPIEKTISKAKGQPREPQVYTLPPSRDELTKNQ
VSLTCLVKGFYPSDIAVEWESNGQPENNYKTTPPVLDSDGSFFLYSKLT
VDKSRWQQGNVFSCSVMHEALHNHYTQKSLSLSPG SEQ ID NO. 66:
HC minus V_H DESIGN 2133a + V190M
ASTKGPSVFPLAPSSKSTSGGTAALGCLVKDYFPEPVTVSWNSGALTSG
VATGPAVLQSSGLYSLSSM**TVPSSSLGTQTYICNVNHKPSNTKVDKKV
EPKSCDKTHTCPPCPAPELLGGPSVFLFPPKPKDTLMISRTPEVTCVVV
DVSHEDPEVKFNWYVDGVEVHNAKTKPREEQYNSTYRVVSVLTVLHQDW
LNGKEYKCKVSNKALPAPIEKTISKAKGQPREPQVYTLPPSRDELTKNQ
VSLTCLVKGFYPSDIAVEWESNGQPENNYKTTPPVLDSDGSFFLYSKLT
VDKSRWQQGNVFSCSVMHEALHNHYTQKSLSLSPG SEQ ID NO. 67:
HC minus V_H DESIGN 2133a + V190I
ASTKGPSVFPLAPSSKSTSGGTAALGCLVKDYFPEPVTVSWNSGALTSG
VATGPAVLQSSGLYSLSSI**TVPSSSLGTQTYICNVNHKPSNTKVDKKV
EPKSCDKTHTCPPCPAPELLGGPSVFLFPPKPKDTLMISRTPEVTCVVV
DVSHEDPEVKFNWYVDGVEVHNAKTKPREEQYNSTYRVVSVLTVLHQDW
LNGKEYKCKVSNKALPAPIEKTISKAKGQPREPQVYTLPPSRDELTKNQ
VSLTCLVKGFYPSDIAVEWESNGQPENNYKTTPPVLDSDGSFFLYSKLT
VDKSRWQQGNVFSCSVMHEALHNHYTQKSLSLSPG SEQ ID NO. 68:
HC minus V_H DESIGN 2133a + A172R + V190M
ASTKGPSVFPLAPSSKSTSGGTAALGCLVKDYFPEPVTVSWNSGALTSG
VRTGPAVLQSSGLYSLSSMTVPSSSLGTQTYICNVNHKPSNTKVDKKV
EPKSCDKTHTCPPCPAPELLGGPSVFLFPPKPKDTLMISRTPEVTCVVV
DVSHEDPEVKFNWYVDGVEVHNAKTKPREEQYNSTYRVVSVLTVLHQDW
LNGKEYKCKVSNKALPAPIEKTISKAKGQPREPQVYTLPPSRDELTKNQ
VSLTCLVKGFYPSDIAVEWESNGQPENNYKTTPPVLDSDGSFFLYSKLT
VDKSRWQQGNVFSCSVMHEALHNHYTQKSLSLSPG SEQ ID NO. 69:
HC minus V_H DESIGN 2133a + A172R + V190I
ASTKGPSVFPLAPSSKSTSGGTAALGCLVKDYFPEPVTVSWNSGALTSG
VRTGPAVLQSSGLYSLSSITVPSSSLGTQTYICNVNHKPSNTKVDKKV
EPKSCDKTHTCPPCPAPELLGGPSVFLFPPKPKDTLMISRTPEVTCVVV
DVSHEDPEVKFNWYVDGVEVHNAKTKPREEQYNSTYRVVSVLTVLHQDW
LNGKEYKCKVSNKALPAPIEKTISKAKGQPREPQVYTLPPSRDELTKNQ
VSLTCLVKGFYPSDIAVEWESNGQPENNYKTTPPVLDSDGSFFLYSKLT
VDKSRWQQGNVFSCSVMHEALHNHYTQKSLSLSPG SEQ ID NO. 70:
Cκ_2133a_V133L
RTVAAPSVFIFPPSDEQLKSGTASVLCYLNNFYPREAKVQWKVDNALQS
GNSQESVTEQDSKDSTYSLWSTLTLSKADYEKHKVYACEVTHQGLSSPV
TKSFNRGEC SEQ ID NO. 71:
Cκ_2133a_S174Q
RTVAAPSVFIFPPSDEQLKSGTASVVCYLNNFYPREAKVQWKVDNALQS
GNSQESVTEQDSKDSTYQLWSTLTLSKADYEKHKVYACEVTHQGLSSPV
TKSFNRGEC SEQ ID NO. 72:
Cκ_2133a_S174D
RTVAAPSVFIFPPSDEQLKSGTASVVCYLNNFYPREAKVQWKVDNALQS
GNSQESVTEQDSKDSTYDLWSTLTLSKADYEKHKVYACEVTHQGLSSPV
TKSFNRGEC SEQ ID NO. 73:
Cκ_2133a_V133L_S174Q
RTVAAPSVFIFPPSDEQLKSGTASVLCYLNNFYPREAKVQWKVDNALQS
GNSQESVTEQDSKDSTYQLWSTLTLSKADYEKHKVYACEVTHQGLSSPV
TKSFNRGEC SEQ ID NO. 74:
Cκ_2133a_V133L_S174D
RTVAAPSVFIFPPSDEQLKSGTASVLCYLNNFYPREAKVQWKVDNALQS
GNSQESVTEQDSKDSTYDLWSTLTLSKADYEKHKVYACEVTHQGLSSPV
TKSFNRGEC SEQ ID NO. 75:
(-)PG1_AB2133a_MR (Pertuzumab)
EVQLVESGGGLVQPGGSLRLSCAASGFTFTDYTMDWVRKAPGKGLEWVA
DVNPNSGGSIYNQEFKGRFTLSVDRSKNTLYLQMNSLRAEDTAVYYCAR
NLGPSFYFDYWGQGTLVTVSSASTKGPSVFPLAPSSKSTSGGTAALGCL
VKDYFPEPVTVSWNSGALTSGVRTGPAVLQSSGLYSLSSMTVPSSSLG
TQTYICNVNHKPSNTKVDKKVEPKSCDKTHTCPPCPAPELLGGPSVFLF
PPKPKDTLMISRTPEVTCVVVDVSHEDPEVKFNWYVDGVEVHNAKTKPR
EEQYQSTYRVVSVLTVLHQDWLNGKEYKCKVSNKALPAPIEKTISKAKG
QPREPQVYTLPPSRDELTKNQVSLTCLVKGFYPSDIAVEWESNGQPENN
YDTTPPVLDSDGSFFLYSDLTVDKSRWQQGNVFSCSVMHEALHNHYTQK
SLSLSPG SEQ ID NO. 76:
(-)PG1_AB2133a_IR (Pertuzumab)
EVQLVESGGGLVQPGGSLRLSCAASGFTFTDYTMDWVRKAPGKGLEWVA
DVNPNSGGSIYNQEFKGRFTLSVDRSKNTLYLQMNSLRAEDTAVYYCAR
NLGPSFYFDYWGQGTLVTVSSASTKGPSVFPLAPSSKSTSGGTAALGCL
VKDYFPEPVTVSWNSGALTSGVRTGPAVLQSSGLYSLSSITVPSSSLG
TQTYICNVNHKPSNTKVDKKVEPKSCDKTHTCPPCPAPELLGGPSVFLF
PPKPKDTLMISRTPEVTCVVVDVSHEDPEVKFNWYVDGVEVHNAKTKPR
EEQYQSTYRVVSVLTVLHQDWLNGKEYKCKVSNKALPAPIEKTISKAKG
```

```
QPREPQVYTLPPSRDELTKNQVSLTCLVKGFYPSDIAVEWESNGQPENN

YDTTPPVLDSDGSFFLYSDLTVDKSRWQQGNVFSCSVMHEALHNHYTQK

SLSLSPG

SEQ ID NO. 77:
(-)MetG1_AB2133a_MR (MetMAb)
EVQLVESGGGLVQPGGSLRLSCAASGYTFTSYWLHWVRKAPGKGLEWVA

DVNPNSGGSIYNQEFKGRFTLSVDRSKNTLYLQMNSLRAEDTAVYYCAR

NLGPSFYFDYWGQGTLVTVSSASTKGPSVFPLAPSSKSTSGGTAALGCL

VKDYFPEPVTVSWNSGALTSGVRTGPAVLQSSGLYSLSSMVTVPSSSLG

TQTYICNVNHKPSNTKVDKKVEPKSCDKTHTCPPCPAPELLGGPSVFLF

PPKPKDTLMISRTPEVTCVVVDVSHEDPEVKFNWYVDGVEVHNAKTKPR

EEQYQSTYRVVSVLTVLHQDWLNGKEYKCKVSNKALPAPIEKTISKAKG

QPREPQVYTLPPSRDELTKNQVSLTCLVKGFYPSDIAVEWESNGQPENN

YDTTPPVLDSDGSFFLYSDLTVDKSRWQQGNVFSCSVMHEALHNHYTQK

SLSLSPG

SEQ ID NO. 78:
(-)MetG1_AB2133a_IR (MetMAb)
EVQLVESGGGLVQPGGSLRLSCAASGYTFTSYWLHWVRKAPGKGLEWVA

DVNPNSGGSIYNQEFKGRFTLSVDRSKNTLYLQMNSLRAEDTAVYYCAR

NLGPSFYFDYWGQGTLVTVSSASTKGPSVFPLAPSSKSTSGGTAALGCL

VKDYFPEPVTVSWNSGALTSGVRTGPAVLQSSGLYSLSSIVTVPSSSLG

TQTYICNVNHKPSNTKVDKKVEPKSCDKTHTCPPCPAPELLGGPSVFLF

PPKPKDTLMISRTPEVTCVVVDVSHEDPEVKFNWYVDGVEVHNAKTKPR

EEQYQSTYRVVSVLTVLHQDWLNGKEYKCKVSNKALPAPIEKTISKAKG

QPREPQVYTLPPSRDELTKNQVSLTCLVKGFYPSDIAVEWESNGQPENN

YDTTPPVLDSDGSFFLYSDLTVDKSRWQQGNVFSCSVMHEALHNHYTQK

SLSLSPG

SEQ ID NO. 79:
Pκ_AB2133a_LD (Pertuzumab)
RIQMTQSPSSLSASVGDRVTITCKASQDVSIGVAWYQDKPGKAPKLLIY

SASYRYTGVPSRFSGSGSGTDFTLTISSLQPEDFATYYCQQYYIYPYTF

GQGTKVEIKRTVAAPSVFIFPPSDEQLKSGTASVLCYLNNFYPREAKVQ

WKVDNALQSGNSQESVTEQDSKDSTYDLWSTLTLSKADYEKHKVYACEV

THQGLSSPVTKSFNRGEC

SEQ ID NO. 80:
Pκ_AB2133a_LQ (Pertuzumab)
RIQMTQSPSSLSASVGDRVTITCKASQDVSIGVAWYQDKPGKAPKLLIY

SASYRYTGVPSRFSGSGSGTDFTLTISSLQPEDFATYYCQQYYIYPYTF

GQGTKVEIKRTVAAPSVFIFPPSDEQLKSGTASVLCYLNNFYPREAKVQ

WKVDNALQSGNSQESVTEQDSKDSTYQLWSTLTLSKADYEKHKVYACEV

THQGLSSPVTKSFNRGEC

SEQ ID NO. 81:
Metκ_AB2133a_LD (MetMAb)
RIQMTQSPSSLSASVGDRVTITCKSSQSLLYTSSQKNYLAWYQDKPGKA

PKLLIYWASTRESGVPSRFSGSGSGTDFTLTISSLQPEDFATYYCQQYY

AYPWTFGQGTKVEIKRTVAAPSVFIFPPSDEQLKSGTASVLCYLNNFYP

REAKVQWKVDNALQSGNSQESVTEQDSKDSTYDLWSTLTLSKADYEKHK

VYACEVTHQGLSSPVTKSFNRGEC

SEQ ID NO. 82:
Metκ_AB2133a_LQ (MetMAb)
RIQMTQSPSSLSASVGDRVTITCKSSQSLLYTSSQKNYLAWYQDKPGKA

PKLLIYWASTRESGVPSRFSGSGSGTDFTLTISSLQPEDFATYYCQQYY

AYPWTFGQGTKVEIKRTVAAPSVFIFPPSDEQLKSGTASVLCYLNNFYP

REAKVQWKVDNALQSGNSQESVTEQDSKDSTYQLWSTLTLSKADYEKHK

VYACEVTHQGLSSPVTKSFNRGEC

SEQ ID NO 83:
(+)TG1_H4 (Trastuzumab)
EVQLVESGGGLVQPGGSLRLSCAASGFNIKDTYIHWVRYAPGKGLEWVA

RIYPTNGYTRYADSVKGRFTISADTSKNTAYLQMNSLRAEDTAVYYCSR

WGGDGFYAMDYWGQGTLVTVSSASTKGPSVFPLAPSSKSTSGGTAALGC

LVKDYFPEPVTVSWNSGALTSGVHTFPAVLQSSGLYSLSSVVTVPSSSL

GTQTYICNVNHKPSNTKVDKKVEPKSCDKTHTCPPCPAPELLGGPSVFL

FPPKPKDTLMISRTPEVTCVVVDVSHEDPEVKFNWYVDGVEVHNAKTKP

REEQYQSTYRVVSVLTVLHQDWLNGKEYKCKVSNKALPAPIEKTISKAK

GQPREPQVYTLPPSRKELTKNQVSLTCLVKGFYPSDIAVEWESNGQPEN

NYKTTPPVLKSDGSFFLYSKLTVDKSRWQQGNVFSCSVMHEALHNHYTQ

KSLSLSPG

SEQ ID NO 84:
(+)TG1_H4 (Trastuzumab) + CS
EVQLVESGGGLVQPGGSLRLSCAASGFNIKDTYIHWVRYAPGKGLEWVA

RIYPTNGYTRYADSVKGRFTISADTSKNTAYLQMNSLRAEDTAVYYCSR

WGGDGFYAMDYWGQGTLVTVSSASTKGPSVFPLAPCSKSTSGGTAALGC

LVKDYFPEPVTVSWNSGALTSGVHTFPAVLQSSGLYSLSSVVTVPSSSL

GTQTYICNVNHKPSNTKVDKKVEPDSGDKTHTCPPCPAPELLGGPSVFL

FPPKPKDTLMISRTPEVTCVVVDVSHEDPEVKFNWYVDGVEVHNAKTKP

REEQYQSTYRVVSVLTVLHQDWLNGKEYKCKVSNKALPAPIEKTISKAK

GQPREPQVYTLPPSRKELTKNQVSLTCLVKGFYPSDIAVEWESNGQPEN

NYKTTPPVLKSDGSFFLYSKLTVDKSRWQQGNVFSCSVMHEALHNHYTQ

KSLSLSPG

SEQ ID NO 85:
(+)TG1_H4 (Trastuzumab) + DR
EVQLVESGGGLVQPGGSLRLSCAASGFNIKDTYIHWVRYAPGKGLEWVA

RIYPTNGYTRYADSVKGRFTISADTSKNTAYLQMNSLRAEDTAVYYCSR

WGGDGFYAMDYWGRGTLVTVSSASTKGPSVFPLAPSSKSTSGGTAALGC

LVKDYFPEPVTVSWNSGALTSGVHTFPAVLQSSGLYSLSSVVTVPSSSL

GTQTYICNVNHKPSNTKVDKKVEPKSCDKTHTCPPCPAPELLGGPSVFL

FPPKPKDTLMISRTPEVTCVVVDVSHEDPEVKFNWYVDGVEVHNAKTKP

REEQYQSTYRVVSVLTVLHQDWLNGKEYKCKVSNKALPAPIEKTISKAK

GQPREPQVYTLPPSRKELTKNQVSLTCLVKGFYPSDIAVEWESNGQPEN
```

-continued
NYKTTPPVLKSDGSFFLYSKLTVDKSRWQQGNVFSCSVMHEALHNHYTQ
KSLSLSPG

SEQ ID NO 86:
(+)TG1_H4 (Trastuzumab) + CS + DR
EVQLVESGGGLVQPGGSLRLSCAASGFNIKDTYIHWVRYAPGKGLEWVA
RIYPTNGYTRYADSVKGRFTISADTSKNTAYLQMNSLRAEDTAVYYCSR
WGGDGFYAMDYWGRGTLVTVSSASTKGPSVFPLAPCSKSTSGGTAALGC
LVKDYFPEPVTVSWNSGALTSGVHTFPAVLQSSGLYSLSSVVTVPSSSL
GTQTYICNVNHKPSNTKVDKKVEPDSGDKTHTCPPCPAPELLGGPSVFL
FPPKPKDTLMISRTPEVTCVVVDVSHEDPEVKFNWYVDGVEVHNAKTKP
REEQYQSTYRVVSVLTVLHQDWLNGKEYKCKVSNKALPAPIEKTISKAK
GQPREPQVYTLPPSRKELTKNQVSLTCLVKGFYPSDIAVEWESNGQPEN
NYKTTPPVLKSDGSFFLYSKLTVDKSRWQQGNVFSCSVMHEALHNHYTQ
KSLSLSPG SEQ ID NO 87:
Tκ_H4 (Trastuzumab)
DIQMTQSPSSLSASVGDRVTITCRASQDVNTAVAWYQRKPGKAPKLLIY
SASFLYSGVPSRFSGSRSGTDFTLTISSLQPEDFATYYCQQHYTTPPTF
GQGTKVEIKRTVAAPSVFIFPPSDEQLKSGTASVVCLLNNFYPREAKVQ
WKVDNALQSGNSQESVTEQDSKDSTYSLSSTLTLSKADYEKHKVYACEV
THQGLSSPVTKSFNRGEC SEQ ID NO 88:
Tκ_H4 (Trastuzumab) + CS
DIQMTQSPSSLSASVGDRVTITCRASQDVNTAVAWYQRKPGKAPKLLIY
SASFLYSGVPSRFSGSRSGTDFTLTISSLQPEDFATYYCQQHYTTPPTF
GQGTKVEIKRTVAAPSVFIFPPSKEQLKSGTASVVCLLNNFYPREAKVQ
WKVDNALQSGNSQESVTEQDSKDSTYSLSSTLTLSKADYEKHKVYACEV
THQGLSSPVTKSFNRGEC SEQ ID NO 89:
Tκ_H4 (Trastuzumab) + DR
DIQMTQSPSSLSASVGDRVTITCRASQDVNTAVAWYQRKPGDAPKLLIY
SASFLYSGVPSRFSGSRSGTDFTLTISSLQPEDFATYYCQQHYTTPPTF
GQGTKVEIKRTVAAPSVFIFPPSDEQLKSGTASVVCLLNNFYPREAKVQ
WKVDNALQSGNSQESVTEQDSKDSTYSLSSTLTLSKADYEKHKVYACEV
THQGLSSPVTKSFNRGEC SEQ ID NO 90:
Tκ_H4 (Trastuzumab) + CS + DR
DIQMTQSPSSLSASVGDRVTITCRASQDVNTAVAWYQRKPGDAPKLLIY
SASFLYSGVPSRFSGSRSGTDFTLTISSLQPEDFATYYCQQHYTTPPTF
GQGTKVEIKRTVAAPSVFIFPPSKEQLKSGTASVVCLLNNFYPREAKVQ
WKVDNALQSGNSQESVTEQDSKDSTYSLSSTLTLSKADYEKHKVYACEV
THQGLSSPVTKSFNRGEC SEQ ID NO 91:
(+)PG1 H4WT (Pertuzumab)
EVQLVESGGGLVQPGGSLRLSCAASGFTFTDYTMDWVRYAPGKGLEWVA
DVNPNSGGSIYNQRFKGRFTLSVDRSKNTLYLQMNSLRAEDTAVYYCAR
NLGPSFYFDYWGQGTLVTVSSASTKGPSVFPLAPSSKSTSGGTAALGCL
VKDYFPEPVTVSWNSGALTSGVHTFPAVLQSSGLYSLSSVVTVPSSSLG
TQTYICNVNHKPSNTKVDKKVEPKSCDKTHTCPPCPAPELLGGPSVFLF
PPKPKDTLMISRTPEVTCVVVDVSHEDPEVKFNWYVDGVEVHNAKTKPR
EEQYQSTYRVVSVLTVLHQDWLNGKEYKCKVSNKALPAPIEKTISKAKG
QPREPQVYTLPPSRKELTKNQVSLTCLVKGFYPSDIAVEWESNGQPENN
YKTTPPVLKSDGSFFLYSKLTVDKSRWQQGNVFSCSVMHEALHNHYTQK
SLSLSPG SEQID NO 92:
(+)PG1 H4WT + CS (Pertuzumab)
EVQLVESGGGLVQPGGSLRLSCAASGFTFTDYTMDWVRYAPGKGLEWVA
DVNPNSGGSIYNQRFKGRFTLSVDRSKNTLYLQMNSLRAEDTAVYYCAR
NLGPSFYFDYWGQGTLVTVSSASTKGPSVFPLAPCSKSTSGGTAALGCL
VKDYFPEPVTVSWNSGALTSGVHTFPAVLQSSGLYSLSSVVTVPSSSLG
TQTYICNVNHKPSNTKVDKKVEPDSGDKTHTCPPCPAPELLGGPSVFLF
PPKPKDTLMISRTPEVTCVVVDVSHEDPEVKFNWYVDGVEVHNAKTKPR
EEQYQSTYRVVSVLTVLHQDWLNGKEYKCKVSNKALPAPIEKTISKAKG
QPREPQVYTLPPSRKELTKNQVSLTCLVKGFYPSDIAVEWESNGQPENN
YKTTPPVLKSDGSFFLYSKLTVDKSRWQQGNVFSCSVMHEALHNHYTQK
SLSLSPG SEQ ID NO 93:
(+)PG1 H4WT + DR (Pertuzumab)
EVQLVESGGGLVQPGGSLRLSCAASGFTFTDYTMDWVRYAPGKGLEWVA
DVNPNSGGSIYNQRFKGRFTLSVDRSKNTLYLQMNSLRAEDTAVYYCAR
NLGPSFYFDYWGRGTLVTVSSASTKGPSVFPLAPSSKSTSGGTAALGCL
VKDYFPEPVTVSWNSGALTSGVHTFPAVLQSSGLYSLSSVVTVPSSSLG
TQTYICNVNHKPSNTKVDKKVEPKSCDKTHTCPPCPAPELLGGPSVFLF
PPKPKDTLMISRTPEVTCVVVDVSHEDPEVKFNWYVDGVEVHNAKTKPR
EEQYQSTYRVVSVLTVLHQDWLNGKEYKCKVSNKALPAPIEKTISKAKG
QPREPQVYTLPPSRKELTKNQVSLTCLVKGFYPSDIAVEWESNGQPENN
YKTTPPVLKSDGSFFLYSKLTVDKSRWQQGNVFSCSVMHEALHNHYTQK
SLSLSPG SEQ ID NO 94:
(+)PG1 H4WT + CS + DR (Pertuzumab)
EVQLVESGGGLVQPGGSLRLSCAASGFTFTDYTMDWVRYAPGKGLEWVA
DVNPNSGGSIYNQRFKGRFTLSVDRSKNTLYLQMNSLRAEDTAVYYCAR
NLGPSFYFDYWGRGTLVTVSSASTKGPSVFPLAPCSKSTSGGTAALGCL
VKDYFPEPVTVSWNSGALTSGVHTFPAVLQSSGLYSLSSVVTVPSSSLG
TQTYICNVNHKPSNTKVDKKVEPDSGDKTHTCPPCPAPELLGGPSVFLF
PPKPKDTLMISRTPEVTCVVVDVSHEDPEVKFNWYVDGVEVHNAKTKPR
EEQYQSTYRVVSVLTVLHQDWLNGKEYKCKVSNKALPAPIEKTISKAKG
QPREPQVYTLPPSRKELTKNQVSLTCLVKGFYPSDIAVEWESNGQPENN
YKTTPPVLKSDGSFFLYSKLTVDKSRWQQGNVFSCSVMHEALHNHYTQK
SLSLSPG -continued SEQ ID NO. 95:
Pκ H4WT + CS (Pertuzumab)
DIQMTQSPSSLSASVGDRVTITCKASQDVSIGVAWYQRKPGKAPKLLIY
SASYRYTGVPSRFSGSGSGTDFTLTISSLQPEDFATYYCQQYYIYPYTF
GQGTKVEIKRTVAAPSVFIFPPSKEQLKSGTASVVCLLNNFYPREAKVQ
WKVDNALQSGNSQESVTEQDSKDSTYSLSSTLTLSKADYEKHKVYACEV
THQGLSSPVTKSFNRGEC SEQ ID NO. 96:
Pκ H4WT + DR (Pertuzumab)
DIQMTQSPSSLSASVGDRVTITCKASQDVSIGVAWYQRKPGDAPKLLIY
SASYRYTGVPSRFSGSGSGTDFTLTISSLQPEDFATYYCQQYYIYPYTF
GQGTKVEIKRTVAAPSVFIFPPSDEQLKSGTASVVCLLNNFYPREAKVQ
WKVDNALQSGNSQESVTEQDSKDSTYSLSSTLTLSKADYEKHKVYACEV
THQGLSSPVTKSFNRGEC SEQ ID NO. 97:
Pκ H4WT + CS + DR (Pertuzumab)
DIQMTQSPSSLSASVGDRVTITCKASQDVSIGVAWYQRKPGDAPKLLIY
SASYRYTGVPSRFSGSGSGTDFTLTISSLQPEDFATYYCQQYYIYPYTF
GQGTKVEIKRTVAAPSVFIFPPSKEQLKSGTASVVCLLNNFYPREAKVQ
WKVDNALQSGNSQESVTEQDSKDSTYSLSSTLTLSKADYEKHKVYACEV
THQGLSSPVTKSFNRGEC SEQ ID NO. 98:
(+)MG1 H4WT + CS
QVQLVQSGAEVKKPGASVKVSCKASGYTFTSHWMHWVRYAPGQGLEWIG
EFNPSNGRTNYNEKFKSKATMTVDTSTNTAYMELSSLRSEDTAVYYCAS
RDYDYDGRYFDYWGQGTLVTVSSASTKGPSVFPLAPCSKSTSGGTAALG
CLVKDYFPEPVTVSWNSGALTSGVHTFPAVLQSSGLYSLSSVVTVPSSS
LGTQTYICNVNHKPSNTKVDKKVEPDSGDKTHTCPPCPAPELLGGPSVF
LFPPKPKDTLMISRTPEVTCVVVDVSHEDPEVKFNWYVDGVEVHNAKTK
PREEQYQSTYRVVSVLTVLHQDWLNGKEYKCKVSNKALPAPIEKTISKA
KGQPREPQVYTLPPSRKELTKNQVSLTCLVKGFYPSDIAVEWESNGQPE
NNYKTTPPVLKSDGSFFLYSKLTVDKSRWQQGNVFSCSVMHEALHNHYT
QKSLSLSPG SEQ ID NO. 99:
(+)MG1 H4WT + DR
QVQLVQSGAEVKKPGASVKVSCKASGYTFTSHWMHWVRYAPGQGLEWIG
EFNPSNGRTNYNEKFKSKATMTVDTSTNTAYMELSSLRSEDTAVYYCAS
RDYDYDGRYFDYWGRGTLVTVSSASTKGPSVFPLAPCSKSTSGGTAALG
CLVKDYFPEPVTVSWNSGALTSGVHTFPAVLQSSGLYSLSSVVTVPSSS
LGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTK
PREEQYQSTYRVVSVLTVLHQDWLNGKEYKCKVSNKALPAPIEKTISKA
KGQPREPQVYTLPPSRKELTKNQVSLTCLVKGFYPSDIAVEWESNGQPE
NNYKTTPPVLKSDGSFFLYSKLTVDKSRWQQGNVFSCSVMHEALHNHYT
QKSLSLSPG SEQ ID NO. 100:
(+)MG1 H4WT + CS + DR
QVQLVQSGAEVKKPGASVKVSCKASGYTFTSHWMHWVRYAPGQGLEWIG
EFNPSNGRTNYNEKFKSKATMTVDTSTNTAYMELSSLRSEDTAVYYCAS
RDYDYDGRYFDYWGRGTLVTVSSASTKGPSVFPLAPCSKSTSGGTAALG
CLVKDYFPEPVTVSWNSGALTSGVHTFPAVLQSSGLYSLSSVVTVPSSS
LGTQTYICNVNHKPSNTKVDKKVEPDSGDKTHTCPPCPAPELLGGPSVF
LFPPKPKDTLMISRTPEVTCVVVDVSHEDPEVKFNWYVDGVEVHNAKTK
PREEQYQSTYRVVSVLTVLHQDWLNGKEYKCKVSNKALPAPIEKTISKA
KGQPREPQVYTLPPSRKELTKNQVSLTCLVKGFYPSDIAVEWESNGQPE
NNYKTTPPVLKSDGSFFLYSKLTVDKSRWQQGNVFSCSVMHEALHNHYT
QKSLSLSPG SEQ ID NO. 101:
Mκ H4WT + CS
DIQMTQSPSSLSASVGDRVTITCSASSSVTYMYWYQRKPGKAPKLLIYD
TSNLASGVPSRFSGSGSGTDYTFTISSLQPEDIATYYCQQWSSHIFTFG
QGTKVEIKRTVAAPSVFIFPPSKEQLKSGTASVVCLLNNFYPREAKVQW
KVDNALQSGNSQESVTEQDSKDSTYSLSSTLTLSKADYEKHKVYACEVT
HQGLSSPVTKSFNRGEC SEQ ID NO. 102:
Mκ H4WT + DR
DIQMTQSPSSLSASVGDRVTITCSASSSVTYMYWYQRKPGDAPKLLIYD
TSNLASGVPSRFSGSGSGTDYTFTISSLQPEDIATYYCQQWSSHIFTFG
QGTKVEIKRTVAAPSVFIFPPSDEQLKSGTASVVCLLNNFYPREAKVQW
KVDNALQSGNSQESVTEQDSKDSTYSLSSTLTLSKADYEKHKVYACEVT
HQGLSSPVTKSFNRGEC SEQ ID NO. 103:
Mκ H4WT + CS + DR
DIQMTQSPSSLSASVGDRVTITCSASSSVTYMYWYQRKPGDAPKLLIYD
TSNLASGVPSRFSGSGSGTDYTFTISSLQPEDIATYYCQQWSSHIFTFG
QGTKVEIKRTVAAPSVFIFPPSKEQLKSGTASVVCLLNNFYPREAKVQW
KVDNALQSGNSQESVTEQDSKDSTYSLSSTLTLSKADYEKHKVYACEVT
HQGLSSPVTKSFNRGEC SEQ ID NO. 104:
(+)BHA10G1 H4WT
QVQLVQSGAEVKKPGSSVKVSCKASGYTFTTYYLHWVRYAPGQGLEWMG
WIYPGNVHAQYNEKFKGRVTITADKSTSTAYMELSSLRSEDTAVYYCAR
SWEGFPYWGQGTTVTVSSASTKGPSVFPLAPSSKSTSGGTAALGCLVKD
YFPEPVTVSWNSGALTSGVHTFPAVLQSSGLYSISSVVTVPSSSLGTQT
YICNVNHKPSNTKVDKKVEPKSCDKTHTCPPCPAPELLGGPSVFLFPPK
PKDTLMISRTPEVTCVVVDVSHEDPEVKFNWYVDGVEVHNAKTKPREEQ
YQSTYRVVSVLTVLHQDWLNGKEYKCKVSNKALPAPIEKTISKAKGQPR
EPQVYTLPPSRKELTKNQVSLTCLVKGFYPSDIAVEWESNGQPENNYKT
TPPVLKSDGSFFLYSKLTVDKSRWQQGNVFSCSVMHEALHNHYTQKSLS
LSPG SEQ ID NO. 105:
(+)BHA10G1 H4WT + CS
QVQLVQSGAEVKKPGSSVKVSCKASGYTFTTYYLHWVRYAPGQGLEWMG

WIYPGNVHAQYNEKFKGRVTITADKSTSTAYMELSSLRSEDTAVYYCAR

SWEGFPYWGQGTTVTVSSASTKGPSVFPLAPCSKSTSGGTAALGCLVKD

YFPEPVTVSWNSGALTSGVHTFPAVLQSSGLYSISSVVTVPSSSLGTQT

YICNVNHKPSNTKVDKKVEPDSGDKTHTCPPCPAPELLGGPSVFLFPPK

PKDTLMISRTPEVTCVVVDVSHEDPEVKFNWYVDGVEVHNAKTKPREEQ

YQSTYRVVSVLTVLHQDWLNGKEYKCKVSNKALPAPIEKTISKAKGQPR

EPQVYTLPPSRKELTKNQVSLTCLVKGFYPSDIAVEWESNGQPENNYKT

TPPVLKSDGSFFLYSKLTVDKSRWQQGNVFSCSVMHEALHNHYTQKSLS

LSPG

SEQ ID NO. 106:
(+)BHA10G1 H4WT + DR
QVQLVQSGAEVKKPGSSVKVSCKASGYTFTTYYLHWVRYAPGQGLEWMG

WIYPGNVHAQYNEKFKGRVTITADKSTSTAYMELSSLRSEDTAVYYCAR

SWEGFPYWGRGTTVTVSSASTKGPSVFPLAPSSKSTSGGTAALGCLVKD

YFPEPVTVSWNSGALTSGVHTFPAVLQSSGLYSISSVVTVPSSSLGTQT

YICNVNHKPSNTKVDKKVEPKSCDKTHTCPPCPAPELLGGPSVFLFPPK

PKDTLMISRTPEVTCVVVDVSHEDPEVKFNWYVDGVEVHNAKTKPREEQ

YQSTYRVVSVLTVLHQDWLNGKEYKCKVSNKALPAPIEKTISKAKGQPR

EPQVYTLPPSRKELTKNQVSLTCLVKGFYPSDIAVEWESNGQPENNYKT

TPPVLKSDGSFFLYSKLTVDKSRWQQGNVFSCSVMHEALHNHYTQKSLS

LSPG

SEQ ID NO. 107:
(+)BHA10G1 H4WT + CS + DR
QVQLVQSGAEVKKPGSSVKVSCKASGYTFTTYYLHWVRYAPGQGLEWMG

WIYPGNVHAQYNEKFKGRVTITADKSTSTAYMELSSLRSEDTAVYYCAR

SWEGFPYWGRGTTVTVSSASTKGPSVFPLAPCSKSTSGGTAALGCLVKD

YFPEPVTVSWNSGALTSGVHTFPAVLQSSGLYSISSVVTVPSSSLGTQT

YICNVNHKPSNTKVDKKVEPDSGDKTHTCPPCPAPELLGGPSVFLFPPK

PKDTLMISRTPEVTCVVVDVSHEDPEVKFNWYVDGVEVHNAKTKPREEQ

YQSTYRVVSVLTVLHQDWLNGKEYKCKVSNKALPAPIEKTISKAKGQPR

EPQVYTLPPSRKELTKNQVSLTCLVKGFYPSDIAVEWESNGQPENNYKT

TPPVLKSDGSFFLYSKLTVDKSRWQQGNVFSCSVMHEALHNHYTQKSLS

LSPG

SEQ ID NO. 108:
(-)TG1 AB2133a (Trastuzumab)
EVQLVESGGGLVQPGGSLRLSCAASGFNIKDTYIHWVRKAPGKGLEWVA

RIYPTNGYTRYADEVKGRFTISADTSKNTAYLQMNSLRAEDTAVYYCSR

WGGDGFYAMDYWGQGTLVTVSSASTKGPSVFPLAPSSKSTSGGTAALGC

LVKDYFPEPVTVSWNSGALTSGVATGPAVLQSSGLYSLSSVVTVPSSSL

GTQTYICNVNHKPSNTKVDKKVEPKSCDKTHTCPPCPAPELLGGPSVFL

FPPKPKDTLMISRTPEVTCVVVDVSHEDPEVKFNWYVDGVEVHNAKTKP

REEQYNSTYRVVSVLTVLHQDWLNGKEYKCKVSNKALPAPIEKTISKAK

GQPREPQVYTLPPSRDELTKNQVSLTCLVKGFYPSDIAVEWESNGQPEN

NYDTTPPVLDSDGSFFLYSDLTVDKSRWQQGNVFSCSVMHEALHNHYTQ

KSLSLSPG

SEQ ID NO. 109:
BHA10k H4WT
DIQMTQSPSSLSASVGDRVTITCKASQNVGINVAWYQRKPGKAPKSLIS

SASYRYSGVPSRFSGSGSGTDFTLTISSLQPEDFATYFCQQYDTYPFTF

GQGTKVEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC

SEQ ID NO. 110:
BHA10k H4WT + CS
DIQMTQSPSSLSASVGDRVTITCKASQNVGINVAWYQRKPGKAPKSLIS

SASYRYSGVPSRFSGSGSGTDFTLTISSLQPEDFATYFCQQYDTYPFTF

GQGTKVEIKRTVAAPSVFIFPPSKEQLKSGTASVVCLLNNFYPREAKVQ

WKVDNALQSGNSQESVTEQDSKDSTYSLSSTLTLSKADYEKHKVYACEV

THQGLSSPVTKSFNRGEC

SEQ ID NO. 111:
BHA10k H4WT + DR
DIQMTQSPSSLSASVGDRVTITCKASQNVGINVAWYQRKPGDAPKSLIS

SASYRYSGVPSRFSGSGSGTDFTLTISSLQPEDFATYFCQQYDTYPFTF

GQGTKVEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC

SEQ ID NO. 112:
BHA10k H4WT + CS + DR
DIQMTQSPSSLSASVGDRVTITCKASQNVGINVAWYQRKPGDAPKSLIS

SASYRYSGVPSRFSGSGSGTDFTLTISSLQPEDFATYFCQQYDTYPFTF

GQGTKVEIKRTVAAPSVFIFPPSKEQLKSGTASVVCLLNNFYPREAKVQ

WKVDNALQSGNSQESVTEQDSKDSTYSLSSTLTLSKADYEKHKVYACEV

THQGLSSPVTKSFNRGEC

SEQ ID NO. 113:
Tĸ AB2133a (Trastuzumab)
RIQMTQSPSSLSASVGDRVTITCRASQDVNTAVAWYQPDKPGKAPKLLI

YSASFLYSGVPSRFSGSRSGTDFTLTISSLQPEDFATYYCQQHYTTPPT

FGQGTKVEIKRTVAAPSVFIFPPSDEQLKSGTASVVCYLNNFYPREAKV

QWKVDNALQSGNSQESVTEQDSKDSTYSLWSTLTLSKADYEKHKVYACE

VTHQGLSSPVTKSFNRGEC

We claim:

1. A method for producing a fragment, antigen binding (Fab), the method comprising (all residues are numbered according to the Kabat numbering system):
   (1) co-expressing in a host cell:
      (a) a first nucleic acid encoding a heavy chain variable (VH) domain and a human IgG heavy chain constant CH1 (CH1) domain, wherein said VH domain comprises a tyrosine at residue 39 and an arginine at residue 105, and said CH1 domain comprises an aspartic acid at residue 228, a cysteine at position 127 and a glycine at position 230; and
      (b) a second nucleic acid encoding both a light chain variable (VL) domain and a light chain constant (CL) domain, wherein said VL domain comprises an arginine at residue 38 and an aspartic acid at residue 42, said CL domain comprises a lysine at residue 122, wherein each of said VH and VL domains comprise three complementarity determining regions (CDRs) which direct binding to an antigen;
   (2) cultivating said host cell under conditions such that said VH and CH1 domains and said VL and CL domains are produced; and
   (3) recovering from said host cell a Fab wherein said Fab comprises said VH and CH1 domains and said VL and CL domains.

2. A method for producing a fragment, antigen binding (Fab), the method comprising (all residues are numbered according to the Kabat numbering system):
   (1) co-expressing in a host cell:
      (a) a first nucleic acid encoding a heavy chain variable (VH) domain and a human IgG heavy chain constant CH1 (CH1) domain, wherein said VH domain comprises a tyrosine at residue 39 and an arginine at residue 105, and said CH1 domain comprises an alanine at residue 172 and a glycine at residue 174; and (b) a second nucleic acid encoding both a light chain variable (VL) domain and a light chain constant (CL) domain, wherein said VL domain comprises an arginine at residue 38 and an aspartic acid at residue 42, said CL domain comprises a tyrosine at residue 135 and a tryptophan at residue 176, wherein each of said VH and VL domains comprise three complementarity determining regions (CDRs) which direct binding to an antigen;

(2) cultivating said host cell under conditions such that said VH and CH1 domains and said VL and CL domains are produced; and (3) recovering from said host cell a Fab wherein said Fab comprises said VH and CH1 domains and said VL and CL domains.

3. A method for producing a fragment, antigen binding (Fab), the method comprising (all residues are numbered according to the Kabat numbering system):

(1) co-expressing in a host cell:

(a) a first nucleic acid encoding a heavy chain variable (VH) domain and a human IgG heavy chain constant CH1 (CH1) domain, wherein said VH domain comprises a lysine at residue 39 and a glutamic acid at residue 62, and said CH1 domain comprises an aspartic acid at residue 228, a cysteine at position 127 and a glycine at position 230; and (b) a second nucleic acid encoding both a light chain variable (VL) domain and a light chain constant (CL) domain, wherein said VL domain comprises an arginine at residue 1 and an aspartic acid at residue 38, said CL domain comprises a lysine at residue 122, wherein each of said VH and VL domains comprise three complementarity determining regions (CDRs) which direct binding to an antigen;

(2) cultivating said host cell under conditions such that said VH and CH1 domains and said VL and CL domains are produced; and (3) recovering from said host cell a Fab wherein said Fab comprises said VH and CH1 domains and said VL and CL domains.

4. The method according to claim 1, wherein said host cell is a mammalian cell.

5. The method according to claim 1, wherein said human IgG CH1 domain is IgG1 or IgG4 isotype.

6. The method according to claim 1, wherein said CL domain is kappa isotype.

7. The method according to claim 2, wherein said host cell is a mammalian cell.

8. The method according to claim 2, wherein said human IgG CH1 domain is IgG1 or IgG4 isotype.

9. The method according to claim 2, wherein said CL domain is kappa isotype.

10. The method according to claim 3, wherein said host cell is a mammalian cell.

11. The method according to claim 3, wherein said human IgG CH1 domain is IgG1 or IgG4 isotype.

12. The method according to claim 3, wherein said CL domain is kappa isotype.

* * * * *

SEQUENCE LISTING

<160> NUMBER OF SEQ ID NOS: 113

<210> SEQ ID NO 1
<211> LENGTH: 448
<212> TYPE: PRT
<213> ORGANISM: Artificial Sequence
<220> FEATURE:
<223> OTHER INFORMATION: Synthetic Construct

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr

```
                355                 360                 365
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
                435                 440                 445

<210> SEQ ID NO 2
<211> LENGTH: 212
<212> TYPE: PRT
<213> ORGANISM: Artificial Sequence
<220> FEATURE:
<223> OTHER INFORMATION: Synthetic Construct

<400> SEQUENCE: 2

Asp Ile Gln Met Thr Gln Ser Pro Ser Ser Leu Ser Ala Ser Val Gly
1               5                   10                  15
Asp Arg Val Thr Ile Thr Cys Lys Ala Ser Gln Asp Val Ser Ile Gly
            20                  25                  30
Val Ala Trp Tyr Gln Gln Lys Pro Gly Lys Ala Pro Lys Leu Leu Ile
        35                  40                  45
Tyr Ser Ala Ser Tyr Arg Tyr Thr Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Tyr Tyr Ile Tyr Pro Tyr
                85                  90                  95
Thr Phe Gly Gln Gly Thr Lys Val Glu Ile Lys Gly Gln Pro Lys Ala
            100                 105                 110
Ala Pro Ser Val Thr Leu Phe Pro Pro Ser Ser Glu Glu Leu Gln Ala
        115                 120                 125
Asn Lys Ala Thr Leu Val Cys Leu Ile Ser Asp Phe Tyr Pro Gly Ala
    130                 135                 140
Val Thr Val Ala Trp Lys Ala Asp Ser Ser Pro Val Lys Ala Gly Val
145                 150                 155                 160
Glu Thr Thr Thr Pro Ser Lys Gln Ser Asn Asn Lys Tyr Ala Ala Ser
                165                 170                 175
Ser Tyr Leu Ser Leu Thr Pro Glu Gln Trp Lys Ser His Arg Ser Tyr
            180                 185                 190
Ser Cys Gln Val Thr His Glu Gly Ser Thr Val Glu Lys Thr Val Ala
        195                 200                 205
Pro Thr Glu Cys
    210

<210> SEQ ID NO 3
<211> LENGTH: 329
<212> TYPE: PRT
<213> ORGANISM: Artificial Sequence
<220> FEATURE:
<223> OTHER INFORMATION: Synthetic Construct

<400> SEQUENCE: 3
```

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 4
<211> LENGTH: 105
<212> TYPE: PRT
<213> ORGANISM: Artificial Sequence
<220> FEATURE:
<223> OTHER INFORMATION: Synthetic Construct

<400> SEQUENCE: 4

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
            35                  40                  45

Val Lys Ala Gly Val Glu Thr Thr Thr Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys
            100                 105

<210> SEQ ID NO 5
<211> LENGTH: 448
<212> TYPE: PRT
<213> ORGANISM: Artificial Sequence
<220> FEATURE:
<223> OTHER INFORMATION: Synthetic Construct

<400> SEQUENCE: 5

Glu Val Gln Leu Val Glu Ser Gly Gly Gly Leu Val Gln Pro Gly Gly
 1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
            35                  40                  45

Ala Asp Val Asn Pro Asn Ser Gly Gly Ser Ile Tyr Asn Gln Arg Phe
 50                  55                  60

Lys Gly Arg Phe Thr Leu Ser Val Asp Arg Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Thr Pro Ala Val Leu
                165                 170                 175

Gln Ser Ser Gly Leu Tyr Ser Leu Ser Ser Phe Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 6
<211> LENGTH: 212
<212> TYPE: PRT
<213> ORGANISM: Artificial Sequence
<220> FEATURE:
<223> OTHER INFORMATION: Synthetic Construct

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys Gly Gln Pro Lys Ala
            100                 105                 110

Ala Pro Ser Val Thr Leu Phe Pro Pro Ser Ser Glu Glu Leu Gln Ala
        115                 120                 125

Asn Lys Ala Thr Leu Val Cys Phe Ile Ser Asp Phe Tyr Pro Gly Ala
    130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Cys
    210

<210> SEQ ID NO 7
<211> LENGTH: 329
<212> TYPE: PRT
<213> ORGANISM: Artificial Sequence
<220> FEATURE:
<223> OTHER INFORMATION: Synthetic Construct

<400> SEQUENCE: 7

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Gly Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 8
<211> LENGTH: 105

```
<212> TYPE: PRT
<213> ORGANISM: Artificial Sequence
<220> FEATURE:
<223> OTHER INFORMATION: Synthetic Construct

<400> SEQUENCE: 8

Gly Gln Pro Lys Ala Ala Pro Ser Val Thr Leu Phe Pro Pro Ser Ser
 1               5                  10                  15

Glu Glu Leu Gln Ala Asn Lys Ala Thr Leu Val Cys Ala Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
50                  55                  60

Lys Tyr Ala Ala Trp Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys
            100                 105

<210> SEQ ID NO 9
<211> LENGTH: 448
<212> TYPE: PRT
<213> ORGANISM: Artificial Sequence
<220> FEATURE:
<223> OTHER INFORMATION: Synthetic Construct

<400> SEQUENCE: 9

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220
```

```
Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 10
<211> LENGTH: 212
<212> TYPE: PRT
<213> ORGANISM: Artificial Sequence
<220> FEATURE:
<223> OTHER INFORMATION: Synthetic Construct

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys Gly Gln Pro Lys Ala
            100                 105                 110

Ala Pro Ser Val Thr Leu Phe Pro Pro Ser Ser Glu Glu Leu Gln Ala
        115                 120                 125

Asn Asp Ala Thr Leu Val Cys Leu Ile Ser Asp Phe Tyr Pro Gly Ala
    130                 135                 140
```

```
Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Cys
    210

<210> SEQ ID NO 11
<211> LENGTH: 329
<212> TYPE: PRT
<213> ORGANISM: Artificial Sequence
<220> FEATURE:
<223> OTHER INFORMATION: Synthetic Construct

<400> SEQUENCE: 11

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Lys Tyr
            20                  25                  30

Phe Pro Glu Pro Val Thr Val Ser Trp Asn Ser Gly Ala Leu Thr Ser
        35                  40                  45

Gly Val His Thr Thr Pro Ala Val Leu Gln Ser Ser Gly Leu Tyr Ser
    50                  55                  60

Leu Ser Ser Phe Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285
```

```
Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 12
<211> LENGTH: 105
<212> TYPE: PRT
<213> ORGANISM: Artificial Sequence
<220> FEATURE:
<223> OTHER INFORMATION: Synthetic Construct

<400> SEQUENCE: 12

Gly Gln Pro Lys Ala Ala Pro Ser Val Thr Leu Phe Pro Pro Ser Ser
1               5                   10                  15

Glu Glu Leu Gln Ala Asn Asp Ala Thr Leu Val Cys Phe Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys
            100                 105

<210> SEQ ID NO 13
<211> LENGTH: 448
<212> TYPE: PRT
<213> ORGANISM: Artificial Sequence
<220> FEATURE:
<223> OTHER INFORMATION: Synthetic Construct

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Lys Ala Pro Gly Lys Gly Leu Glu Trp Val
        35                  40                  45

Ala Asp Val Asn Pro Asn Ser Gly Gly Ser Ile Tyr Asn Gln Glu Phe
50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
```

```
                145                 150                 155                 160
        Asn Ser Gly Ala Leu Thr Ser Gly Val Ala Thr Gly Pro Ala Val Leu
                        165                 170                 175

Gln Ser Ser Gly Leu Tyr Ser Leu Ser Ser Val Val Thr Val Pro Ser
                        180                 185                 190

Ser Ser Leu Gly Thr Gln Thr Tyr Ile Cys Asn Val Asn His Lys Pro
                        195                 200                 205

Ser Asn Thr Lys Val Asp Lys Lys Val Glu Pro Lys Ser Cys Asp Lys
                210                 215                 220

Thr His Thr Cys Pro Pro Cys Pro Ala Pro Glu Leu Leu Gly Gly Pro
        225                 230                 235                 240

Ser Val Phe Leu Phe Pro Pro Lys Pro Lys Asp Thr Leu Met Ile Ser
                        245                 250                 255

Arg Thr Pro Glu Val Thr Cys Val Val Val Asp Val Ser His Glu Asp
                        260                 265                 270

Pro Glu Val Lys Phe Asn Trp Tyr Val Asp Gly Val Glu Val His Asn
                        275                 280                 285

Ala Lys Thr Lys Pro Arg Glu Glu Gln Tyr Gln Ser Thr Tyr Arg Val
                290                 295                 300

Val Ser Val Leu Thr Val Leu His Gln Asp Trp Leu Asn Gly Lys Glu
        305                 310                 315                 320

Tyr Lys Cys Lys Val Ser Asn Lys Ala Leu Pro Ala Pro Ile Glu Lys
                        325                 330                 335

Thr Ile Ser Lys Ala Lys Gly Gln Pro Arg Glu Pro Gln Val Tyr Thr
                        340                 345                 350

Leu Pro Pro Ser Arg Asp Glu Leu Thr Lys Asn Gln Val Ser Leu Thr
                        355                 360                 365

Cys Leu Val Lys Gly Phe Tyr Pro Ser Asp Ile Ala Val Glu Trp Glu
                        370                 375                 380

Ser Asn Gly Gln Pro Glu Asn Asn Tyr Asp Thr Thr Pro Pro Val Leu
        385                 390                 395                 400

Asp Ser Asp Gly Ser Phe Phe Leu Tyr Ser Asp Leu Thr Val Asp Lys
                        405                 410                 415

Ser Arg Trp Gln Gln Gly Asn Val Phe Ser Cys Ser Val Met His Glu
                        420                 425                 430

Ala Leu His Asn His Tyr Thr Gln Lys Ser Leu Ser Leu Ser Pro Gly
                        435                 440                 445

<210> SEQ ID NO 14
<211> LENGTH: 214
<212> TYPE: PRT
<213> ORGANISM: Artificial Sequence
<220> FEATURE:
<223> OTHER INFORMATION: Synthetic Construct

<400> SEQUENCE: 14

Asp Ile Gln Met Thr Gln Ser Pro Ser Ser Leu Ser Ala Ser Val Gly
        1               5                   10                  15

Asp Arg Val Thr Ile Thr Cys Arg Ala Ser Gln Asp Val Ser Thr Ala
                        20                  25                  30

Val Ala Trp Tyr Gln Arg Lys Pro Gly Lys Ala Pro Lys Leu Leu Ile
                        35                  40                  45

Tyr Ser Ala Ser Phe Leu Tyr Ser Gly Val Pro Ser Arg Phe Ser Gly
                        50                  55                  60

Ser Gly Ser Gly Thr Asp Phe Thr Leu Thr Ile Ser Ser Leu Gln Pro
```

```
                65                  70                  75                  80
Glu Asp Phe Ala Thr Tyr Tyr Cys Gln Gln Ser Tyr Thr Thr Pro Pro
                    85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
                130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
                210

<210> SEQ ID NO 15
<211> LENGTH: 105
<212> TYPE: PRT
<213> ORGANISM: Artificial Sequence
<220> FEATURE:
<223> OTHER INFORMATION: Synthetic Construct

<400> SEQUENCE: 15

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Phe Ile Ser Asp
                20                  25                  30

Phe Tyr Pro Gly Ala Val Thr Val Ala Trp Lys Ala Asp Ser Ser Pro
                35                  40                  45

Val Lys Ala Gly Val Glu Thr Thr Thr Pro Ser Lys Gln Ser Asn Asn
50                  55                  60

Lys Tyr Ala Ala Trp Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                    85                  90                  95

Glu Lys Thr Val Ala Pro Thr Glu Cys
                100                 105

<210> SEQ ID NO 16
<211> LENGTH: 212
<212> TYPE: PRT
<213> ORGANISM: Artificial Sequence
<220> FEATURE:
<223> OTHER INFORMATION: Synthetic Construct

<400> SEQUENCE: 16

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
                20                  25                  30

Val Ala Trp Tyr Gln Arg Lys Pro Gly Lys Ala Pro Lys Leu Leu Ile
                35                  40                  45
```

```
Tyr Ser Ala Ser Phe Leu Tyr Ser Gly Val Pro Ser Arg Phe Ser Gly
         50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Ser Tyr Thr Thr Pro Pro
                 85                  90                  95
Thr Phe Gly Gln Gly Thr Lys Val Glu Ile Lys Gly Gln Pro Lys Ala
            100                 105                 110
Ala Pro Ser Val Thr Leu Phe Pro Pro Ser Ser Glu Glu Leu Gln Ala
        115                 120                 125
Asn Lys Ala Thr Leu Val Cys Leu Ile Ser Asp Phe Tyr Pro Gly Ala
130                 135                 140
Val Thr Val Ala Trp Lys Ala Asp Ser Ser Pro Val Lys Ala Gly Val
145                 150                 155                 160
Glu Thr Thr Thr Pro Ser Lys Gln Ser Asn Asn Lys Tyr Ala Ala Ser
                165                 170                 175
Ser Tyr Leu Ser Leu Thr Pro Glu Gln Trp Lys Ser His Arg Ser Tyr
            180                 185                 190
Ser Cys Gln Val Thr His Glu Gly Ser Thr Val Glu Lys Thr Val Ala
        195                 200                 205
Pro Thr Glu Cys
210

<210> SEQ ID NO 17
<211> LENGTH: 454
<212> TYPE: PRT
<213> ORGANISM: Artificial Sequence
<220> FEATURE:
<223> OTHER INFORMATION: Synthetic Construct

<400> SEQUENCE: 17

Glu Val Gln Leu Val Glu Ser Gly Gly Gly Leu Val Gln Pro Gly Gly
 1               5                  10                  15
Ser Leu Arg Leu Ser Cys Ala Ala Ser Gly Phe Ser Leu Ser Gly Ser
             20                  25                  30
Trp Ile His Trp Val Arg Tyr Ala Pro Gly Lys Gly Leu Glu Trp Val
         35                  40                  45
Gly Trp Ile Asn Pro Tyr Arg Gly Tyr Ala Tyr Tyr Ala Asp Ser Val
 50                  55                  60
Lys Gly Arg Phe Thr Ile Ser Ala Asp Thr Ser Lys Asn Thr Ala Tyr
 65                  70                  75                  80
Leu Gln Met Asn Ser Leu Arg Ala Glu Asp Thr Ala Val Tyr Tyr Cys
                 85                  90                  95
Ala Arg Glu Tyr Ser Gly Trp Gly Gly Ser Ser Val Tyr Ala Met
            100                 105                 110
Asp Tyr Trp Gly Gln Gly Thr Leu Val Thr Val Ser Ser Ala Ser Thr
        115                 120                 125
Lys Gly Pro Ser Val Phe Pro Leu Ala Pro Ser Ser Lys Ser Thr Ser
130                 135                 140
Gly Gly Thr Ala Ala Leu Gly Cys Leu Val Lys Asp Tyr Phe Pro Glu
145                 150                 155                 160
Pro Val Thr Val Ser Trp Asn Ser Gly Ala Leu Thr Ser Gly Val His
                165                 170                 175
Thr Phe Pro Ala Val Leu Gln Ser Ser Gly Leu Tyr Ser Leu Ser Ser
            180                 185                 190
```

```
Val Val Thr Val Pro Ser Ser Leu Gly Thr Gln Thr Tyr Ile Cys
            195                 200                 205

Asn Val Asn His Lys Pro Ser Asn Thr Lys Val Asp Lys Lys Val Glu
210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
            245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln Tyr
290                 295                 300

Gln Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Lys Glu Leu Thr Lys
            355                 360                 365

Asn Gln Val Ser Leu Thr Cys Leu Val Lys Gly Phe Tyr Pro Ser Asp
            370                 375                 380

Ile Ala Val Glu Trp Glu Ser Asn Gly Gln Pro Glu Asn Asn Tyr Lys
385                 390                 395                 400

Thr Thr Pro Pro Val Leu Lys Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
            435                 440                 445

Leu Ser Leu Ser Pro Gly
    450

<210> SEQ ID NO 18
<211> LENGTH: 329
<212> TYPE: PRT
<213> ORGANISM: Artificial Sequence
<220> FEATURE:
<223> OTHER INFORMATION: Synthetic Construct

<400> SEQUENCE: 18

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val Ala Thr Gly Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95
```

```
Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly
            325

<210> SEQ ID NO 19
<211> LENGTH: 329
<212> TYPE: PRT
<213> ORGANISM: Artificial Sequence
<220> FEATURE:
<223> OTHER INFORMATION: Synthetic Construct

<400> SEQUENCE: 19

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val Ser Thr Gly Pro Ala Val Leu Gln Ser Ser Gly Leu Tyr Ser
50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
            85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125
```

```
Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 20
<211> LENGTH: 105
<212> TYPE: PRT
<213> ORGANISM: Artificial Sequence
<220> FEATURE:
<223> OTHER INFORMATION: Synthetic Construct

<400> SEQUENCE: 20

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Tyr Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
50                  55                  60

Lys Tyr Ala Ala Trp Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys
            100                 105

<210> SEQ ID NO 21
<211> LENGTH: 448
<212> TYPE: PRT
<213> ORGANISM: Artificial Sequence
<220> FEATURE:
<223> OTHER INFORMATION: Synthetic Construct

<400> SEQUENCE: 21
```

-continued

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Thr Asp Tyr
            20                  25                  30
Thr Met Asp Trp Val Arg Gln Ala Pro Gly Lys Gly Leu Glu Trp Val
        35                  40                  45
Ala Asp Val Asn Pro Asn Ser Gly Gly Ser Ile Tyr Asn Gln Glu Phe
    50                  55                  60
Lys Gly Arg Phe Thr Leu Ser Val Asp Arg Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Asn Leu Gly Pro Ser Phe Tyr Phe Asp Tyr Trp Gly Gln Gly
            100                 105                 110
Thr Leu Val Thr Val Ser Ser Ala Ser Thr Lys Gly Pro Ser Val Phe
        115                 120                 125
Pro Leu Ala Pro Ser Ser Lys Ser Thr Ser Gly Gly Thr Ala Ala Leu
    130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Lys Val Glu Pro Lys Ser Cys Asp Lys
    210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
        275                 280                 285
Ala Lys Thr Lys Pro Arg Glu Glu Gln Tyr Asn Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Asp Glu Leu Thr Lys Asn Gln Val Ser Leu Thr
        355                 360                 365
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
```

```
Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445
```

<210> SEQ ID NO 22
<211> LENGTH: 212
<212> TYPE: PRT
<213> ORGANISM: Artificial Sequence
<220> FEATURE:
<223> OTHER INFORMATION: Synthetic Construct

<400> SEQUENCE: 22

```
Arg Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys Gly Gln Pro Lys Ala
            100                 105                 110

Ala Pro Ser Val Thr Leu Phe Pro Pro Ser Ser Glu Glu Leu Gln Ala
        115                 120                 125

Asn Lys Ala Thr Leu Val Cys Leu Ile Ser Asp Phe Tyr Pro Gly Ala
130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Cys
    210
```

<210> SEQ ID NO 23
<211> LENGTH: 448
<212> TYPE: PRT
<213> ORGANISM: Artificial Sequence
<220> FEATURE:
<223> OTHER INFORMATION: Synthetic Construct

<400> SEQUENCE: 23

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Lys Ala Pro Gly Lys Gly Leu Glu Trp Val
        35                  40                  45

Ala Asp Val Asn Pro Asn Ser Gly Gly Ser Ile Tyr Asn Gln Arg Phe
50                  55                  60
```

```
Lys Gly Arg Phe Thr Leu Ser Val Asp Arg Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 24
<211> LENGTH: 212
<212> TYPE: PRT
<213> ORGANISM: Artificial Sequence
<220> FEATURE:
```

<223> OTHER INFORMATION: Synthetic Construct

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Asp Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys Gly Gln Pro Lys Ala
            100                 105                 110

Ala Pro Ser Val Thr Leu Phe Pro Pro Ser Ser Glu Glu Leu Gln Ala
        115                 120                 125

Asn Lys Ala Thr Leu Val Cys Leu Ile Ser Asp Phe Tyr Pro Gly Ala
    130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Cys
    210

<210> SEQ ID NO 25
<211> LENGTH: 448
<212> TYPE: PRT
<213> ORGANISM: Artificial Sequence
<220> FEATURE:
<223> OTHER INFORMATION: Synthetic Construct

<400> SEQUENCE: 25

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Lys Ala Pro Gly Lys Gly Leu Glu Trp Val
        35                  40                  45

Ala Asp Val Asn Pro Asn Ser Gly Gly Ser Ile Tyr Asn Gln Glu Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 26
<211> LENGTH: 212
<212> TYPE: PRT
<213> ORGANISM: Artificial Sequence
<220> FEATURE:
<223> OTHER INFORMATION: Synthetic Construct

<400> SEQUENCE: 26

Arg Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Asp Lys Pro Gly Lys Ala Pro Lys Leu Leu Ile
        35                  40                  45

```
Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys Gly Gln Pro Lys Ala
            100                 105                 110

Ala Pro Ser Val Thr Leu Phe Pro Pro Ser Ser Glu Glu Leu Gln Ala
        115                 120                 125

Asn Lys Ala Thr Leu Val Cys Leu Ile Ser Asp Phe Tyr Pro Gly Ala
    130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Cys
    210

<210> SEQ ID NO 27
<211> LENGTH: 448
<212> TYPE: PRT
<213> ORGANISM: Artificial Sequence
<220> FEATURE:
<223> OTHER INFORMATION: Synthetic Construct

<400> SEQUENCE: 27

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Lys Tyr Phe Pro Glu Pro Val Thr Val Ser Trp
145                 150                 155                 160

Asn Ser Gly Ala Leu Thr Ser Gly Val His Thr Thr Pro Ala Val Leu
                165                 170                 175

Gln Ser Ser Gly Leu Tyr Ser Leu Ser Ser Phe Val Thr Val Pro Ser
            180                 185                 190
```

```
Ser Ser Leu Gly Thr Gln Thr Tyr Ile Cys Asn Val Asn His Lys Pro
        195                 200                 205
Ser Asn Thr Lys Val Asp Lys Val Glu Pro Lys Ser Cys Asp Lys
210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
        275                 280                 285
Ala Lys Thr Lys Pro Arg Glu Glu Gln Tyr Asn Ser Thr Tyr Arg Val
290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Asp Glu Leu Thr Lys Asn Gln Val Ser Leu Thr
        355                 360                 365
Cys Leu Val Lys Gly Phe Tyr Pro Ser Asp Ile Ala Val Glu Trp Glu
370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
        435                 440                 445

<210> SEQ ID NO 28
<211> LENGTH: 212
<212> TYPE: PRT
<213> ORGANISM: Artificial Sequence
<220> FEATURE:
<223> OTHER INFORMATION: Synthetic Construct

<400> SEQUENCE: 28

Asp Ile Gln Met Thr Gln Ser Pro Ser Ser Leu Ser Ala Ser Val Gly
1               5                   10                  15
Asp Arg Val Thr Ile Thr Cys Lys Ala Ser Gln Asp Val Ser Ile Gly
            20                  25                  30
Val Ala Trp Tyr Gln Gln Lys Pro Gly Lys Ala Pro Lys Leu Leu Ile
        35                  40                  45
Tyr Ser Ala Ser Tyr Arg Tyr Thr Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Tyr Tyr Ile Tyr Pro Tyr
                85                  90                  95
Thr Phe Gly Gln Gly Thr Lys Val Glu Ile Lys Gly Gln Pro Lys Ala
            100                 105                 110
```

```
Ala Pro Ser Val Thr Leu Phe Pro Pro Ser Ser Glu Glu Leu Gln Ala
            115                 120                 125

Asn Asp Ala Thr Leu Val Cys Phe Ile Ser Asp Phe Tyr Pro Gly Ala
130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
            195                 200                 205

Pro Thr Glu Cys
    210
```

<210> SEQ ID NO 29
<211> LENGTH: 448
<212> TYPE: PRT
<213> ORGANISM: Artificial Sequence
<220> FEATURE:
<223> OTHER INFORMATION: Synthetic Construct

<400> SEQUENCE: 29

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Tyr Ala Pro Gly Lys Gly Leu Glu Trp Val
        35                  40                  45

Ala Asp Val Asn Pro Asn Ser Gly Gly Ser Ile Tyr Asn Gln Arg Phe
50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255
```

-continued

```
Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

<210> SEQ ID NO 30
<211> LENGTH: 212
<212> TYPE: PRT
<213> ORGANISM: Artificial Sequence
<220> FEATURE:
<223> OTHER INFORMATION: Synthetic Construct

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Arg Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ile Tyr Pro Tyr
                85                  90                  95

Thr Phe Gly Gln Gly Thr Lys Val Glu Ile Lys Gly Gln Pro Lys Ala
            100                 105                 110

Ala Pro Ser Val Thr Leu Phe Pro Pro Ser Ser Glu Glu Leu Gln Ala
            115                 120                 125

Asn Lys Ala Thr Leu Val Cys Leu Ile Ser Asp Phe Tyr Pro Gly Ala
        130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175
```

```
Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Cys
    210

<210> SEQ ID NO 31
<211> LENGTH: 448
<212> TYPE: PRT
<213> ORGANISM: Artificial Sequence
<220> FEATURE:
<223> OTHER INFORMATION: Synthetic Construct

<400> SEQUENCE: 31

Glu Val Gln Leu Val Glu Ser Gly Gly Gly Leu Val Gln Pro Gly Gly
1               5                  10                  15

Ser Leu Arg Leu Ser Cys Ala Ala Ser Gly Phe Thr Phe Thr Asp Tyr
            20                  25                  30

Thr Met Asp Trp Val Arg Phe Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320
```

```
Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 32
<211> LENGTH: 448
<212> TYPE: PRT
<213> ORGANISM: Artificial Sequence
<220> FEATURE:
<223> OTHER INFORMATION: Synthetic Construct

<400> SEQUENCE: 32

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Trp Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Lys Ser Cys Asp Lys
    210                 215                 220

Thr His Thr Cys Pro Pro Cys Pro Ala Pro Glu Leu Leu Gly Gly Pro
225                 230                 235                 240
```

```
Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
        260                 265                 270

Pro Glu Val Lys Phe Asn Trp Tyr Val Asp Gly Val Glu Val His Asn
    275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 33
<211> LENGTH: 214
<212> TYPE: PRT
<213> ORGANISM: Artificial Sequence
<220> FEATURE:
<223> OTHER INFORMATION: Synthetic Construct

<400> SEQUENCE: 33

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 34
<211> LENGTH: 214
<212> TYPE: PRT
<213> ORGANISM: Artificial Sequence
<220> FEATURE:
<223> OTHER INFORMATION: Synthetic Construct

<400> SEQUENCE: 34

Arg Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Asp Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 35
<211> LENGTH: 448
<212> TYPE: PRT
<213> ORGANISM: Artificial Sequence
<220> FEATURE:
<223> OTHER INFORMATION: Synthetic Construct

<400> SEQUENCE: 35

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr

```
                20                  25                  30
Thr Met Asp Trp Val Arg Gln Ala Pro Gly Lys Gly Leu Glu Trp Val
            35                  40                  45

Ala Asp Val Asn Pro Asn Ser Gly Gly Ser Ile Tyr Asn Gln Arg Phe
 50                  55                  60

Lys Gly Arg Phe Thr Leu Ser Val Asp Arg Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445
```

<210> SEQ ID NO 36
<211> LENGTH: 212
<212> TYPE: PRT
<213> ORGANISM: Artificial Sequence
<220> FEATURE:
<223> OTHER INFORMATION: Synthetic Construct

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys Gly Gln Pro Lys Ala
            100                 105                 110

Ala Pro Ser Val Thr Leu Phe Pro Pro Ser Ser Glu Glu Leu Gln Ala
        115                 120                 125

Asn Lys Ala Thr Leu Val Cys Tyr Ile Ser Asp Phe Tyr Pro Gly Ala
    130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Trp
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Cys
    210

<210> SEQ ID NO 37
<211> LENGTH: 448
<212> TYPE: PRT
<213> ORGANISM: Artificial Sequence
<220> FEATURE:
<223> OTHER INFORMATION: Synthetic Construct

<400> SEQUENCE: 37

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Lys Ala Pro Gly Lys Gly Leu Glu Trp Val
        35                  40                  45

Ala Asp Val Asn Pro Asn Ser Gly Gly Ser Ile Tyr Asn Gln Glu Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys

```
                85                  90                  95
Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
            210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

<210> SEQ ID NO 38
<211> LENGTH: 212
<212> TYPE: PRT
<213> ORGANISM: Artificial Sequence
<220> FEATURE:
<223> OTHER INFORMATION: Synthetic Construct

<400> SEQUENCE: 38

Arg Ile Gln Met Thr Gln Ser Pro Ser Ser Leu Ser Ala Ser Val Gly
```

```
            1               5                  10                 15
Asp Arg Val Thr Ile Thr Cys Lys Ala Ser Gln Asp Val Ser Ile Gly
                    20                 25                 30

Val Ala Trp Tyr Gln Asp Lys Pro Gly Lys Ala Pro Lys Leu Leu Ile
            35                 40                 45

Tyr Ser Ala Ser Tyr Arg Tyr Thr Gly Val Pro Ser Arg Phe Ser Gly
            50                 55                 60

Ser Gly Ser Gly Thr Asp Phe Thr Leu Thr Ile Ser Ser Leu Gln Pro
65                  70                 75                 80

Glu Asp Phe Ala Thr Tyr Tyr Cys Gln Gln Tyr Tyr Ile Tyr Pro Tyr
                    85                 90                 95

Thr Phe Gly Gln Gly Thr Lys Val Glu Ile Lys Gly Gln Pro Lys Ala
            100                105                110

Ala Pro Ser Val Thr Leu Phe Pro Pro Ser Ser Glu Glu Leu Gln Ala
            115                120                125

Asn Lys Ala Thr Leu Val Cys Tyr Ile Ser Asp Phe Tyr Pro Gly Ala
            130                135                140

Val Thr Val Ala Trp Lys Ala Asp Ser Ser Pro Val Lys Ala Gly Val
145                 150                155                160

Glu Thr Thr Thr Pro Ser Lys Gln Ser Asn Asn Lys Tyr Ala Ala Trp
                    165                170                175

Ser Tyr Leu Ser Leu Thr Pro Glu Gln Trp Lys Ser His Arg Ser Tyr
            180                185                190

Ser Cys Gln Val Thr His Glu Gly Ser Thr Val Glu Lys Thr Val Ala
            195                200                205

Pro Thr Glu Cys
            210

<210> SEQ ID NO 39
<211> LENGTH: 448
<212> TYPE: PRT
<213> ORGANISM: Artificial Sequence
<220> FEATURE:
<223> OTHER INFORMATION: Synthetic Construct

<400> SEQUENCE: 39

Glu Val Gln Leu Val Glu Ser Gly Gly Gly Leu Val Gln Pro Gly Gly
1               5                  10                 15

Ser Leu Arg Leu Ser Cys Ala Ala Ser Gly Phe Thr Phe Thr Asp Tyr
                    20                 25                 30

Thr Met Asp Trp Val Arg Tyr Ala Pro Gly Lys Gly Leu Glu Trp Val
            35                 40                 45

Ala Asp Val Asn Pro Asn Ser Gly Gly Ser Ile Tyr Asn Gln Arg Phe
            50                 55                 60

Lys Gly Arg Phe Thr Leu Ser Val Asp Arg Ser Lys Asn Thr Leu Tyr
65                  70                 75                 80

Leu Gln Met Asn Ser Leu Arg Ala Glu Asp Thr Ala Val Tyr Tyr Cys
                    85                 90                 95

Ala Arg Asn Leu Gly Pro Ser Phe Tyr Phe Asp Tyr Trp Gly Gln Gly
            100                105                110

Thr Leu Val Thr Val Ser Ser Ala Ser Thr Lys Gly Pro Ser Val Phe
            115                120                125

Pro Leu Ala Pro Ser Ser Lys Ser Thr Ser Gly Gly Thr Ala Ala Leu
            130                135                140

Gly Cys Leu Val Lys Asp Tyr Phe Pro Glu Pro Val Thr Val Ser Trp
```

```
                145                 150                 155                 160
        Asn Ser Gly Ala Leu Thr Ser Gly Val Ala Thr Gly Pro Ala Val Leu
                        165                 170                 175

Gln Ser Ser Gly Leu Tyr Ser Leu Ser Ser Val Val Thr Val Pro Ser
                        180                 185                 190

Ser Ser Leu Gly Thr Gln Thr Tyr Ile Cys Asn Val Asn His Lys Pro
                        195                 200                 205

Ser Asn Thr Lys Val Asp Lys Lys Val Glu Pro Lys Ser Cys Asp Lys
                210                 215                 220

Thr His Thr Cys Pro Pro Cys Pro Ala Pro Glu Leu Leu Gly Gly Pro
        225                 230                 235                 240

Ser Val Phe Leu Phe Pro Pro Lys Pro Lys Asp Thr Leu Met Ile Ser
                        245                 250                 255

Arg Thr Pro Glu Val Thr Cys Val Val Val Asp Val Ser His Glu Asp
                        260                 265                 270

Pro Glu Val Lys Phe Asn Trp Tyr Val Asp Gly Val Glu Val His Asn
                        275                 280                 285

Ala Lys Thr Lys Pro Arg Glu Glu Gln Tyr Asn Ser Thr Tyr Arg Val
                290                 295                 300

Val Ser Val Leu Thr Val Leu His Gln Asp Trp Leu Asn Gly Lys Glu
        305                 310                 315                 320

Tyr Lys Cys Lys Val Ser Asn Lys Ala Leu Pro Ala Pro Ile Glu Lys
                        325                 330                 335

Thr Ile Ser Lys Ala Lys Gly Gln Pro Arg Glu Pro Gln Val Tyr Thr
                        340                 345                 350

Leu Pro Pro Ser Arg Asp Glu Leu Thr Lys Asn Gln Val Ser Leu Thr
                        355                 360                 365

Cys Leu Val Lys Gly Phe Tyr Pro Ser Asp Ile Ala Val Glu Trp Glu
                370                 375                 380

Ser Asn Gly Gln Pro Glu Asn Asn Tyr Lys Thr Thr Pro Pro Val Leu
        385                 390                 395                 400

Asp Ser Asp Gly Ser Phe Phe Leu Tyr Ser Lys Leu Thr Val Asp Lys
                        405                 410                 415

Ser Arg Trp Gln Gln Gly Asn Val Phe Ser Cys Ser Val Met His Glu
                        420                 425                 430

Ala Leu His Asn His Tyr Thr Gln Lys Ser Leu Ser Leu Ser Pro Gly
                        435                 440                 445

<210> SEQ ID NO 40
<211> LENGTH: 212
<212> TYPE: PRT
<213> ORGANISM: Artificial Sequence
<220> FEATURE:
<223> OTHER INFORMATION: Synthetic Construct

<400> SEQUENCE: 40

Asp Ile Gln Met Thr Gln Ser Pro Ser Ser Leu Ser Ala Ser Val Gly
        1               5                   10                  15

Asp Arg Val Thr Ile Thr Cys Lys Ala Ser Gln Asp Val Ser Ile Gly
                        20                  25                  30

Val Ala Trp Tyr Gln Arg Lys Pro Gly Lys Ala Pro Lys Leu Leu Ile
                        35                  40                  45

Tyr Ser Ala Ser Tyr Arg Tyr Thr Gly Val Pro Ser Arg Phe Ser Gly
                50                  55                  60

Ser Gly Ser Gly Thr Asp Phe Thr Leu Thr Ile Ser Ser Leu Gln Pro
```

```
                65                  70                  75                  80
Glu Asp Phe Ala Thr Tyr Tyr Cys Gln Gln Tyr Tyr Ile Tyr Pro Tyr
                    85                  90                  95

Thr Phe Gly Gln Gly Thr Lys Val Glu Ile Lys Gly Gln Pro Lys Ala
                100                 105                 110

Ala Pro Ser Val Thr Leu Phe Pro Pro Ser Ser Glu Glu Leu Gln Ala
                115                 120                 125

Asn Lys Ala Thr Leu Val Cys Tyr Ile Ser Asp Phe Tyr Pro Gly Ala
                130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Trp
                    165                 170                 175

Ser Tyr Leu Ser Leu Thr Pro Glu Gln Trp Lys Ser His Arg Ser Tyr
                    180                 185                 190

Ser Cys Gln Val Thr His Glu Gly Ser Thr Val Glu Lys Thr Val Ala
                    195                 200                 205

Pro Thr Glu Cys
                210

<210> SEQ ID NO 41
<211> LENGTH: 214
<212> TYPE: PRT
<213> ORGANISM: Artificial Sequence
<220> FEATURE:
<223> OTHER INFORMATION: Synthetic Construct

<400> SEQUENCE: 41

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
                20                  25                  30

Val Ala Trp Tyr Gln Arg Lys Pro Gly Lys Ala Pro Lys Leu Leu Ile
            35                  40                  45

Tyr Ser Ala Ser Tyr Arg Tyr Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                    85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
                130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                    165                 170                 175

Ser Thr Leu Thr Leu Ser Lys Ala Asp Tyr Glu Lys His Lys Val Tyr
                    180                 185                 190

Ala Cys Glu Val Thr His Gln Gly Leu Ser Ser Pro Val Thr Lys Ser
                    195                 200                 205

Phe Asn Arg Gly Glu Cys
```

```
<210> SEQ ID NO 42
<211> LENGTH: 212
<212> TYPE: PRT
<213> ORGANISM: Artificial Sequence
<220> FEATURE:
<223> OTHER INFORMATION: Synthetic Construct

<400> SEQUENCE: 42

Arg Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Asp Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys Gly Gln Pro Lys Ala
            100                 105                 110

Ala Pro Ser Val Thr Leu Phe Pro Pro Ser Ser Glu Glu Leu Gln Ala
        115                 120                 125

Asn Lys Ala Thr Leu Val Cys Phe Ile Ser Asp Phe Tyr Pro Gly Ala
130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Trp
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Cys
    210

<210> SEQ ID NO 43
<211> LENGTH: 450
<212> TYPE: PRT
<213> ORGANISM: Artificial Sequence
<220> FEATURE:
<223> OTHER INFORMATION: Synthetic Construct

<400> SEQUENCE: 43

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
            20                  25                  30

Trp Met His Trp Val Arg Gln Ala Pro Gly Gln Gly Leu Glu Trp Ile
        35                  40                  45

Gly Glu Phe Asn Pro Ser Asn Gly Arg Thr Asn Tyr Asn Glu Lys Phe
    50                  55                  60

Lys Ser Lys Ala Thr Met Thr Val Asp Thr Ser Thr Asn Thr Ala Tyr
65                  70                  75                  80
```

```
Met Glu Leu Ser Ser Leu Arg Ser Glu Asp Thr Ala Val Tyr Tyr Cys
                 85                  90                  95

Ala Ser Arg Asp Tyr Asp Tyr Asp Gly Arg Tyr Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450

<210> SEQ ID NO 44
<211> LENGTH: 211
<212> TYPE: PRT
<213> ORGANISM: Artificial Sequence
<220> FEATURE:
<223> OTHER INFORMATION: Synthetic Construct
```

<400> SEQUENCE: 44

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Thr Tyr Met
            20                  25                  30

Tyr Trp Tyr Gln Gln Lys Pro Gly Lys Ala Pro Lys Leu Leu Ile Tyr
        35                  40                  45

Asp Thr Ser Asn Leu Ala Ser Gly Val Pro Ser Arg Phe Ser Gly Ser
    50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln Gln Trp Ser Ser His Ile Phe Thr
                85                  90                  95

Phe Gly Gln Gly Thr Lys Val Glu Ile Lys Gly Gln Pro Lys Ala Ala
            100                 105                 110

Pro Ser Val Thr Leu Phe Pro Pro Ser Ser Glu Glu Leu Gln Ala Asn
        115                 120                 125

Lys Ala Thr Leu Val Cys Leu Ile Ser Asp Phe Tyr Pro Gly Ala Val
    130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
        195                 200                 205

Thr Glu Cys
    210

<210> SEQ ID NO 45
<211> LENGTH: 213
<212> TYPE: PRT
<213> ORGANISM: Artificial Sequence
<220> FEATURE:
<223> OTHER INFORMATION: Synthetic Construct

<400> SEQUENCE: 45

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Thr Tyr Met
            20                  25                  30

Tyr Trp Tyr Gln Gln Lys Pro Gly Lys Ala Pro Lys Leu Leu Ile Tyr
        35                  40                  45

Asp Thr Ser Asn Leu Ala Ser Gly Val Pro Ser Arg Phe Ser Gly Ser
    50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln Gln Trp Ser Ser His Ile Phe Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

```
Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
    210

<210> SEQ ID NO 46
<211> LENGTH: 448
<212> TYPE: PRT
<213> ORGANISM: Artificial Sequence
<220> FEATURE:
<223> OTHER INFORMATION: Synthetic Construct

<400> SEQUENCE: 46

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Trp Leu His Trp Val Arg Lys Ala Pro Gly Lys Gly Leu Glu Trp Val
        35                  40                  45

Gly Met Ile Asp Pro Ser Asn Ser Asp Thr Arg Phe Asn Pro Asn Phe
    50                  55                  60

Lys Asp Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Thr Tyr Arg Ser Tyr Val Thr Pro Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270
```

```
Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 47
<211> LENGTH: 218
<212> TYPE: PRT
<213> ORGANISM: Artificial Sequence
<220> FEATURE:
<223> OTHER INFORMATION: Synthetic Construct

<400> SEQUENCE: 47

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Tyr Thr
            20                  25                  30

Ser Ser Gln Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Tyr Tyr Ala Tyr Pro Trp Thr Phe Gly Gln Gly Thr Lys Val Glu Ile
            100                 105                 110

Lys Gly Gln Pro Lys Ala Ala Pro Ser Val Thr Leu Phe Pro Pro Ser
        115                 120                 125

Ser Glu Glu Leu Gln Ala Asn Lys Ala Thr Leu Val Cys Leu Ile Ser
    130                 135                 140

Asp Phe Tyr Pro Gly Ala Val Thr Val Ala Trp Lys Ala Asp Ser Ser
145                 150                 155                 160

Pro Val Lys Ala Gly Val Glu Thr Thr Thr Pro Ser Lys Gln Ser Asn
                165                 170                 175

Asn Lys Tyr Ala Ala Ser Ser Tyr Leu Ser Leu Thr Pro Glu Gln Trp
            180                 185                 190
```

```
Lys Ser His Arg Ser Tyr Ser Cys Gln Val Thr His Glu Gly Ser Thr
            195                 200                 205

Val Glu Lys Thr Val Ala Pro Thr Glu Cys
    210                 215

<210> SEQ ID NO 48
<211> LENGTH: 220
<212> TYPE: PRT
<213> ORGANISM: Artificial Sequence
<220> FEATURE:
<223> OTHER INFORMATION: Synthetic Construct

<400> SEQUENCE: 48

Asp Ile Gln Met Thr Gln Ser Pro Ser Ser Leu Ser Ala Ser Val Gly
1               5                   10                  15

Asp Arg Val Thr Ile Thr Cys Lys Ser Gln Ser Leu Leu Tyr Thr
            20                  25                  30

Ser Ser Gln Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Tyr Tyr Ala Tyr Pro Trp Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 49
<211> LENGTH: 454
<212> TYPE: PRT
<213> ORGANISM: Artificial Sequence
<220> FEATURE:
<223> OTHER INFORMATION: Synthetic Construct

<400> SEQUENCE: 49

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Gly Ser
            20                  25                  30

Trp Ile His Trp Val Arg Gln Ala Pro Gly Lys Gly Leu Glu Trp Val
        35                  40                  45

Gly Trp Ile Asn Pro Tyr Arg Gly Tyr Ala Tyr Tyr Ala Asp Ser Val
    50                  55                  60
```

```
Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
             85                  90                  95

Ala Arg Glu Tyr Ser Gly Trp Gly Gly Ser Val Gly Tyr Ala Met
            100                 105                 110

Asp Tyr Trp Gly Gln Gly Thr Leu Val Thr Val Ser Ser Ala Ser Thr
            115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly
450

<210> SEQ ID NO 50
<211> LENGTH: 212
```

<212> TYPE: PRT
<213> ORGANISM: Artificial Sequence
<220> FEATURE:
<223> OTHER INFORMATION: Synthetic Construct

<400> SEQUENCE: 50

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Pro
                85                  90                  95

Thr Phe Gly Gln Gly Thr Lys Val Glu Ile Lys Gly Gln Pro Lys Ala
            100                 105                 110

Ala Pro Ser Val Thr Leu Phe Pro Pro Ser Ser Glu Glu Leu Gln Ala
        115                 120                 125

Asn Lys Ala Thr Leu Val Cys Leu Ile Ser Asp Phe Tyr Pro Gly Ala
130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Cys
    210

<210> SEQ ID NO 51
<211> LENGTH: 214
<212> TYPE: PRT
<213> ORGANISM: Artificial Sequence
<220> FEATURE:
<223> OTHER INFORMATION: Synthetic Construct

<400> SEQUENCE: 51

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Pro
                85                  90                  95

Thr Phe Gly Gln Gly Thr Lys Val Glu Ile Lys Arg Thr Val Ala Ala
            100                 105                 110

```
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
        210

<210> SEQ ID NO 52
<211> LENGTH: 448
<212> TYPE: PRT
<213> ORGANISM: Artificial Sequence
<220> FEATURE:
<223> OTHER INFORMATION: Synthetic Construct

<400> SEQUENCE: 52

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255
```

```
Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Gln Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Asp Thr Thr Pro Pro Val Leu
385                 390                 395                 400

Asp Ser Asp Gly Ser Phe Phe Leu Tyr Ser Asp Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

<210> SEQ ID NO 53
<211> LENGTH: 450
<212> TYPE: PRT
<213> ORGANISM: Artificial Sequence
<220> FEATURE:
<223> OTHER INFORMATION: Synthetic Construct

<400> SEQUENCE: 53

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
            20                  25                  30

Trp Met His Trp Val Arg Gln Ala Pro Gly Gln Gly Leu Glu Trp Ile
        35                  40                  45

Gly Glu Phe Asn Pro Ser Asn Gly Arg Thr Asn Tyr Asn Glu Lys Phe
    50                  55                  60

Lys Ser Lys Ala Thr Met Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Ser Arg Asp Tyr Asp Tyr Asp Gly Arg Tyr Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175
```

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
        210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Gln Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
            340                 345                 350

Tyr Thr Leu Pro Pro Ser Arg Lys Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Lys Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450

<210> SEQ ID NO 54
<211> LENGTH: 448
<212> TYPE: PRT
<213> ORGANISM: Artificial Sequence
<220> FEATURE:
<223> OTHER INFORMATION: Synthetic Construct

<400> SEQUENCE: 54

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Trp Leu His Trp Val Arg Gln Ala Pro Gly Lys Gly Leu Glu Trp Val
        35                  40                  45

Gly Met Ile Asp Pro Ser Asn Ser Asp Thr Arg Phe Asn Pro Asn Phe
    50                  55                  60

Lys Asp Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Thr Tyr Arg Ser Tyr Val Thr Pro Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Gln Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Asp Thr Thr Pro Pro Val Leu
385                 390                 395                 400

Asp Ser Asp Gly Ser Phe Phe Leu Tyr Ser Asp Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 55
<211> LENGTH: 454
<212> TYPE: PRT
<213> ORGANISM: Artificial Sequence
<220> FEATURE:
<223> OTHER INFORMATION: Synthetic Construct

<400> SEQUENCE: 55

```
Glu Val Gln Leu Val Glu Ser Gly Gly Gly Leu Val Gln Pro Gly Gly
 1               5                  10                 15

Ser Leu Arg Leu Ser Cys Ala Ala Ser Gly Phe Ser Leu Ser Gly Ser
            20                  25                 30

Trp Ile His Trp Val Arg Gln Ala Pro Gly Lys Gly Leu Glu Trp Val
        35                  40                 45

Gly Trp Ile Asn Pro Tyr Arg Gly Tyr Ala Tyr Ala Asp Ser Val
    50                  55                 60

Lys Gly Arg Phe Thr Ile Ser Ala Asp Thr Ser Lys Asn Thr Ala Tyr
65                  70                  75                 80

Leu Gln Met Asn Ser Leu Arg Ala Glu Asp Thr Ala Val Tyr Tyr Cys
                85                  90                 95

Ala Arg Glu Tyr Ser Gly Trp Gly Gly Ser Ser Val Gly Tyr Ala Met
            100                 105                110

Asp Tyr Trp Gly Gln Gly Thr Leu Val Thr Val Ser Ser Ala Ser Thr
        115                 120                125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                160

Pro Val Thr Val Ser Trp Asn Ser Gly Ala Leu Thr Ser Gly Val His
                165                 170                175

Thr Phe Pro Ala Val Leu Gln Ser Ser Gly Leu Tyr Ser Leu Ser Ser
            180                 185                190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
210                 215                 220

Pro Lys Ser Cys Asp Lys Thr His Thr Cys Pro Pro Cys Pro Ala Pro
225                 230                 235                240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Gln Ser Thr Tyr Arg Val Val Ser Val Leu Thr Val Leu His Gln Asp
305                 310                 315                320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Lys Glu Leu Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                400

Thr Thr Pro Pro Val Leu Lys Ser Asp Gly Ser Phe Phe Leu Tyr Ser
                405                 410                 415
```

```
Lys Leu Thr Val Asp Lys Ser Arg Trp Gln Gln Gly Asn Val Phe Ser
                420                 425                 430

Cys Ser Val Met His Glu Ala Leu His Asn His Tyr Thr Gln Lys Ser
            435                 440                 445

Leu Ser Leu Ser Pro Gly
        450

<210> SEQ ID NO 56
<211> LENGTH: 214
<212> TYPE: PRT
<213> ORGANISM: Artificial Sequence
<220> FEATURE:
<223> OTHER INFORMATION: Synthetic Construct

<400> SEQUENCE: 56

Arg Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Asp Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Tyr Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Trp
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 57
<211> LENGTH: 450
<212> TYPE: PRT
<213> ORGANISM: Artificial Sequence
<220> FEATURE:
<223> OTHER INFORMATION: Synthetic Construct

<400> SEQUENCE: 57

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
            20                  25                  30

Trp Met His Trp Val Arg Tyr Ala Pro Gly Gln Gly Leu Glu Trp Ile
        35                  40                  45
```

```
Gly Glu Phe Asn Pro Ser Asn Gly Arg Thr Asn Tyr Asn Glu Lys Phe
    50                  55                  60

Lys Ser Lys Ala Thr Met Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Ser Arg Asp Tyr Asp Tyr Asp Gly Arg Tyr Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Gln Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Lys Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Lys Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450
```

<210> SEQ ID NO 58
<211> LENGTH: 211
<212> TYPE: PRT
<213> ORGANISM: Artificial Sequence
<220> FEATURE:
<223> OTHER INFORMATION: Synthetic Construct

<400> SEQUENCE: 58

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Thr Tyr Met
            20                  25                  30

Tyr Trp Tyr Gln Arg Lys Pro Gly Lys Ala Pro Lys Leu Leu Ile Tyr
        35                  40                  45

Asp Thr Ser Asn Leu Ala Ser Gly Val Pro Ser Arg Phe Ser Gly Ser
    50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln Gln Trp Ser Ser His Ile Phe Thr
                85                  90                  95

Phe Gly Gln Gly Thr Lys Val Glu Ile Lys Gly Gln Pro Lys Ala Ala
            100                 105                 110

Pro Ser Val Thr Leu Phe Pro Pro Ser Ser Glu Glu Leu Gln Ala Asn
        115                 120                 125

Lys Ala Thr Leu Val Cys Leu Ile Ser Asp Phe Tyr Pro Gly Ala Val
    130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
        195                 200                 205

Thr Glu Cys
    210

<210> SEQ ID NO 59
<211> LENGTH: 213
<212> TYPE: PRT
<213> ORGANISM: Artificial Sequence
<220> FEATURE:
<223> OTHER INFORMATION: Synthetic Construct

<400> SEQUENCE: 59

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Thr Tyr Met
            20                  25                  30

Tyr Trp Tyr Gln Arg Lys Pro Gly Lys Ala Pro Lys Leu Leu Ile Tyr
        35                  40                  45

Asp Thr Ser Asn Leu Ala Ser Gly Val Pro Ser Arg Phe Ser Gly Ser
    50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln Gln Trp Ser Ser His Ile Phe Thr
                85                  90                  95

```
Phe Gly Gln Gly Thr Lys Val Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
    210

<210> SEQ ID NO 60
<211> LENGTH: 448
<212> TYPE: PRT
<213> ORGANISM: Artificial Sequence
<220> FEATURE:
<223> OTHER INFORMATION: Synthetic Construct

<400> SEQUENCE: 60

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Trp Leu His Trp Val Arg Lys Ala Pro Gly Lys Gly Leu Glu Trp Val
        35                  40                  45

Gly Met Ile Asp Pro Ser Asn Ser Asp Thr Arg Phe Asn Pro Glu Phe
    50                  55                  60

Lys Asp Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Thr Tyr Arg Ser Tyr Val Thr Pro Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val Ala Thr Gly Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240
```

```
Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Gln Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Asp Thr Thr Pro Pro Val Leu
385                 390                 395                 400

Asp Ser Asp Gly Ser Phe Phe Leu Tyr Ser Asp Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 61
<211> LENGTH: 218
<212> TYPE: PRT
<213> ORGANISM: Artificial Sequence
<220> FEATURE:
<223> OTHER INFORMATION: Synthetic Construct

<400> SEQUENCE: 61

Arg Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Tyr Thr
            20                  25                  30

Ser Ser Gln Lys Asn Tyr Leu Ala Trp Tyr Gln Asp Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Tyr Tyr Ala Tyr Pro Trp Thr Phe Gly Gln Gly Thr Lys Val Glu Ile
            100                 105                 110

Lys Gly Gln Pro Lys Ala Ala Pro Ser Val Thr Leu Phe Pro Pro Ser
        115                 120                 125

Ser Glu Glu Leu Gln Ala Asn Lys Ala Thr Leu Val Cys Tyr Ile Ser
    130                 135                 140

Asp Phe Tyr Pro Gly Ala Val Thr Val Ala Trp Lys Ala Asp Ser Ser
145                 150                 155                 160
```

```
Pro Val Lys Ala Gly Val Glu Thr Thr Thr Pro Ser Lys Gln Ser Asn
            165                 170                 175

Asn Lys Tyr Ala Ala Trp Ser Tyr Leu Ser Leu Thr Pro Glu Gln Trp
            180                 185                 190

Lys Ser His Arg Ser Tyr Ser Cys Gln Val Thr His Glu Gly Ser Thr
            195                 200                 205

Val Glu Lys Thr Val Ala Pro Thr Glu Cys
            210                 215

<210> SEQ ID NO 62
<211> LENGTH: 220
<212> TYPE: PRT
<213> ORGANISM: Artificial Sequence
<220> FEATURE:
<223> OTHER INFORMATION: Synthetic Construct

<400> SEQUENCE: 62

Arg Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Tyr Thr
            20                  25                  30

Ser Ser Gln Lys Asn Tyr Leu Ala Trp Tyr Gln Asp Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Tyr Tyr Ala Tyr Pro Trp Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Tyr Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Trp Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 63
<211> LENGTH: 107
<212> TYPE: PRT
<213> ORGANISM: Artificial Sequence
<220> FEATURE:
<223> OTHER INFORMATION: Synthetic Construct

<400> SEQUENCE: 63

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
```

```
                20                  25                  30
Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
        50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 64
<211> LENGTH: 107
<212> TYPE: PRT
<213> ORGANISM: Artificial Sequence
<220> FEATURE:
<223> OTHER INFORMATION: Synthetic Construct

<400> SEQUENCE: 64

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Tyr Leu Asn Asn Phe
            20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
        50                  55                  60

Thr Tyr Ser Leu Trp Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 65
<211> LENGTH: 329
<212> TYPE: PRT
<213> ORGANISM: Artificial Sequence
<220> FEATURE:
<223> OTHER INFORMATION: Synthetic Construct

<400> SEQUENCE: 65

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val Arg Thr Gly Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110
```

```
Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 66
<211> LENGTH: 329
<212> TYPE: PRT
<213> ORGANISM: Artificial Sequence
<220> FEATURE:
<223> OTHER INFORMATION: Synthetic Construct

<400> SEQUENCE: 66

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val Ala Thr Gly Pro Ala Val Leu Gln Ser Ser Gly Leu Tyr Ser
    50                  55                  60

Leu Ser Ser Met Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140
```

```
Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 67
<211> LENGTH: 329
<212> TYPE: PRT
<213> ORGANISM: Artificial Sequence
<220> FEATURE:
<223> OTHER INFORMATION: Synthetic Construct

<400> SEQUENCE: 67

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val Ala Thr Gly Pro Ala Val Leu Gln Ser Ser Gly Leu Tyr Ser
        50                  55                  60

Leu Ser Ser Ile Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175
```

```
Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
    275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 68
<211> LENGTH: 329
<212> TYPE: PRT
<213> ORGANISM: Artificial Sequence
<220> FEATURE:
<223> OTHER INFORMATION: Synthetic Construct

<400> SEQUENCE: 68

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val Arg Thr Gly Pro Ala Val Leu Gln Ser Ser Gly Leu Tyr Ser
    50                  55                  60

Leu Ser Ser Met Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205
```

```
Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325
```

```
<210> SEQ ID NO 69
<211> LENGTH: 329
<212> TYPE: PRT
<213> ORGANISM: Artificial Sequence
<220> FEATURE:
<223> OTHER INFORMATION: Synthetic Construct

<400> SEQUENCE: 69
```

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val Arg Thr Gly Pro Ala Val Leu Gln Ser Ser Gly Leu Tyr Ser
    50                  55                  60

Leu Ser Ser Ile Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240
```

```
Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 70
<211> LENGTH: 107
<212> TYPE: PRT
<213> ORGANISM: Artificial Sequence
<220> FEATURE:
<223> OTHER INFORMATION: Synthetic Construct

<400> SEQUENCE: 70

Arg Thr Val Ala Ala Pro Ser Val Phe Ile Phe Pro Pro Ser Asp Glu
1               5                   10                  15

Gln Leu Lys Ser Gly Thr Ala Ser Val Leu Cys Tyr Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Trp Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 71
<211> LENGTH: 107
<212> TYPE: PRT
<213> ORGANISM: Artificial Sequence
<220> FEATURE:
<223> OTHER INFORMATION: Synthetic Construct

<400> SEQUENCE: 71

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Tyr Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Gln Leu Trp Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 72
<211> LENGTH: 107
<212> TYPE: PRT
<213> ORGANISM: Artificial Sequence
<220> FEATURE:
<223> OTHER INFORMATION: Synthetic Construct

<400> SEQUENCE: 72

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Tyr Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Asp Leu Trp Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 73
<211> LENGTH: 107
<212> TYPE: PRT
<213> ORGANISM: Artificial Sequence
<220> FEATURE:
<223> OTHER INFORMATION: Synthetic Construct

<400> SEQUENCE: 73

Arg Thr Val Ala Ala Pro Ser Val Phe Ile Phe Pro Pro Ser Asp Glu
1               5                   10                  15

Gln Leu Lys Ser Gly Thr Ala Ser Val Leu Cys Tyr Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Gln Leu Trp Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 74
<211> LENGTH: 107
<212> TYPE: PRT
<213> ORGANISM: Artificial Sequence
<220> FEATURE:
<223> OTHER INFORMATION: Synthetic Construct

<400> SEQUENCE: 74

Arg Thr Val Ala Ala Pro Ser Val Phe Ile Phe Pro Pro Ser Asp Glu
1               5                   10                  15

Gln Leu Lys Ser Gly Thr Ala Ser Val Leu Cys Tyr Leu Asn Asn Phe
            20                  25                  30

```
Tyr Pro Arg Glu Ala Lys Val Gln Trp Lys Val Asp Asn Ala Leu Gln
         35                  40                  45

Ser Gly Asn Ser Gln Glu Ser Val Thr Glu Gln Asp Ser Lys Asp Ser
 50                  55                  60

Thr Tyr Asp Leu Trp Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105

<210> SEQ ID NO 75
<211> LENGTH: 448
<212> TYPE: PRT
<213> ORGANISM: Artificial Sequence
<220> FEATURE:
<223> OTHER INFORMATION: Synthetic Construct

<400> SEQUENCE: 75

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Thr Asp Tyr
             20                  25                  30

Thr Met Asp Trp Val Arg Lys Ala Pro Gly Lys Gly Leu Glu Trp Val
         35                  40                  45

Ala Asp Val Asn Pro Asn Ser Gly Gly Ser Ile Tyr Asn Gln Glu Phe
 50                  55                  60

Lys Gly Arg Phe Thr Leu Ser Val Asp Arg Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val Arg Thr Gly Pro Ala Val Leu
            165                 170                 175

Gln Ser Ser Gly Leu Tyr Ser Leu Ser Ser Met Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285
```

```
Ala Lys Thr Lys Pro Arg Glu Glu Gln Tyr Gln Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Asp Glu Leu Thr Lys Asn Gln Val Ser Leu Thr
        355                 360                 365
Cys Leu Val Lys Gly Phe Tyr Pro Ser Asp Ile Ala Val Glu Trp Glu
370                 375                 380
Ser Asn Gly Gln Pro Glu Asn Asn Tyr Asp Thr Thr Pro Pro Val Leu
385                 390                 395                 400
Asp Ser Asp Gly Ser Phe Phe Leu Tyr Ser Asp Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
        435                 440                 445

<210> SEQ ID NO 76
<211> LENGTH: 448
<212> TYPE: PRT
<213> ORGANISM: Artificial Sequence
<220> FEATURE:
<223> OTHER INFORMATION: Synthetic Construct

<400> SEQUENCE: 76

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Thr Asp Tyr
            20                  25                  30
Thr Met Asp Trp Val Arg Lys Ala Pro Gly Lys Gly Leu Glu Trp Val
        35                  40                  45
Ala Asp Val Asn Pro Asn Ser Gly Gly Ser Ile Tyr Asn Gln Glu Phe
    50                  55                  60
Lys Gly Arg Phe Thr Leu Ser Val Asp Arg Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Asn Leu Gly Pro Ser Phe Tyr Phe Asp Tyr Trp Gly Gln Gly
            100                 105                 110
Thr Leu Val Thr Val Ser Ser Ala Ser Thr Lys Gly Pro Ser Val Phe
        115                 120                 125
Pro Leu Ala Pro Ser Ser Lys Ser Thr Ser Gly Gly Thr Ala Ala Leu
    130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val Arg Thr Gly Pro Ala Val Leu
                165                 170                 175
Gln Ser Ser Gly Leu Tyr Ser Leu Ser Ser Ile Val Thr Val Pro Ser
            180                 185                 190
Ser Ser Leu Gly Thr Gln Thr Tyr Ile Cys Asn Val Asn His Lys Pro
        195                 200                 205
```

```
Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Gln Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Asp Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 77
<211> LENGTH: 448
<212> TYPE: PRT
<213> ORGANISM: Artificial Sequence
<220> FEATURE:
<223> OTHER INFORMATION: Synthetic Construct

<400> SEQUENCE: 77

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Trp Leu His Trp Val Arg Lys Ala Pro Gly Lys Gly Leu Glu Trp Val
        35                  40                  45

Gly Met Ile Asp Pro Ser Asn Ser Asp Thr Arg Phe Asn Pro Glu Phe
    50                  55                  60

Lys Asp Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Thr Tyr Arg Ser Tyr Val Thr Pro Leu Asp Tyr Trp Gly Gln Gly
            100                 105                 110

Thr Leu Val Thr Val Ser Ser Ala Ser Thr Lys Gly Pro Ser Val Phe
        115                 120                 125
```

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val Arg Thr Gly Pro Ala Val Leu
                165                 170                 175

Gln Ser Ser Gly Leu Tyr Ser Leu Ser Ser Met Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Gln Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Asp Thr Thr Pro Pro Val Leu
385                 390                 395                 400

Asp Ser Asp Gly Ser Phe Phe Leu Tyr Ser Asp Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 78
<211> LENGTH: 448
<212> TYPE: PRT
<213> ORGANISM: Artificial Sequence
<220> FEATURE:
<223> OTHER INFORMATION: Synthetic Construct

<400> SEQUENCE: 78

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Trp Leu His Trp Val Arg Lys Ala Pro Gly Lys Gly Leu Glu Trp Val
        35                  40                  45

```
Gly Met Ile Asp Pro Ser Asn Ser Asp Thr Arg Phe Asn Pro Glu Phe
     50                  55                  60
Lys Asp Arg Phe Thr Ile Ser Ala Asp Thr Ser Lys Asn Thr Ala Tyr
 65                  70                  75                  80
Leu Gln Met Asn Ser Leu Arg Ala Glu Asp Thr Ala Val Tyr Tyr Cys
                 85                  90                  95
Ala Thr Tyr Arg Ser Tyr Val Thr Pro Leu Asp Tyr Trp Gly Gln Gly
            100                 105                 110
Thr Leu Val Thr Val Ser Ser Ala Ser Thr Lys Gly Pro Ser Val Phe
            115                 120                 125
Pro Leu Ala Pro Ser Ser Lys Ser Thr Ser Gly Gly Thr Ala Ala Leu
130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val Arg Thr Gly Pro Ala Val Leu
                165                 170                 175
Gln Ser Ser Gly Leu Tyr Ser Leu Ser Ser Ile Val Thr Val Pro Ser
            180                 185                 190
Ser Ser Leu Gly Thr Gln Thr Tyr Ile Cys Asn Val Asn His Lys Pro
            195                 200                 205
Ser Asn Thr Lys Val Asp Lys Lys Val Glu Pro Lys Ser Cys Asp Lys
210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
            275                 280                 285
Ala Lys Thr Lys Pro Arg Glu Glu Gln Tyr Gln Ser Thr Tyr Arg Val
            290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Asp Glu Leu Thr Lys Asn Gln Val Ser Leu Thr
            355                 360                 365
Cys Leu Val Lys Gly Phe Tyr Pro Ser Asp Ile Ala Val Glu Trp Glu
370                 375                 380
Ser Asn Gly Gln Pro Glu Asn Asn Tyr Asp Thr Thr Pro Pro Val Leu
385                 390                 395                 400
Asp Ser Asp Gly Ser Phe Phe Leu Tyr Ser Asp Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
            435                 440                 445

<210> SEQ ID NO 79
<211> LENGTH: 214
<212> TYPE: PRT
```

<213> ORGANISM: Artificial Sequence
<220> FEATURE:
<223> OTHER INFORMATION: Synthetic Construct

<400> SEQUENCE: 79

```
Arg Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Asp Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Leu Cys Tyr Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Asp Leu Trp
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210
```

<210> SEQ ID NO 80
<211> LENGTH: 214
<212> TYPE: PRT
<213> ORGANISM: Artificial Sequence
<220> FEATURE:
<223> OTHER INFORMATION: Synthetic Construct

<400> SEQUENCE: 80

```
Arg Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Asp Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys Arg Thr Val Ala Ala
            100                 105                 110
```

```
Pro Ser Val Phe Ile Phe Pro Pro Ser Asp Glu Gln Leu Lys Ser Gly
            115                 120                 125

Thr Ala Ser Val Leu Cys Tyr Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Gln Leu Trp
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 81
<211> LENGTH: 220
<212> TYPE: PRT
<213> ORGANISM: Artificial Sequence
<220> FEATURE:
<223> OTHER INFORMATION: Synthetic Construct

<400> SEQUENCE: 81

Arg Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Tyr Thr
                20                  25                  30

Ser Ser Gln Lys Asn Tyr Leu Ala Trp Tyr Gln Asp Lys Pro Gly Lys
            35                  40                  45

Ala Pro Lys Leu Leu Ile Tyr Trp Ala Ser Thr Arg Glu Ser Gly Val
        50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Tyr Tyr Ala Tyr Pro Trp Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Leu Cys Tyr Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Asp Leu Trp Ser Thr Leu Thr Leu Ser Lys Ala Asp Tyr
                180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
        210                 215                 220

<210> SEQ ID NO 82
<211> LENGTH: 220
<212> TYPE: PRT
<213> ORGANISM: Artificial Sequence
<220> FEATURE:
```

<223> OTHER INFORMATION: Synthetic Construct

<400> SEQUENCE: 82

```
Arg Ile Gln Met Thr Gln Ser Pro Ser Ser Leu Ser Ala Ser Val Gly
1               5                   10                  15

Asp Arg Val Thr Ile Thr Cys Lys Ser Gln Ser Leu Leu Tyr Thr
            20                  25                  30

Ser Ser Gln Lys Asn Tyr Leu Ala Trp Tyr Gln Asp Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Tyr Tyr Ala Tyr Pro Trp Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Leu Cys Tyr Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Gln Leu Trp Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 83
<211> LENGTH: 449
<212> TYPE: PRT
<213> ORGANISM: Artificial Sequence
<220> FEATURE:
<223> OTHER INFORMATION: Synthetic Construct

<400> SEQUENCE: 83

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Tyr Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125
```

```
Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Gln Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Lys Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Lys Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 84
<211> LENGTH: 449
<212> TYPE: PRT
<213> ORGANISM: Artificial Sequence
<220> FEATURE:
<223> OTHER INFORMATION: Synthetic Construct

<400> SEQUENCE: 84

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30
```

```
Tyr Ile His Trp Val Arg Tyr Ala Pro Gly Lys Gly Leu Glu Trp Val
         35                  40                  45
Ala Arg Ile Tyr Pro Thr Asn Gly Tyr Thr Arg Tyr Ala Asp Ser Val
 50                  55                  60
Lys Gly Arg Phe Thr Ile Ser Ala Asp Thr Ser Lys Asn Thr Ala Tyr
 65                  70                  75                  80
Leu Gln Met Asn Ser Leu Arg Ala Glu Asp Thr Ala Val Tyr Tyr Cys
                 85                  90                  95
Ser Arg Trp Gly Gly Asp Gly Phe Tyr Ala Met Asp Tyr Trp Gly Gln
             100                 105                 110
Gly Thr Leu Val Thr Val Ser Ser Ala Ser Thr Lys Gly Pro Ser Val
         115                 120                 125
Phe Pro Leu Ala Pro Cys Ser Lys Ser Thr Ser Gly Gly Thr Ala Ala
 130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                 165                 170                 175
Leu Gln Ser Ser Gly Leu Tyr Ser Leu Ser Ser Val Val Thr Val Pro
             180                 185                 190
Ser Ser Ser Leu Gly Thr Gln Thr Tyr Ile Cys Asn Val Asn His Lys
         195                 200                 205
Pro Ser Asn Thr Lys Val Asp Lys Lys Val Glu Pro Asp Ser Gly Asp
 210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                 245                 250                 255
Ser Arg Thr Pro Glu Val Thr Cys Val Val Val Asp Val Ser His Glu
             260                 265                 270
Asp Pro Glu Val Lys Phe Asn Trp Tyr Val Asp Gly Val Glu Val His
         275                 280                 285
Asn Ala Lys Thr Lys Pro Arg Glu Glu Gln Tyr Gln Ser Thr Tyr Arg
 290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                 325                 330                 335
Lys Thr Ile Ser Lys Ala Lys Gly Gln Pro Arg Glu Pro Gln Val Tyr
             340                 345                 350
Thr Leu Pro Pro Ser Arg Lys Glu Leu Thr Lys Asn Gln Val Ser Leu
         355                 360                 365
Thr Cys Leu Val Lys Gly Phe Tyr Pro Ser Asp Ile Ala Val Glu Trp
 370                 375                 380
Glu Ser Asn Gly Gln Pro Glu Asn Asn Tyr Lys Thr Thr Pro Pro Val
385                 390                 395                 400
Leu Lys Ser Asp Gly Ser Phe Phe Leu Tyr Ser Lys Leu Thr Val Asp
                 405                 410                 415
Lys Ser Arg Trp Gln Gln Gly Asn Val Phe Ser Cys Ser Val Met His
             420                 425                 430
Glu Ala Leu His Asn His Tyr Thr Gln Lys Ser Leu Ser Leu Ser Pro
         435                 440                 445
Gly
```

<210> SEQ ID NO 85
<211> LENGTH: 449
<212> TYPE: PRT
<213> ORGANISM: Artificial Sequence
<220> FEATURE:
<223> OTHER INFORMATION: Synthetic Construct

<400> SEQUENCE: 85

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Tyr Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Arg
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Gln Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Lys Glu Leu Thr Lys Asn Gln Val Ser Leu
        355                 360                 365
```

```
Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Lys Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 86
<211> LENGTH: 449
<212> TYPE: PRT
<213> ORGANISM: Artificial Sequence
<220> FEATURE:
<223> OTHER INFORMATION: Synthetic Construct

<400> SEQUENCE: 86

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Tyr Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Arg
            100                 105                 110

Gly Thr Leu Val Thr Val Ser Ser Ala Ser Thr Lys Gly Pro Ser Val
        115                 120                 125

Phe Pro Leu Ala Pro Cys Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Asp Ser Gly Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270
```

Asp Pro Glu Val Lys Phe Asn Trp Tyr Val Asp Gly Val Glu Val His
            275                 280                 285

Asn Ala Lys Thr Lys Pro Arg Glu Glu Gln Tyr Gln Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Lys Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Lys Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 87
<211> LENGTH: 214
<212> TYPE: PRT
<213> ORGANISM: Artificial Sequence
<220> FEATURE:
<223> OTHER INFORMATION: Synthetic Construct

<400> SEQUENCE: 87

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Arg Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr

```
                        180                 185                 190

Ala Cys Glu Val Thr His Gln Gly Leu Ser Ser Pro Val Thr Lys Ser
            195                 200                 205

Phe Asn Arg Gly Glu Cys
        210

<210> SEQ ID NO 88
<211> LENGTH: 214
<212> TYPE: PRT
<213> ORGANISM: Artificial Sequence
<220> FEATURE:
<223> OTHER INFORMATION: Synthetic Construct

<400> SEQUENCE: 88

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Arg Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Lys Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 89
<211> LENGTH: 214
<212> TYPE: PRT
<213> ORGANISM: Artificial Sequence
<220> FEATURE:
<223> OTHER INFORMATION: Synthetic Construct

<400> SEQUENCE: 89

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Arg Lys Pro Gly Asp Ala Pro Lys Leu Leu Ile
        35                  40                  45
```

```
Tyr Ser Ala Ser Phe Leu Tyr Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                 85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
        195                 200                 205

Phe Asn Arg Gly Glu Cys
210

<210> SEQ ID NO 90
<211> LENGTH: 214
<212> TYPE: PRT
<213> ORGANISM: Artificial Sequence
<220> FEATURE:
<223> OTHER INFORMATION: Synthetic Construct

<400> SEQUENCE: 90

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Val Asn Thr Ala
                 20                  25                  30

Val Ala Trp Tyr Gln Arg Lys Pro Gly Asp Ala Pro Lys Leu Leu Ile
             35                  40                  45

Tyr Ser Ala Ser Phe Leu Tyr Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                 85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Lys Glu Gln Leu Lys Ser Gly
                115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190
```

Ala Cys Glu Val Thr His Gln Gly Leu Ser Ser Pro Val Thr Lys Ser
            195                 200                 205

Phe Asn Arg Gly Glu Cys
    210

<210> SEQ ID NO 91
<211> LENGTH: 448
<212> TYPE: PRT
<213> ORGANISM: Artificial Sequence
<220> FEATURE:
<223> OTHER INFORMATION: Synthetic Construct

<400> SEQUENCE: 91

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Tyr Ala Pro Gly Lys Gly Leu Glu Trp Val
        35                  40                  45

Ala Asp Val Asn Pro Asn Ser Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Gln Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Lys Glu Leu Thr Lys Asn Gln Val Ser Leu Thr
355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Lys Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

<210> SEQ ID NO 92
<211> LENGTH: 448
<212> TYPE: PRT
<213> ORGANISM: Artificial Sequence
<220> FEATURE:
<223> OTHER INFORMATION: Synthetic Construct

<400> SEQUENCE: 92

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Tyr Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Asp Ser Gly Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

```
Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Gln Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Lys Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Lys Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 93
<211> LENGTH: 448
<212> TYPE: PRT
<213> ORGANISM: Artificial Sequence
<220> FEATURE:
<223> OTHER INFORMATION: Synthetic Construct

<400> SEQUENCE: 93

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Tyr Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Arg Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175
```

```
Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Gln Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Lys Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Lys Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 94
<211> LENGTH: 448
<212> TYPE: PRT
<213> ORGANISM: Artificial Sequence
<220> FEATURE:
<223> OTHER INFORMATION: Synthetic Construct

<400> SEQUENCE: 94

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Tyr Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

Ala Arg Asn Leu Gly Pro Ser Phe Tyr Phe Asp Tyr Trp Gly Arg Gly
            100                 105                 110

Thr Leu Val Thr Val Ser Ser Ala Ser Thr Lys Gly Pro Ser Val Phe
        115                 120                 125

Pro Leu Ala Pro Cys Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Asp Ser Gly Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Gln Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Lys Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Lys Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 95
<211> LENGTH: 214
<212> TYPE: PRT
<213> ORGANISM: Artificial Sequence
<220> FEATURE:
<223> OTHER INFORMATION: Synthetic Construct

<400> SEQUENCE: 95

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Arg Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ile Tyr Pro Tyr
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Lys Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 96
<211> LENGTH: 214
<212> TYPE: PRT
<213> ORGANISM: Artificial Sequence
<220> FEATURE:
<223> OTHER INFORMATION: Synthetic Construct

<400> SEQUENCE: 96

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Arg Lys Pro Gly Asp Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ile Tyr Pro Tyr
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

```
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 97
<211> LENGTH: 214
<212> TYPE: PRT
<213> ORGANISM: Artificial Sequence
<220> FEATURE:
<223> OTHER INFORMATION: Synthetic Construct

<400> SEQUENCE: 97

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Arg Lys Pro Gly Asp Ala Pro Lys Leu Leu Ile
        35                  40                  45

Tyr Ser Ala Ser Tyr Arg Tyr Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Lys Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 98
<211> LENGTH: 450
<212> TYPE: PRT
<213> ORGANISM: Artificial Sequence
<220> FEATURE:
<223> OTHER INFORMATION: Synthetic Construct

<400> SEQUENCE: 98

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
            20                  25                  30
```

Trp Met His Trp Val Arg Tyr Ala Pro Gly Gln Gly Leu Glu Trp Ile
    35                  40                  45

Gly Glu Phe Asn Pro Ser Asn Gly Arg Thr Asn Tyr Asn Glu Lys Phe
 50                  55                  60

Lys Ser Lys Ala Thr Met Thr Val Asp Thr Ser Thr Asn Thr Ala Tyr
 65                  70                  75                  80

Met Glu Leu Ser Ser Leu Arg Ser Glu Asp Thr Ala Val Tyr Tyr Cys
                 85                  90                  95

Ala Ser Arg Asp Tyr Asp Tyr Asp Gly Arg Tyr Phe Asp Tyr Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Cys Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Asp Ser Gly
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Gln Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Lys Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Lys Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450

<210> SEQ ID NO 99
<211> LENGTH: 450
<212> TYPE: PRT
<213> ORGANISM: Artificial Sequence
<220> FEATURE:
<223> OTHER INFORMATION: Synthetic Construct

<400> SEQUENCE: 99

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
                20                  25                  30

Trp Met His Trp Val Arg Tyr Ala Pro Gly Gln Gly Leu Glu Trp Ile
            35                  40                  45

Gly Glu Phe Asn Pro Ser Asn Gly Arg Thr Asn Tyr Asn Glu Lys Phe
        50                  55                  60

Lys Ser Lys Ala Thr Met Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Ser Arg Asp Tyr Asp Tyr Asp Gly Arg Tyr Phe Asp Tyr Trp Gly
                100                 105                 110

Arg Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Gln Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

```
Tyr Thr Leu Pro Pro Ser Arg Lys Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Lys Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450

<210> SEQ ID NO 100
<211> LENGTH: 450
<212> TYPE: PRT
<213> ORGANISM: Artificial Sequence
<220> FEATURE:
<223> OTHER INFORMATION: Synthetic Construct

<400> SEQUENCE: 100

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
            20                  25                  30

Trp Met His Trp Val Arg Tyr Ala Pro Gly Gln Gly Leu Glu Trp Ile
        35                  40                  45

Gly Glu Phe Asn Pro Ser Asn Gly Arg Thr Asn Tyr Asn Glu Lys Phe
    50                  55                  60

Lys Ser Lys Ala Thr Met Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Ser Arg Asp Tyr Asp Tyr Asp Gly Arg Tyr Phe Asp Tyr Trp Gly
            100                 105                 110

Arg Gly Thr Leu Val Thr Val Ser Ser Ala Ser Thr Lys Gly Pro Ser
        115                 120                 125

Val Phe Pro Leu Ala Pro Cys Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Asp Ser Gly
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255
```

-continued

```
Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Gln Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Lys Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Tyr Lys Thr Thr Pro Pro
385                 390                 395                 400

Val Leu Lys Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450

<210> SEQ ID NO 101
<211> LENGTH: 213
<212> TYPE: PRT
<213> ORGANISM: Artificial Sequence
<220> FEATURE:
<223> OTHER INFORMATION: Synthetic Construct

<400> SEQUENCE: 101

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Thr Tyr Met
            20                  25                  30

Tyr Trp Tyr Gln Arg Lys Pro Gly Lys Ala Pro Lys Leu Leu Ile Tyr
        35                  40                  45

Asp Thr Ser Asn Leu Ala Ser Gly Val Pro Ser Arg Phe Ser Gly Ser
    50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln Gln Trp Ser Ser His Ile Phe Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Lys Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160
```

```
Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 102
<211> LENGTH: 213
<212> TYPE: PRT
<213> ORGANISM: Artificial Sequence
<220> FEATURE:
<223> OTHER INFORMATION: Synthetic Construct

<400> SEQUENCE: 102

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Thr Tyr Met
            20                  25                  30

Tyr Trp Tyr Gln Arg Lys Pro Gly Asp Ala Pro Lys Leu Leu Ile Tyr
        35                  40                  45

Asp Thr Ser Asn Leu Ala Ser Gly Val Pro Ser Arg Phe Ser Gly Ser
    50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln Gln Trp Ser His Ile Phe Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 103
<211> LENGTH: 213
<212> TYPE: PRT
<213> ORGANISM: Artificial Sequence
<220> FEATURE:
<223> OTHER INFORMATION: Synthetic Construct

<400> SEQUENCE: 103

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Thr Tyr Met
            20                  25                  30
```

Tyr Trp Tyr Gln Arg Lys Pro Gly Asp Ala Pro Lys Leu Leu Ile Tyr
            35                  40                  45

Asp Thr Ser Asn Leu Ala Ser Gly Val Pro Ser Arg Phe Ser Gly Ser
    50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln Gln Trp Ser Ser His Ile Phe Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Lys Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
        210

<210> SEQ ID NO 104
<211> LENGTH: 445
<212> TYPE: PRT
<213> ORGANISM: Artificial Sequence
<220> FEATURE:
<223> OTHER INFORMATION: Synthetic Construct

<400> SEQUENCE: 104

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Thr Tyr
            20                  25                  30

Tyr Leu His Trp Val Arg Tyr Ala Pro Gly Gln Gly Leu Glu Trp Met
        35                  40                  45

Gly Trp Ile Tyr Pro Gly Asn Val His Ala Gln Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Trp Glu Gly Phe Pro Tyr Trp Gly Gln Gly Thr Thr Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

```
Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Gln Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Lys Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Lys Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
        435                 440                 445

<210> SEQ ID NO 105
<211> LENGTH: 445
<212> TYPE: PRT
<213> ORGANISM: Artificial Sequence
<220> FEATURE:
<223> OTHER INFORMATION: Synthetic Construct

<400> SEQUENCE: 105

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Thr Tyr
            20                  25                  30

Tyr Leu His Trp Val Arg Tyr Ala Pro Gly Gln Gly Leu Glu Trp Met
        35                  40                  45

Gly Trp Ile Tyr Pro Gly Asn Val His Ala Gln Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

```
Ala Arg Ser Trp Glu Gly Phe Pro Tyr Trp Gly Gln Gly Thr Thr Val
            100                 105                 110

Thr Val Ser Ser Ala Ser Thr Lys Gly Pro Ser Val Phe Pro Leu Ala
        115                 120                 125

Pro Cys Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Asp Ser Gly Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Gln Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Lys Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Lys Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
        435                 440                 445

<210> SEQ ID NO 106
<211> LENGTH: 445
<212> TYPE: PRT
<213> ORGANISM: Artificial Sequence
<220> FEATURE:
<223> OTHER INFORMATION: Synthetic Construct

<400> SEQUENCE: 106

Gln Val Gln Leu Val Gln Ser Gly Ala Glu Val Lys Lys Pro Gly Ser
1               5                   10                  15
```

-continued

Ser Val Lys Val Ser Cys Lys Ala Ser Gly Tyr Thr Phe Thr Thr Tyr
            20                  25                  30

Tyr Leu His Trp Val Arg Tyr Ala Pro Gly Gln Gly Leu Glu Trp Met
        35                  40                  45

Gly Trp Ile Tyr Pro Gly Asn Val His Ala Gln Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Trp Glu Gly Phe Pro Tyr Trp Gly Arg Gly Thr Thr Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Gln Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Lys Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Lys Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

-continued

```
Asn His Tyr Thr Gln Lys Ser Leu Ser Leu Ser Pro Gly
            435                 440                 445

<210> SEQ ID NO 107
<211> LENGTH: 445
<212> TYPE: PRT
<213> ORGANISM: Artificial Sequence
<220> FEATURE:
<223> OTHER INFORMATION: Synthetic Construct

<400> SEQUENCE: 107

Gln Val Gln Leu Val Gln Ser Gly Ala Glu Val Lys Pro Gly Ser
1               5                   10                  15

Ser Val Lys Val Ser Cys Lys Ala Ser Gly Tyr Thr Phe Thr Tyr
                20                  25                  30

Tyr Leu His Trp Val Arg Tyr Ala Pro Gly Gln Gly Leu Glu Trp Met
                35                  40                  45

Gly Trp Ile Tyr Pro Gly Asn Val His Ala Gln Tyr Asn Glu Lys Phe
        50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Trp Glu Gly Phe Pro Tyr Trp Gly Arg Gly Thr Thr Val
            100                 105                 110

Thr Val Ser Ser Ala Ser Thr Lys Gly Pro Ser Val Phe Pro Leu Ala
            115                 120                 125

Pro Cys Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Asp Ser Gly Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Gln Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350
```

```
Ser Arg Lys Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Lys Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
        435                 440                 445

<210> SEQ ID NO 108
<211> LENGTH: 449
<212> TYPE: PRT
<213> ORGANISM: Artificial Sequence
<220> FEATURE:
<223> OTHER INFORMATION: Synthetic Construct

<400> SEQUENCE: 108

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Lys Ala Pro Gly Lys Gly Leu Glu Trp Val
        35                  40                  45

Ala Arg Ile Tyr Pro Thr Asn Gly Tyr Thr Arg Tyr Ala Asp Glu Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270
```

```
Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Asp Thr Thr Pro Pro Val
385                 390                 395                 400

Leu Asp Ser Asp Gly Ser Phe Phe Leu Tyr Ser Asp Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 109
<211> LENGTH: 214
<212> TYPE: PRT
<213> ORGANISM: Artificial Sequence
<220> FEATURE:
<223> OTHER INFORMATION: Synthetic Construct

<400> SEQUENCE: 109

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Ile Asn
            20                  25                  30

Val Ala Trp Tyr Gln Arg Lys Pro Gly Lys Ala Pro Lys Ser Leu Ile
        35                  40                  45

Ser Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Tyr Asp Thr Tyr Pro Phe
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
```

-continued

```
                180                 185                 190
Ala Cys Glu Val Thr His Gln Gly Leu Ser Ser Pro Val Thr Lys Ser
            195                 200                 205

Phe Asn Arg Gly Glu Cys
    210

<210> SEQ ID NO 110
<211> LENGTH: 214
<212> TYPE: PRT
<213> ORGANISM: Artificial Sequence
<220> FEATURE:
<223> OTHER INFORMATION: Synthetic Construct

<400> SEQUENCE: 110

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Ile Asn
            20                  25                  30

Val Ala Trp Tyr Gln Arg Lys Pro Gly Lys Ala Pro Lys Ser Leu Ile
        35                  40                  45

Ser Ser Ala Ser Tyr Arg Tyr Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Tyr Asp Thr Tyr Pro Phe
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Lys Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 111
<211> LENGTH: 214
<212> TYPE: PRT
<213> ORGANISM: Artificial Sequence
<220> FEATURE:
<223> OTHER INFORMATION: Synthetic Construct

<400> SEQUENCE: 111

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Ile Asn
            20                  25                  30

Val Ala Trp Tyr Gln Arg Lys Pro Gly Asp Ala Pro Lys Ser Leu Ile
        35                  40                  45
```

```
Ser Ser Ala Ser Tyr Arg Tyr Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Phe Cys Gln Gln Tyr Asp Thr Tyr Pro Phe
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
210

<210> SEQ ID NO 112
<211> LENGTH: 214
<212> TYPE: PRT
<213> ORGANISM: Artificial Sequence
<220> FEATURE:
<223> OTHER INFORMATION: Synthetic Construct

<400> SEQUENCE: 112

Asp Ile Gln Met Thr Gln Ser Pro Ser Ser Leu Ser Ala Ser Val Gly
1               5                  10                  15

Asp Arg Val Thr Ile Thr Cys Lys Ala Ser Gln Asn Val Gly Ile Asn
             20                  25                  30

Val Ala Trp Tyr Gln Arg Lys Pro Gly Asp Ala Pro Lys Ser Leu Ile
         35                  40                  45

Ser Ser Ala Ser Tyr Arg Tyr Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Phe Cys Gln Gln Tyr Asp Thr Tyr Pro Phe
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Lys Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

```
Ala Cys Glu Val Thr His Gln Gly Leu Ser Ser Pro Val Thr Lys Ser
        195                 200                 205

Phe Asn Arg Gly Glu Cys
    210

<210> SEQ ID NO 113
<211> LENGTH: 214
<212> TYPE: PRT
<213> ORGANISM: Artificial Sequence
<220> FEATURE:
<223> OTHER INFORMATION: Synthetic Construct

<400> SEQUENCE: 113

Arg Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Asp Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Tyr Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Trp
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```